US012686659B2

(12) United States Patent
Iovine et al.

(10) Patent No.: US 12,686,659 B2
(45) Date of Patent: Jul. 21, 2026

(54) MULTIVALENT TERPENE-BASED BOLAAMPHIPHILES FOR GENE DELIVERY

(71) Applicant: University of San Diego, San Diego, CA (US)

(72) Inventors: Peter M. Iovine, San Diego, CA (US); Gopi Nath Vemuri, San Diego, CA (US); Jake Hughes, San Diego, CA (US)

(73) Assignee: University of San Diego, San Diego, CA (US)

( * ) Notice: Subject to any disclaimer, the term of this patent is extended or adjusted under 35 U.S.C. 154(b) by 563 days.

(21) Appl. No.: 18/032,499

(22) PCT Filed: Oct. 20, 2021

(86) PCT No.: PCT/US2021/055910
§ 371 (c)(1),
(2) Date: Apr. 18, 2023

(87) PCT Pub. No.: WO2022/087175
PCT Pub. Date: Apr. 28, 2022

(65) Prior Publication Data

US 2024/0018101 A1 Jan. 18, 2024

Related U.S. Application Data

(60) Provisional application No. 63/241,808, filed on Sep. 8, 2021, provisional application No. 63/094,665, filed on Oct. 21, 2020.

(51) Int. Cl.

| | |
|---|---|
| ***C07C 323/61*** | (2006.01) |
| ***A61K 47/20*** | (2006.01) |
| ***A61K 47/22*** | (2006.01) |
| ***C07C 323/47*** | (2006.01) |
| ***C07D 209/48*** | (2006.01) |

(52) U.S. Cl.
CPC ............ *C07C 323/61* (2013.01); *A61K 47/20* (2013.01); *A61K 47/22* (2013.01); *C07C 323/47* (2013.01); *C07D 209/48* (2013.01); *C07C 2601/14* (2017.05)

(58) Field of Classification Search
CPC .............................. C07C 323/61; A61K 47/20
See application file for complete search history.

(56) References Cited

U.S. PATENT DOCUMENTS

| | | | |
|---|---|---|---|
| 5,403,022 | A | 4/1995 | Garelli-Calvet et al. |
| 2015/0246138 | A1 | 9/2015 | Linder et al. |

FOREIGN PATENT DOCUMENTS

| | | | |
|---|---|---|---|
| WO | 2012158250 | A1 | 11/2012 |

OTHER PUBLICATIONS

International Search Report for corresponding PCT Application No. PCT/US2021/055910 mailed Jan. 27, 2022.
PUBCHEM-SID:312898605 Deposit Date: Apr. 9, 2016.
PUBCHEM-SID:124662152 Deposit Date: Aug. 2, 2011.

*Primary Examiner* — Golam M Shameem
(74) *Attorney, Agent, or Firm* — Wood, Phillips, Katz, Clark & Mortimer

(57) ABSTRACT

Multifunctional amine-containing bolaamphiphilic compositions comprising hydrocarbon terpenes, methods of preparing such compositions, and the use of these compositions in gene delivery applications are disclosed.

25 Claims, 1 Drawing Sheet

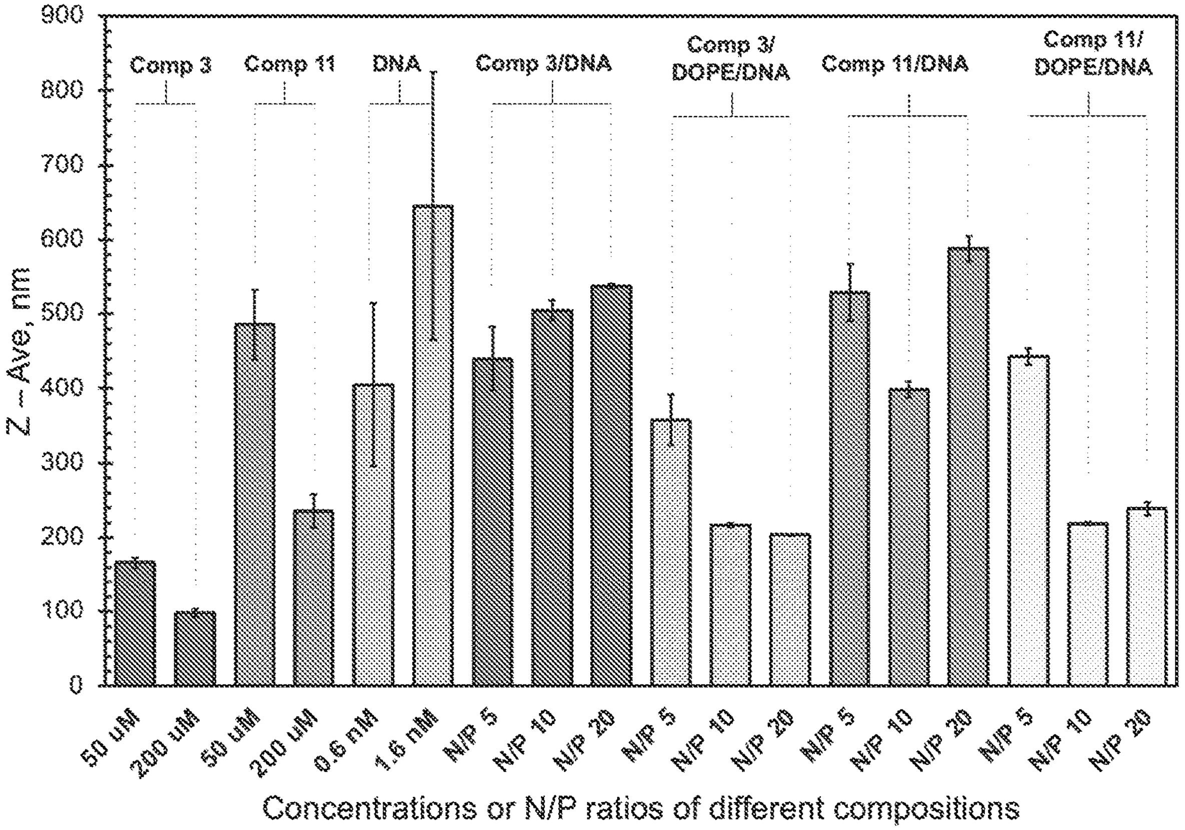
900
800
700
600
500
400
300
200
100
0
Z – Ave, nm
Comp 3
Comp 11
DNA
Comp 3/DNA
Comp 3/
DOPE/DNA
Comp 11/DNA
Comp 11/
DOPE/DNA
50 uM
200 uM
50 uM
200 uM
0.6 nM
1.6 nM
N/P 5
N/P 10
N/P 20
N/P 5
N/P 10
N/P 20
N/P 5
N/P 10
N/P 20
N/P 5
N/P 10
N/P 20
Concentrations or N/P ratios of different compositions

MULTIVALENT TERPENE-BASED BOLAAMPHIPHILES FOR GENE DELIVERY

FIELD OF THE INVENTION

The present invention relates generally to novel multi-functional amine-containing bolaamphiphilic compositions comprising hydrocarbon terpenes, methods of preparing these compositions, and the use of these compositions in gene delivery.

BACKGROUND OF THE INVENTION

The concept of gene delivery has emerged as a useful approach to treating acquired and genetic disorders such as cancer, cystic fibrosis, hemophilia, vascular disease, infectious diseases and many others. Two major delivery systems (vectors), viral and non-viral, are currently used in both clinical and research studies. Although viral vectors are efficient in delivery, limitations such as low DNA/RNA loading capacity, immunogenicity and toxicity have encouraged the development of non-viral vectors. Non-viral vectors offer non-toxic and highly efficient gene delivery systems due to their facile chemistry, flexible manufacturing and safe toxicity profiles (e.g., see *Polymers and Nanomaterials for Gene Therapy*, Woodhead Publishing, Elsevier, 2016 Ravin Narain editor). Cationic polymers, dendrimers and cationic lipids effectively condense DNA/RNA into nanometer-micrometer sized complexes via electrostatic interaction, and protect the payload from enzymatic/nonenzymatic degradation and enhance cellular communication (e.g., see Mintzer, M. A.; Simanek, E. E. Nonviral Vectors for Gene Delivery. *Chem. Rev.* 2009, 109(2), 259-302).

Among the various types of non-viral vectors, cationic lipids are especially attractive and useful. These materials have shown great potential in gene delivery because of their lower immunogenic nature, ability to deliver large pieces of nucleic acids and ease of handling and preparation (e.g., see Huang, Z.; Zhang, Y.-M.; Cheng, Q.; Zhang, J.; Liu, Y.-H.; Wang, B.; Yu, X.-Q. Structure-activity Relationship Studies of Symmetrical Cationic Bolasomes as Non-Viral Gene Vectors. *J. Materials Chem. B.* 2016, 4, 5575-5584). Cationic lipids are amphiphilic molecules possessing a hydrophilic head and a hydrophobic tail. A cationic amine head group, for example, can electrostatically bind with DNA/RNA molecules and condense into small transportable units called lipoplexes. It is believed that lipoplexes enter cells via endocytosis followed by the release of DNA into the cytoplasm after membrane phospholipid remodeling.

Most of the cationic lipids of the prior art are "monopolar" amphiphiles. Structurally, these monopolar amphiphiles generally contain just one polar head group which is attached to hydrophobic tails via a linking group. The vast majority of cationic lipids rely on the charge accommodated on a nitrogen atom. There is a relationship between the hydration of such mono-ammonium head groups and transfection efficiency (e.g., see Martin, B.; Sainlos, M.; Aissaoui, A.; Oudrhiri, N.; Hauchecome, M.; Vigneron, J. P.; Lehn, J.-M.; Lehn, P. The Design of Cationic Lipids for Gene Delivery. *Current Pharmaceutical Design,* 2005, 11, 375-394). The greater the imbalance between the cross-sectional area of the hydrated head group and the hydrophobic moiety, the more unstable the resulting lipid assembly and the greater the potential to undergo fusion with anionic vesicles. Lipoplex instability is presumed to result in improved transfection as fusion between the cationic lipoplex and the endosomal membrane leads to DNA release in the cytoplasm.

The compositions and methods of the present disclosure have wide applicability to a diverse number of fields, including gene therapy and the production of cell-based therapeutics.

SUMMARY OF THE INVENTION

In one aspect, the present composition can be a multivalent cationic bolaamphiphilic compound represented by Formula (I):

Formula (I)

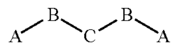

wherein:

each A is a group having a formula selected from the following:

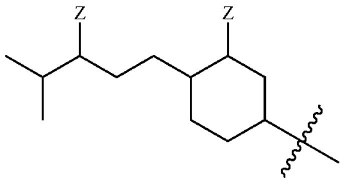

,

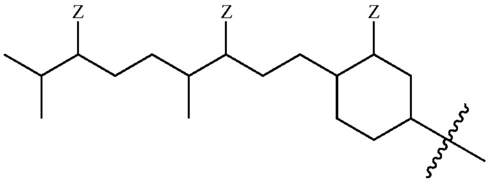

,

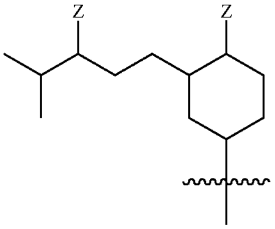

,

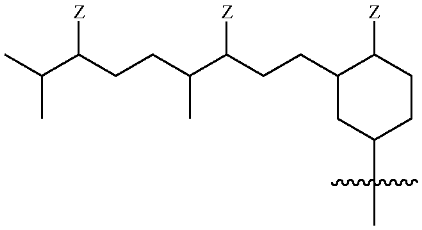

,

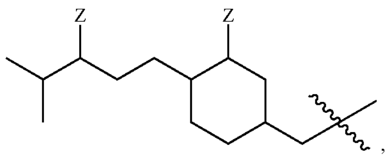

,

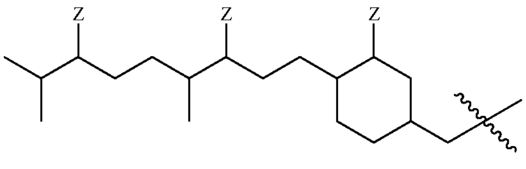

,

-continued

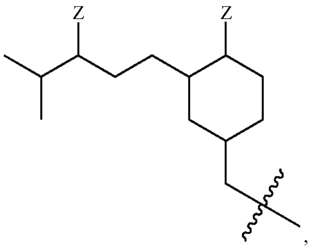,

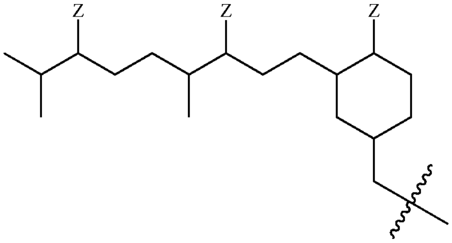,

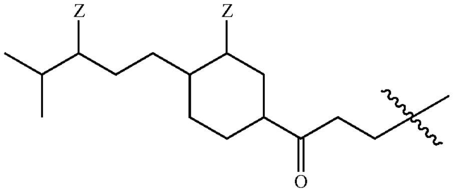,

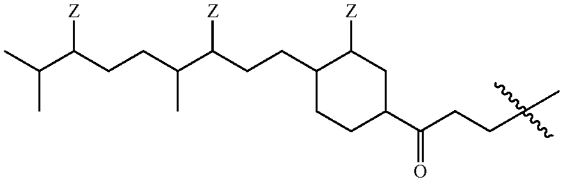,

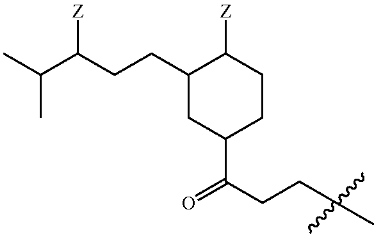,

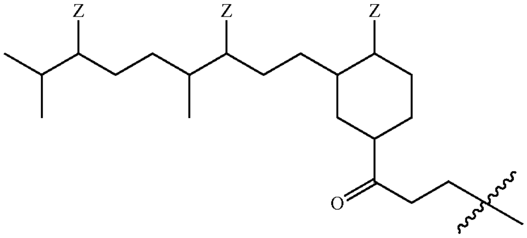,

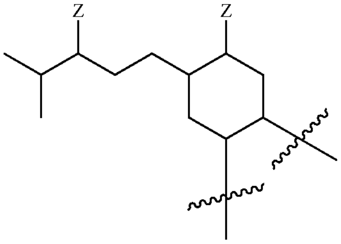,

-continued

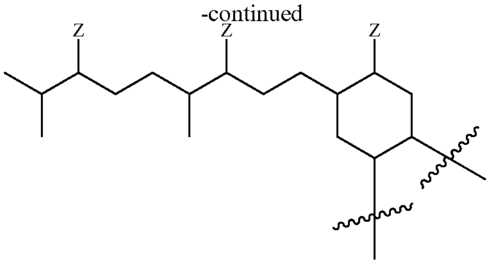, each Z is independently —S—$R_1$;

each $R_1$ is independently selected from a group having a formula selected from the following:

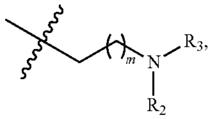 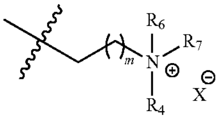,

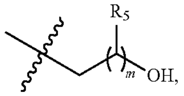 or 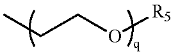;

each $R_2$ or $R_3$ is independently selected from hydrogen, $C_1$-$C_6$ alkyl, $C_1$-$C_6$ alkenyl, aralkyl, or hydroxyalkyl;

each $R_4$, $R_6$ or $R_7$ is independently selected from $C_1$-$C_6$ alkyl, $C_1$-$C_6$ alkenyl, or hydroxyalkyl;

each $R_5$ is hydrogen or $C_1$-$C_6$ alkyl;

each X is halogen;

each m is an integer independently selected from 1-11;

each q is an integer independently selected from 1-200;

each B is a group having a formula independently selected from the following:

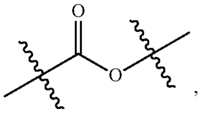, 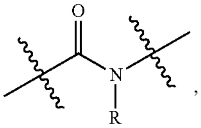,

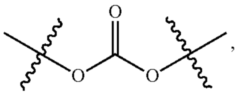, 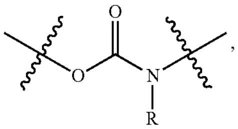, or

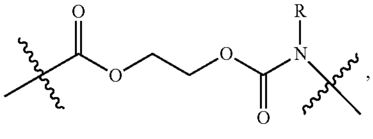, wherein each R is independently selected from hydrogen or $C_1$-$C_6$ alkyl; and C is:

a. a C2-C100 hydrocarbon chain which can optionally contain one or more S atoms;

b. $Cyc^A$-L-$Cyc^B$, wherein $Cyc^A$ and $Cyc^B$ are each independently a 5-8 membered cycloalkyl and L is $C_1$-$C_3$ alkylene;

c. a polyalkylene oxide or polyalkylene oxide block copolymers of 200-5,000 molecular weight;

d. an aliphatic or aromatic polyester of 200-5,000 molecular weight; or e. an aliphatic or aromatic polyurethane of 200-5,000 molecular weight; or

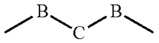

together are:

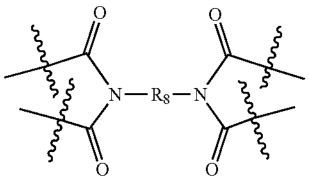

wherein each $R_8$ is independently selected from $C_2$-$C_6$ alkyl, aryl,

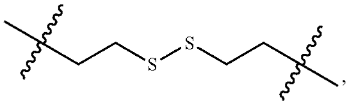
,

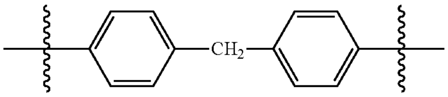
,

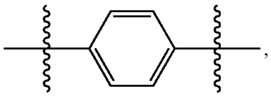
,
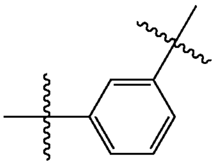
,

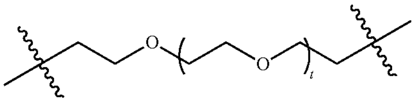

each t is an integer independently selected from 1-10.

In one aspect, the compositions can be a lipoplex composition comprising a compound of Formula (I) and at least one nucleic acid.

In some aspects, the compositions can be pharmaceutical compositions comprising a compound of Formula (I), at least one nucleic acid and one or more pharmaceutically-acceptable excipient or diluent.

In one aspect, the present compositions can be used to deliver at least one nucleic acid to at least one cell by contacting the at least one cell with the present composition.

Unless otherwise defined, all technical and scientific terms used herein have the same meaning as commonly understood by one of ordinary skill in the art to which this disclosure belongs. In the specification, the singular forms also include the plural unless the context clearly dictates otherwise. The terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The term "about" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about." Ranges which are described as being "between" two values include the indicated values.

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present specification, including definitions, will control. In addition, the materials, methods, and examples are illustrative only and are not intended to be limiting. Other features and advantages of the disclosure will be apparent from the following detailed description and claims.

BRIEF DESCRIPTION OF THE DRAWINGS

FIG. 1 is a bar graph showing the size of the nanoparticle formed with various concentrations of individual components and bolaplexes.

DETAILED DESCRIPTION OF THE INVENTION

Definitions

In the chemical formulas shown herein, the marking

indicates the position where a functional group bonds to another portion of a molecule. As used herein, the term "alkyl" refers to straight and branched chain aliphatic groups having from 1 to 12 carbon atoms, As such, "alkyl" encompasses $C_1$, $C_2$, $C_3$, $C_4$, $C_5$, $C_6$, $C_7$, $C_8$, $C_9$, $C_{10}$, $C_{11}$ and $C_{12}$ groups. For instance, a $C_1$-$C_6$ alkyl group includes alkyl groups having 1 to 6 carbons. Examples of alkyl groups include, without limitation, methyl, ethyl, propyl, isopropyl, butyl, isobutyl, sec-butyl, tert-butyl, pentyl, and hexyl.

As used herein, the term "alkylene" is an alkyl, as defined hereinabove, that is positioned between and serves to connect two other chemical groups. Examples of alkylene groups include, without limitation, methylene, ethylene, propylene, butylene, pentylene and hexylene.

As used herein, the term "alkenyl" refers to an unsaturated straight or branched chain aliphatic group with one or more carbon-carbon double bonds, having from 2 to 12 carbon atoms. As such, "alkenyl" encompasses $C_2$, $C_3$, $C_4$, $C_5$, $C_6$, $C_7$, $C_8$, $C_9$, $C_{10}$, $C_{11}$ and $C_{12}$ groups. Examples of alkynyl groups include, without limitation, ethynyl, propynyl, butynyl, pentynyl, and hexynyl.

As used herein, the term "aralkyl" group comprises an aryl group covalently linked to an alkyl group, either of which can independently be optionally substituted or unsubstituted. An example of an aralkyl group is —($C_1$-$C_6$)alkyl($C_6$-$C_{10}$)aryl, including, without limitation, benzyl, phenethyl, and naphthylmethyl.

As used herein, the term "aryl" group is a $C_6$-$C_{14}$ aromatic moiety comprising one to three aromatic rings, which is optionally substituted. As such, "aryl" includes $C_6$, $C_7$, $C_8$, $C_9$, $C_{10}$, $C_{11}$, $C_{12}$ $C_{13}$, and $C_{14}$ cyclic hydrocarbon groups. An exemplary aryl group is a C.sub.6-C.sub.10 aryl group. Particular aryl groups include, without limitation, phenyl, naphthyl, anthracenyl, and fluorenyl.

As used herein, the term "C2-C100 hydrocarbon chain" refers to straight or branched chain, saturated or unsaturated comprising 2 to 100 carbon atoms. Examples of C2-C100 hydrocarbon chains groups include ethyl, propyl, isopropyl, butyl, isobutyl, sec-butyl, tert-butyl, pentyl, hexyl, heptanyl, octanyl, nonanyl, decanyl, undecanyl, dodecanyl, tridecanyl, icosanyl, triacontanyl, and tetracontanyl, and unsaturated counterparts thereof, e.g., propenyl and propynyl counterparts of propyl.

As used herein, the term "cycloalkyl" as employed herein includes saturated and partially unsaturated cyclic hydrocarbon groups having 3 to 12 carbons. As such, "cycloalkyl" includes $C_3$, $C_4$, $C_5$, $C_6$, $C_7$, $C_8$, $C_9$, $C_{10}$, $C_{11}$ and $C_{12}$ cyclic hydrocarbon groups. Representative cycloalkyl groups include, without limitation, cyclopropyl, cyclobutyl, cyclopentyl, cyclopentenyl, cyclohexyl, cyclohexenyl, cycloheptyl, and cyclooctyl.

As used herein, the terms "halo" and "halogen" refer to fluoro, chloro, bromo and iodo.

As used herein, the term "hydroxyalkyl" refers to -alkyl-OH or an alkyl chain substituted with at least one —OH.

Compositions of the Present Disclosure—Terpene-Derived Multivalent Cationic Bolaamphiphilic Compositions The present disclosure provides novel multivalent cationic bolaamphiphilic compositions, methods for preparing the cationic bolaamphiphilic compositions, and methods for using same.

In a non-limiting example, the compositions and methods of the present disclosure can be used for gene delivery.

The multivalent cationic bolaamphiphilic compositions of the present disclosure comprise multivalent cationic lipids that can form lipoplexes with greater surface charge density than their monovalent counterparts and result in better binding to nucleic acids, e.g., DNA, and enhanced delivery. The presence of these protonation sites with different pKa values can result in buffering of endosomal acidification, thereby protecting nucleic acids from degradation and facilitating their escape from the endosome. With more protonation sites per molecule, the lipoplexes resulting from multivalent cationic lipids can achieve the same charge density (P/N ratio) as monofunctional cationic lipids with lesser amounts of cationic lipids in the formulation, thereby lessening cationic lipid-associated cytotoxicity.

Compounds

In one aspect, the present disclosure provides novel multivalent cationic bolaamphiphilic compounds of Formula (I).

In one embodiment, the multivalent cationic bolaamphiphilic compositions are derived from certain terpenes and amine, hydroxyalkyl and polyalkylenoxide-functionalized thiols. In one embodiment, the multivalent cationic bolaamphiphilic compositions are comprised of a hydrophobic chain ("C") segment covalently linked at both ends to a multivalent hydrophilic cationic head groups ("A") segment built on a terpene frame using a thiol-ene click addition chemistry.

In one aspect, the multivalent cationic bolaamphiphilic compounds are represented by Formula (I):

Formula (I)

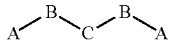

wherein:

each A is a group having a formula selected from the following:

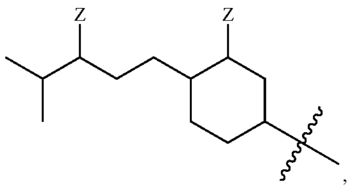
,

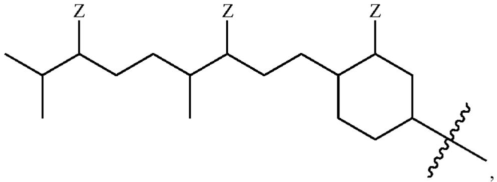
,

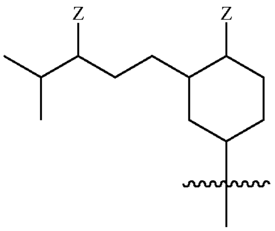
,

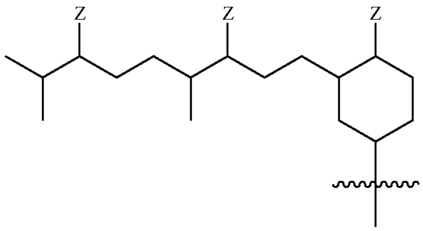
,

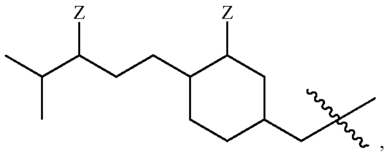
,

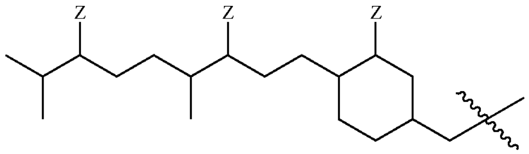
,

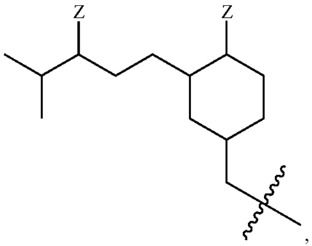
,

-continued

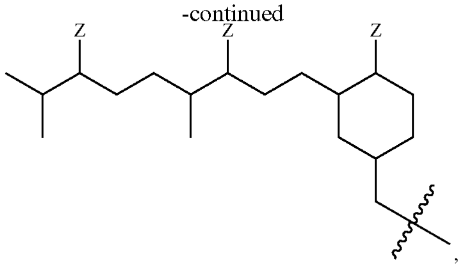

,

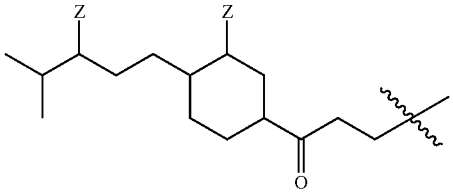

,

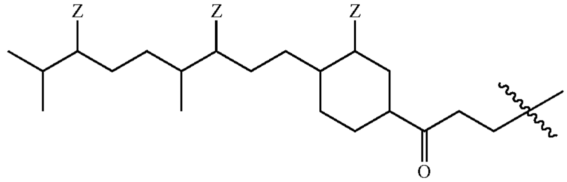

,

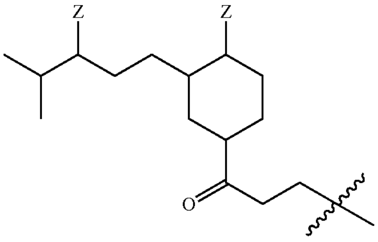

,

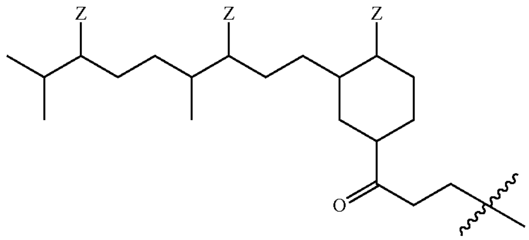

,

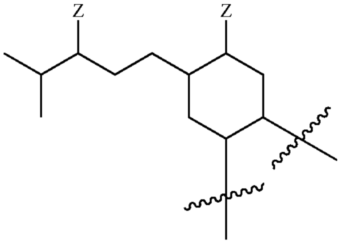

,

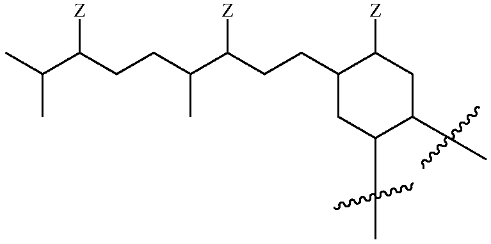

;

each Z is independently —S—$R_1$;

each $R_1$ is independently selected from a group having a formula selected from the following:

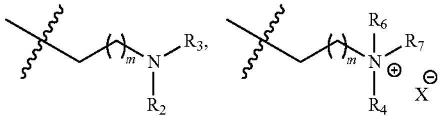

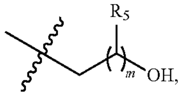

or

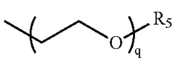

;

each $R_2$ or $R_3$ is independently selected from hydrogen, $C_1$-$C_6$ alkyl, $C_1$-$C_6$ alkenyl, aralkyl, or hydroxyalkyl;

each $R_4$, $R_6$ or $R_7$ is independently selected from $C_1$-$C_6$ alkyl, $C_1$-$C_6$ alkenyl, or hydroxyalkyl;

each $R_5$ is hydrogen or $C_1$-$C_6$ alkyl;

each X is halogen;

each m is an integer independently selected from 1-11;

each q is an integer independently selected from 1-200;

each B is independently selected from:

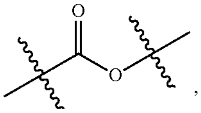

,

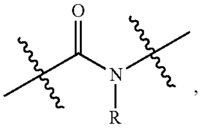

,

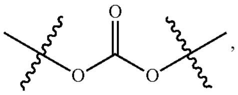

,

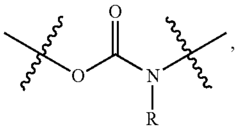

, or

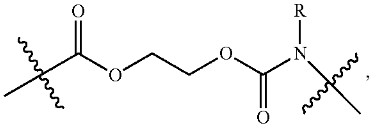

, wherein each R is independently selected from hydrogen or $C_1$-$C_6$ alkyl; and C is:

a. a C2-C100 hydrocarbon chain which can optionally contain one or more S atoms;

b. $Cyc^A$-L-$Cyc^B$, wherein $Cyc^A$ and $Cyc^B$ are each independently a 5-8 membered cycloalkyl and L is $C_1$-$C_3$ alkylene;

c. a polyalkylene oxide or polyalkylene oxide block copolymers of 200-5,000 molecular weight;

d. an aliphatic or aromatic polyester of 200-5,000 molecular weight; or e. an aliphatic or aromatic polyurethane of 200-5,000 molecular weight; or

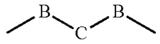

together form:

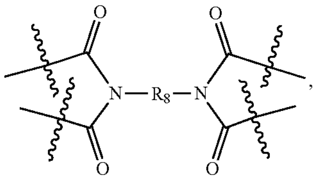

, wherein each $R_8$ is independently selected from C2-C6 alkyl, aryl,

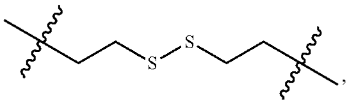

,

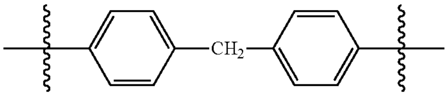

,

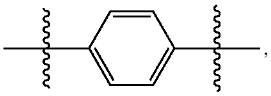

,

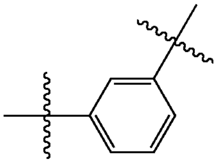

,

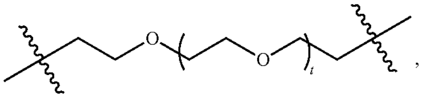

, each t is an integer independently selected from 1-10;

In some aspects, each A segment is:

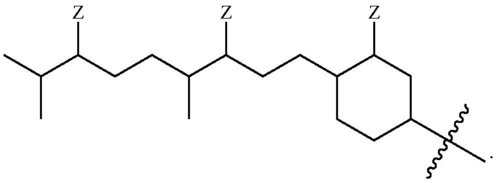

In some aspects, each A segment is:

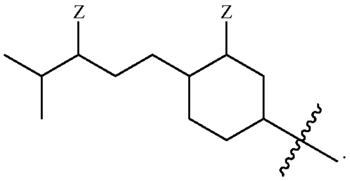

In some aspects, each A segment is:

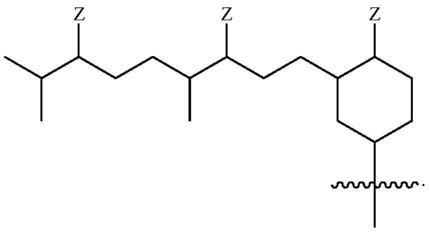

In some aspects, each A segment is:

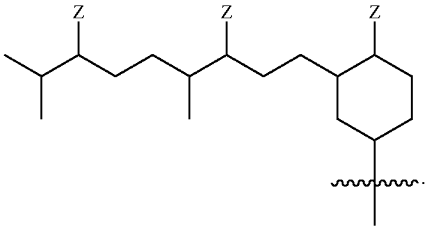

In some aspects, each A segment is:

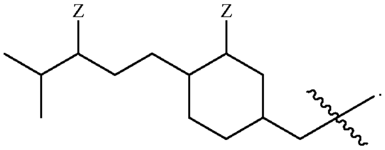

In some aspects, each A segment is:

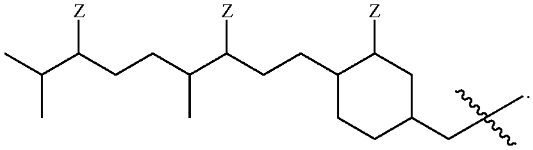

In some aspects, each A segment is:

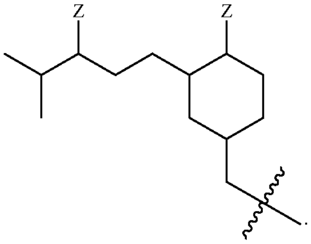

In some aspects, each A segment is:

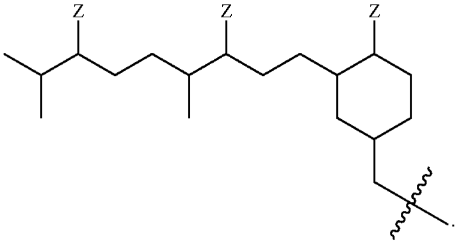

In some aspects, each A segment is:

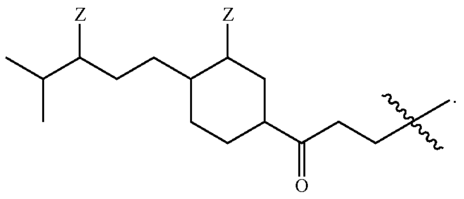

In some aspects, each A segment is:

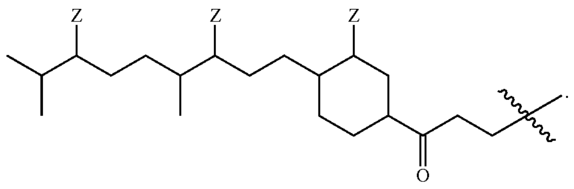

In some aspects, each A segment is:

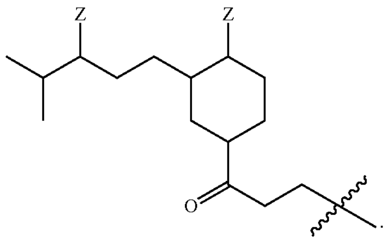

In some aspects, each A segment is:

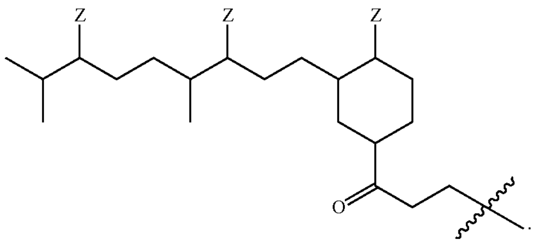

In some aspects, each A segment is:

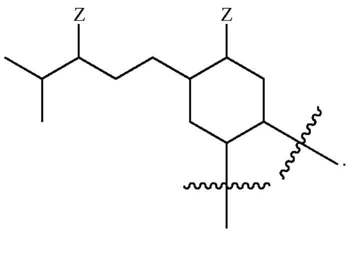

In some aspects, each A segment is:

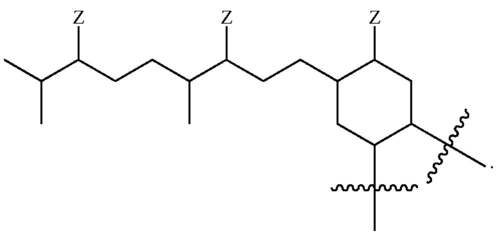

In some aspects, at least one, at least two, or at least three, or at least four or more Z groups of the A segment is —S—$R_1$, wherein $R_1$ is:

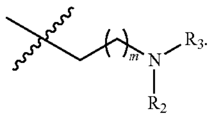

In one such embodiment, m is one and $R_2$, and $R_3$ are each independently $C_1$-$C_6$ alkyl. In one embodiment, each of the $C_1$-$C_6$ alkyl groups is methyl. In this embodiment, 2-(dimethylamino)ethanethiol or 2-(dimethylamino)ethanethiol hydrochloride can be used as the derivatizing agent.

In some aspects, each Z of the A segment is —S—$R_1$, wherein $R_1$ is:

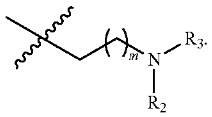

In one such embodiment, m is one and $R_2$, and $R_3$ are each independently $C_1$-$C_6$ alkyl. In one embodiment, each of the $C_1$-$C_6$ alkyl groups is ethyl. In the case where each of the C1-C6 alkyl groups are ethyl, 2-diethylaminoethane thiol or 2-diethylaminoethane thiol hydrochloride can be used as the derivatizing agent.

In some aspects, at least one, at least two, or at least three, or at least four or more Z groups of the A segment is —S—$R_1$, wherein $R_1$ is:

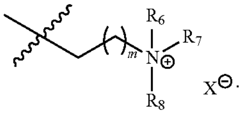

In one such embodiment, m is one and each $R_4$, $R_6$ or $R_7$ is independently $C_1$-$C_6$ alkyl. In one embodiment, each of the $C_1$-$C_6$ alkyl groups is methyl. In one embodiment, X is chlorine or bromine. In one embodiment, X is chlorine. In one embodiment, X is bromine. When X is bromine and C1-C6 is methyl, for example, (2-mercaptoethyl)-N,N,N-trimethylammonium bromide can be used as the derivatizing agent.

In some aspects, each Z of the A segment is —S—$R_1$, wherein $R_1$ is:

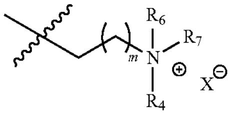

.

In one such embodiment, m is one and each $R_4$, $R_6$ or $R_7$ is independently $C_1$-$C_6$ alkyl. In one embodiment, each of the $C_1$-$C_6$ alkyl groups is methyl. In one embodiment, X is chlorine or bromine. In one embodiment, X is chlorine. In one embodiment, X is bromine.

In some aspects, each Z is —S—$R_1$, wherein at least one, at least two, or at least three, or at least four or more $R_1$ is:

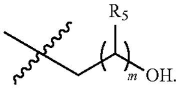

In one embodiment, m is one and $R_5$ is hydrogen. In this embodiment, ethane thiol can be used as the derivatizing agent.

In some aspects, each Z is wherein at least one, at least two, or at least three, or at least four or more $R_1$ is:

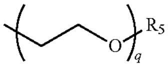

.

In one embodiment, q is one and $R^5$ is methyl.

In some aspects, each B segment is:

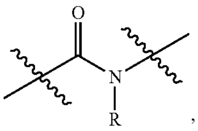

, wherein each R is hydrogen and the carbonyl of the amide of each B segment is attached to each A segment.

In some aspects, each B segment is:

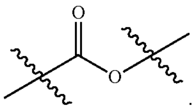 [SMILES: *OC(*)=O]

.

In some aspects, each B segment is:

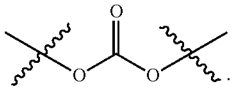 [SMILES: *OC(=O)O*]

.

In some aspects, each B segment is:

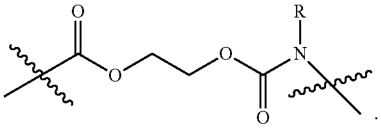

.

In some aspects, the C segment is a C2-C100 hydrocarbon chain. In one embodiment, the C2-C100 hydrocarbon chain is ethylene, propylene, isopropylene, butylene, isobutylene, sec-butylene, tert-butylene, pentylene, hexylene, heptanylene, octanylene, nonanylene, decanylene, undecanylene, dodecanylene, tridecanylene, icosanylene, triacontanylene, and tetracontanylene. In some aspects, the C segment is derived from the corresponding C2-C100 diamine or dialcohol depending on the desired B linkage. In one embodiment, the C segment is a C6 hydrocarbon chain. In one embodiment, the C6 hydrocarbon chain is hexylene. In one embodiment, the C segment is a C12 hydrocarbon chain. In one embodiment, the C12 hydrocarbon chain is dodecanylene. In one embodiment, the C segment is a C20 hydrocarbon chain. In one embodiment, the C20 hydrocarbon chain is icosanylene.

In one embodiment, the C2-C100 hydrocarbon chain can include one or more S atoms. In one aspect, the C2-C100 hydrocarbon chain includes two S atoms.

For example, the C2-C100 hydrocarbon chain may be:

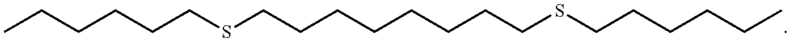 [SMILES: CCCCCCSCCCCCCCCSCCCCCC]

.

In one embodiment, each B segment is:

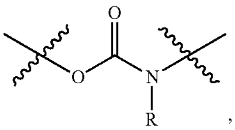

, wherein each R is hydrogen and the oxygen of the carbamate group of each B segment is attached to each A segment.

In one embodiment, the C segment is a C2-C12 hydrocarbon chain derived from well-known diisocyanates such as 1,4-diisocyanatobutane, hexamethylene diisocyanate, 1,8-Diisocyanatooctane, or 1,12-Diisocyanatododecane.

In one embodiment, the C segment is $Cyc^A$-L-$Cyc^B$, wherein $Cyc^A$ and $Cyc^B$ are each independently a 5-8 membered cycloalkyl chain and L is $C_1$-$C_3$ alkylene. In one embodiment, $Cyc^A$ and $Cyc^B$ are each cyclohexyl and L is methylene.

In some aspects, the C segment is a polyalkylene oxide or polyalkylene oxide block or random copolymers of 200-5,000 molecular weight. In one embodiment, the polyalkylene oxide or polyalkylene oxide block copolymers of 200-5,000 molecular weight is, for example, poly(ethylene oxide) or poly(propylene oxide). Suitable random or block copolymers of poly(ethylene oxide) and/or poly(propylene oxide)

include polylactide (PLA) [usually called poly(lactic acid)], polyglycolide (PGA), poly(ε-caprolactone) (PCL), and poly (γ-valerolactone) (PVL).

In some aspects, the C segment is an aliphatic or aromatic polyester of 200-5,000 molecular weight. Aliphatic polyesters have been used as polymers for drug delivery applications due to their biodegradable and biocompatible nature. Suitable aliphatic polyesters of appropriate molecular weight for use as C segment precursors herein include polylactide (PLA) [usually called poly(lactic acid)], polyglycolide (PGA), poly(ε-caprolactone) (PCL), and poly (γ-valerolactone) (PVL).

In addition, a wide variety of aromatic polyesters of desired molecular weight can be used as C segment precursors. Aliphatic-aromatic polyesters can be obtained, for example, by condensing aliphatic diols, aliphatic dicarboxylic acids, and aromatic dicarboxylic acids/esters. The aliphatic-aromatic copolyesters are synthetically polymerized. Well known biodegradable aliphatic-aromatic copolyesters are poly(othylene terephthalate) (PET), poly(butylene succinate-co-terephthalate) (PBST) and, poly(butylene adipate-co-terephthalate) (PBAT). Various representative industrial methods for producing aliphatic-aromatic copolyesters are described in U.S. Pat. No. 5,171,308 A (1992, DU PONT), WO9514740 A1 (1995, DU PONT), WO9625446 A1 (1996, BASF AG), EP1108737 A2 (2001, IRE CHEMICAL LID), and EP1106640 A2 (2001, IRE CHEMICAL LID). In one embodiment, the aliphatic or aromatic polyester of 200-5,000 molecular weight is, for example, PBAT.

In some aspects, the C segment is an aliphatic or aromatic polyurethane of between 200-5,000 molecular weight. Difunctionalized aliphatic diisocyanates can be used in preparation of degradable polyurethanes to circumvent any potential toxicity concerns. Suitable aliphatic diisocyanates for use herein include 1,4-butane diisocyanate, 1,6-hexamethylene diisocyanate, and lysine diisocyanates. Lysine diisocyanate has gained popularity in recent years due to the assumption that its lysine-based chemistry will yield safe carboxylic by-products. Butane diisocyanate also is considered to have biocompatible degradation products, as the hydrolyzed product, putrescine, is naturally occurring in the body.

Commercial aromatic isocyanates for preparing suitable aromatic polyurethanes of desired molecular weight are toluenediisocyanate (TDI), diphenylmethane diisocyanate (MDI), and naphthalene diisocyanate (NDI) and their polymeric forms.

In one embodiment, the aliphatic or aromatic polyurethane of 200-5,000 molecular weight is, for example, polyurethanes derived from biocompatible hydroxyl-terminated diols such as polylactide (PLA) [usually called poly(lactic acid)], polyglycolide (PGA), poly(ε-caprolactone) (PCL), poly(ethyleneterpthalate, poly(ethyleneadipate), and poly(γ-valerolactone) (PVL)), polyether diols combined with diisocyanates such as lysine diisocyanate.

In some aspects, the two B segments and the C segment are:

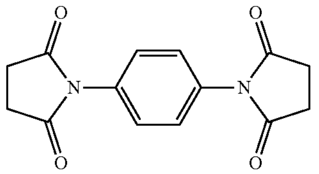 [SMILES: O=C1CCC(=O)N1c1ccc(N2C(=O)CCC2=O)cc1]

wherein each pyrrolidindione is fused to the cyclohexyl group of each A segment to form a bicyclic maleimide ring.

In some aspects, the multivalent cationic bolaamphiphilic compound of Formula (I) is a compound have a formula selected from the following:

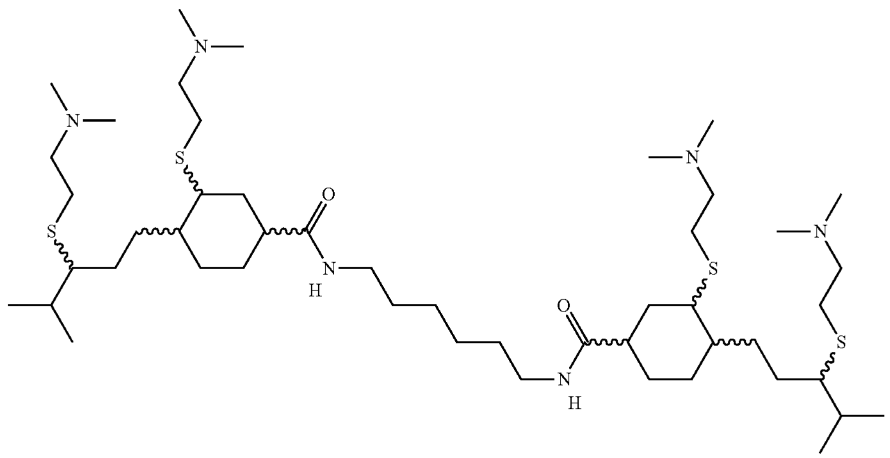

,

-continued
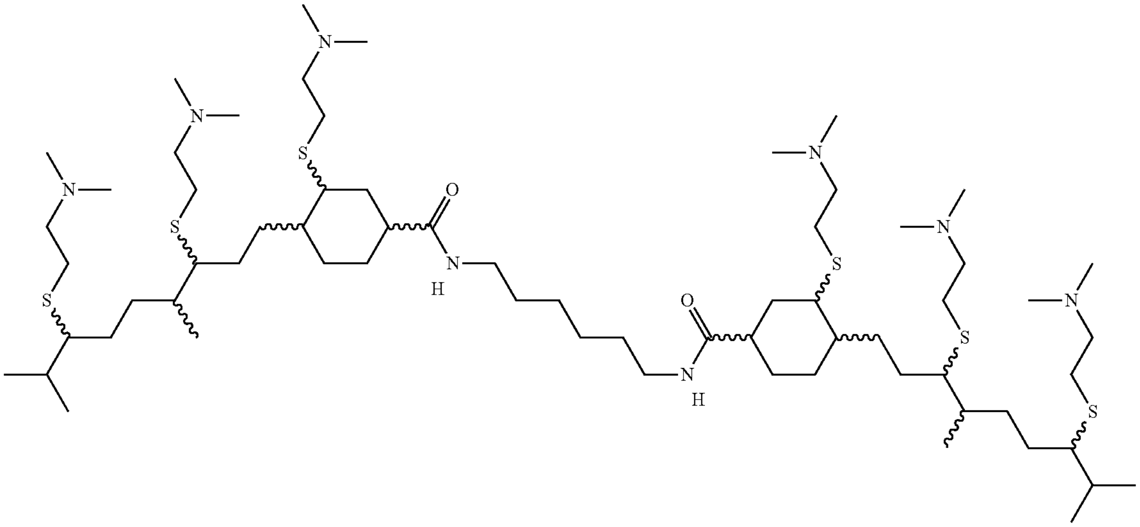
,
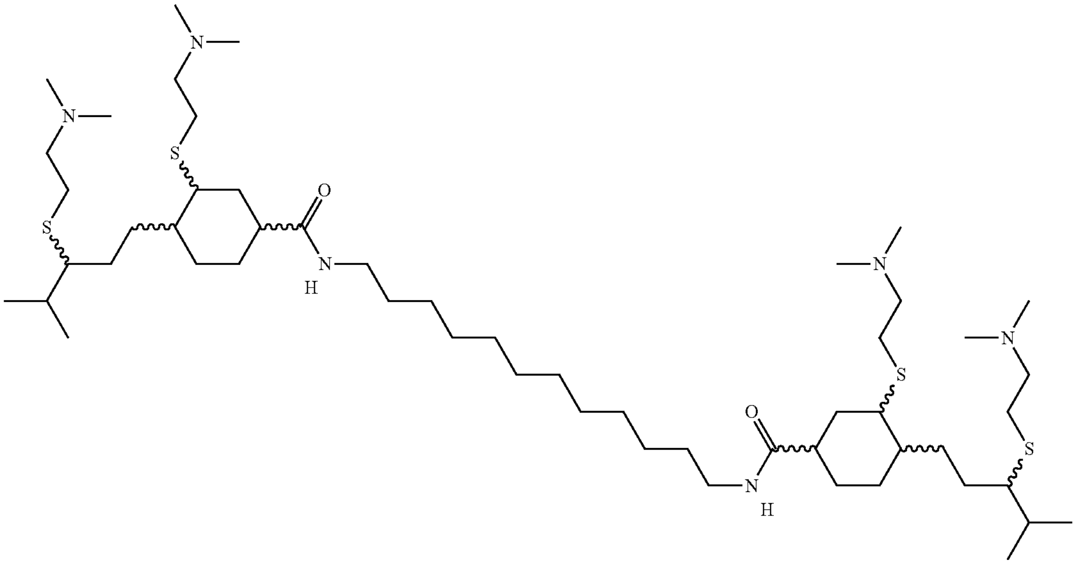
,
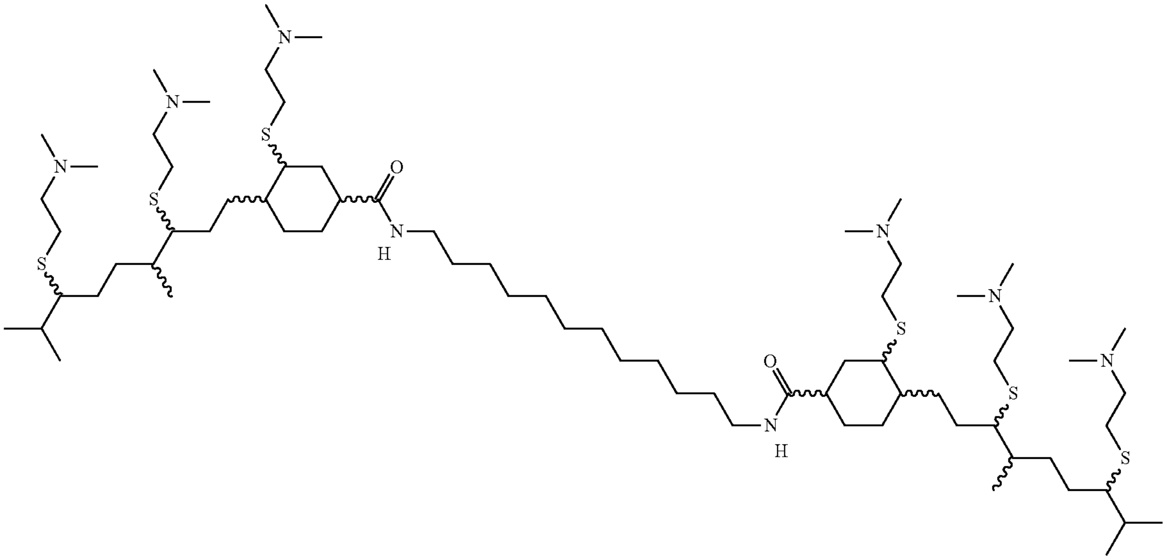
,

-continued
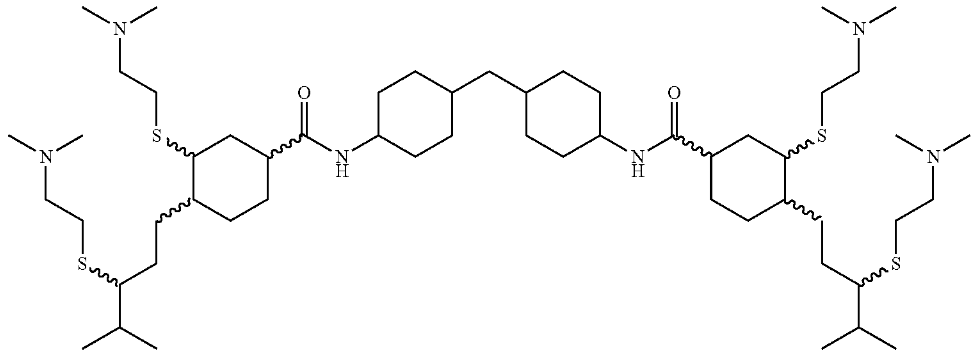
,
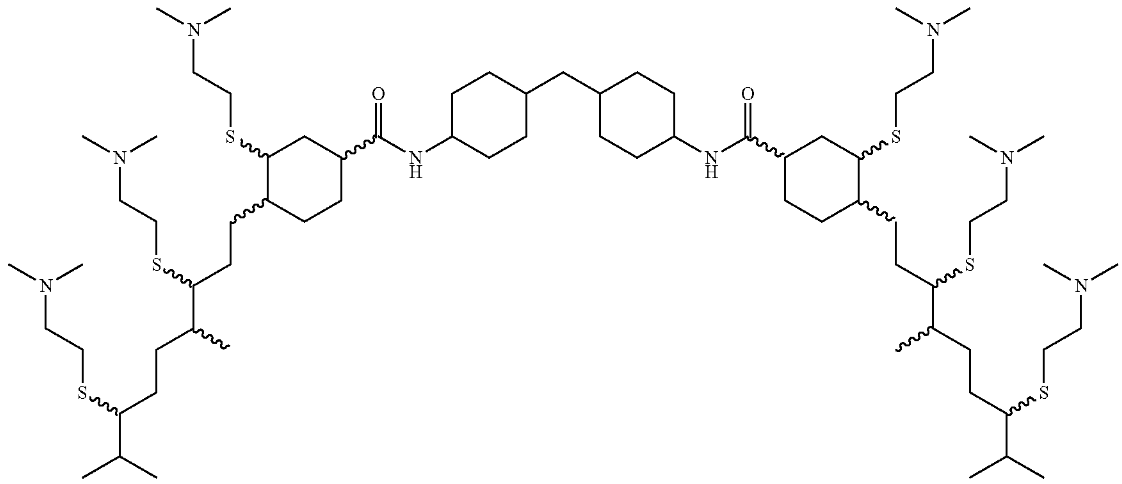
,
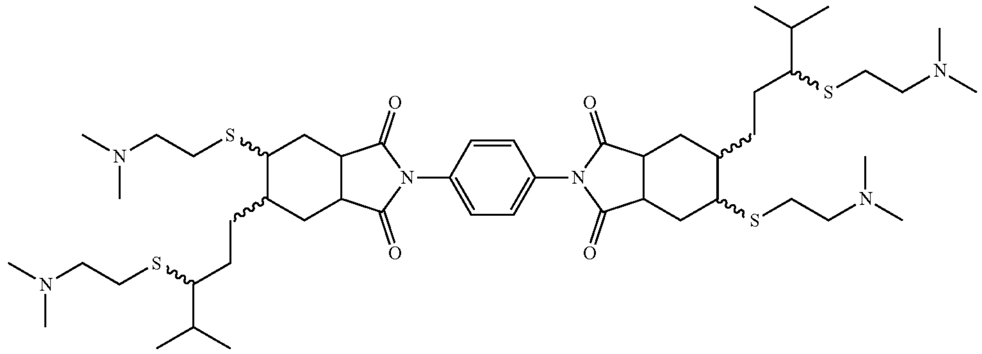
,

-continued
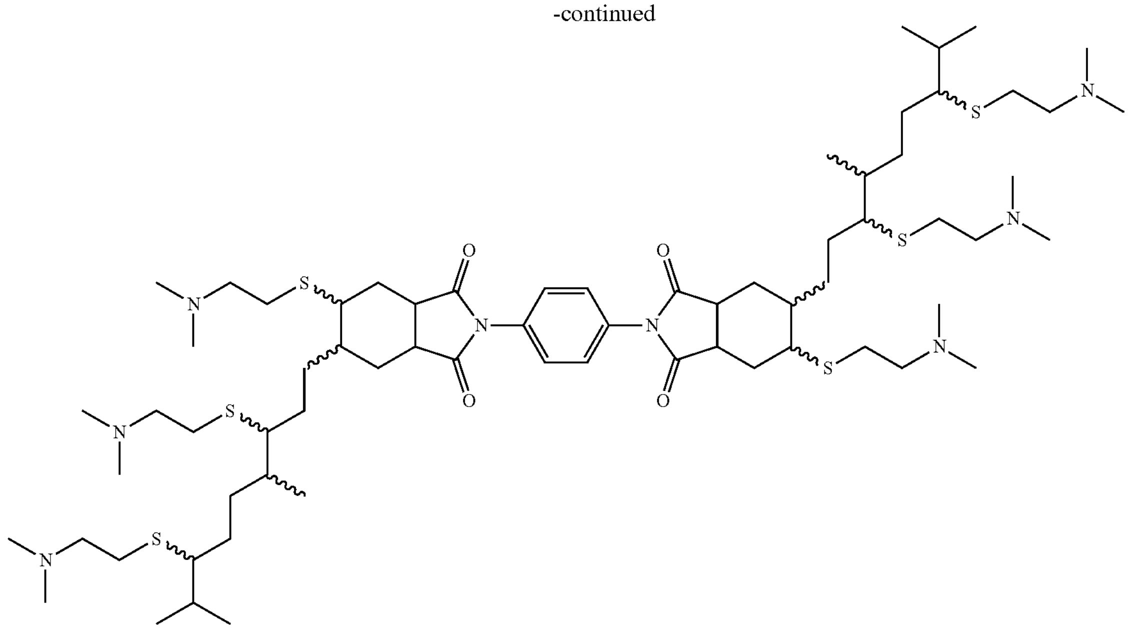
,
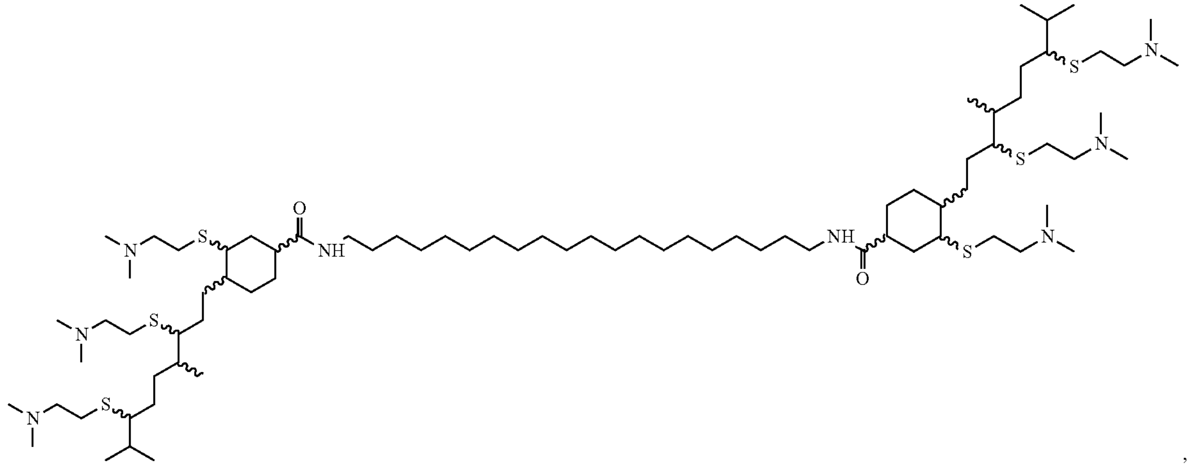
,
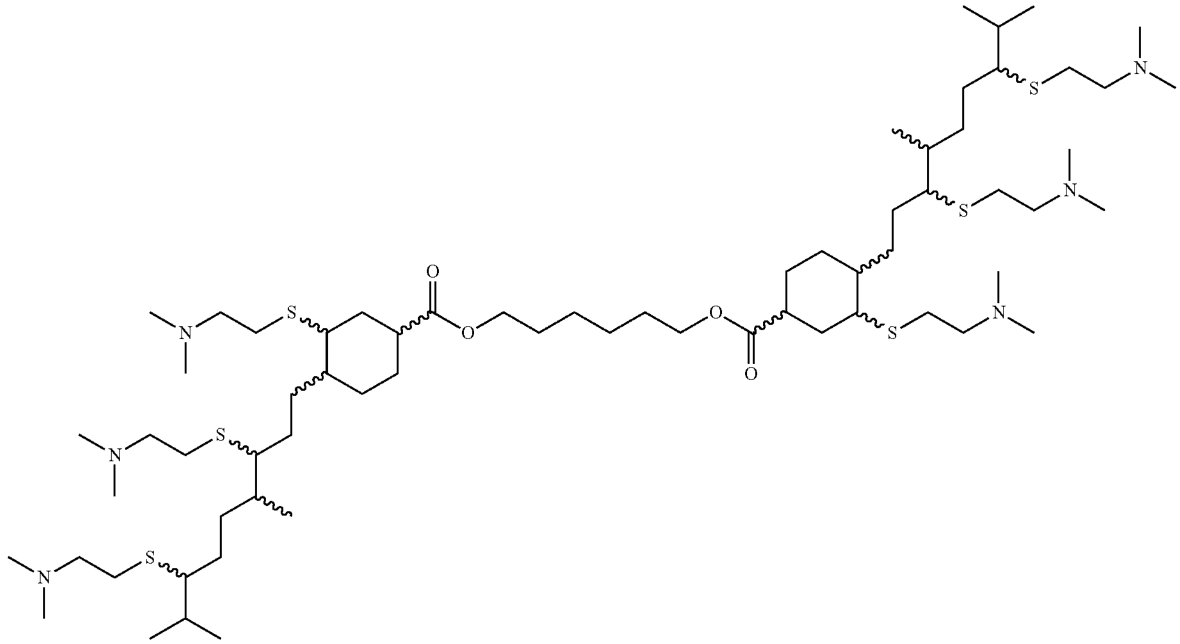
,

-continued
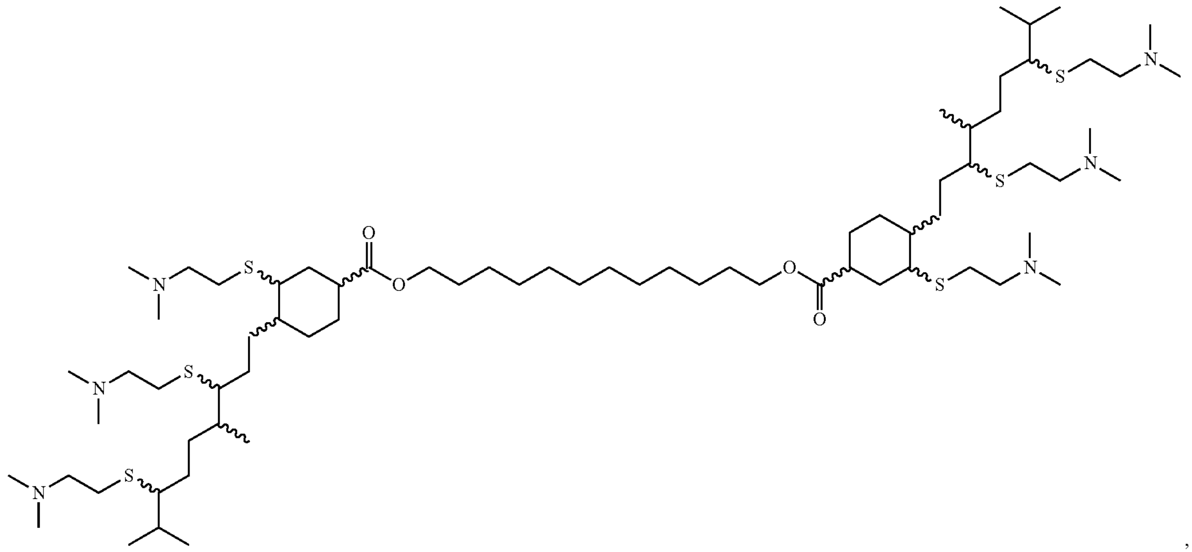
,
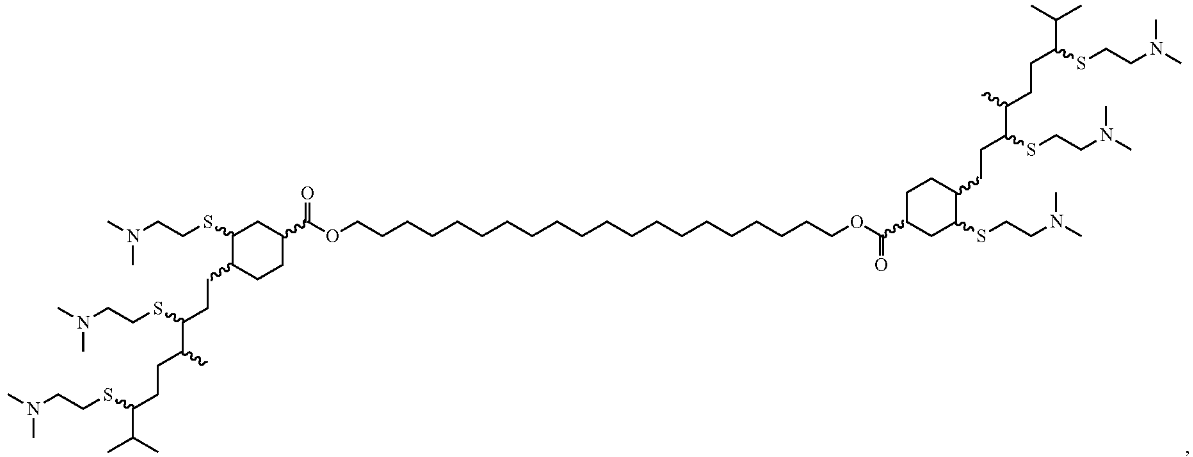
,
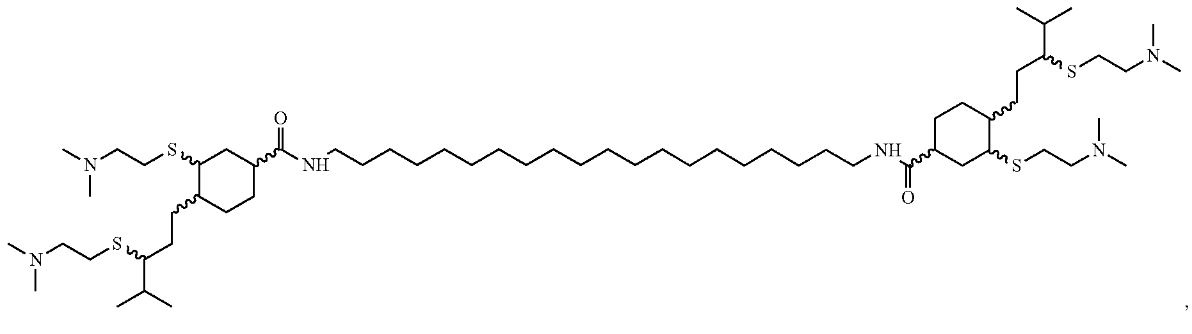
,

-continued
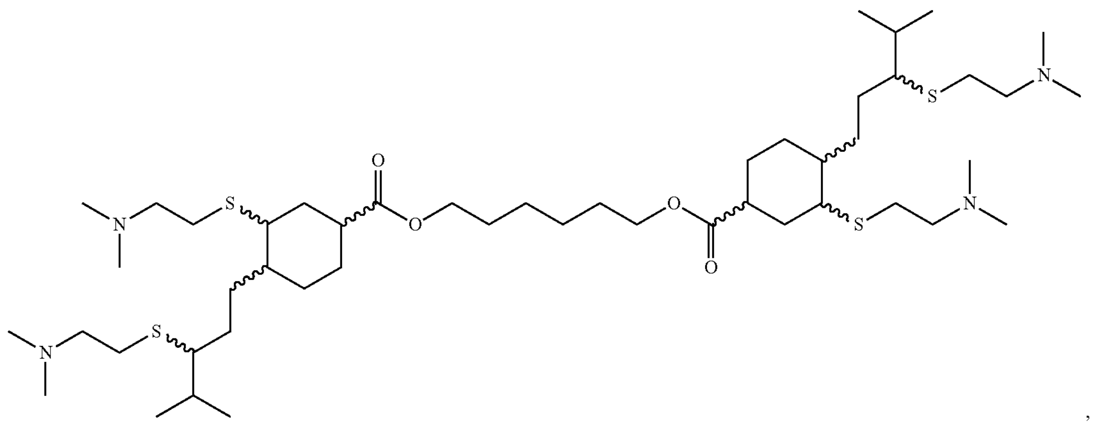
,
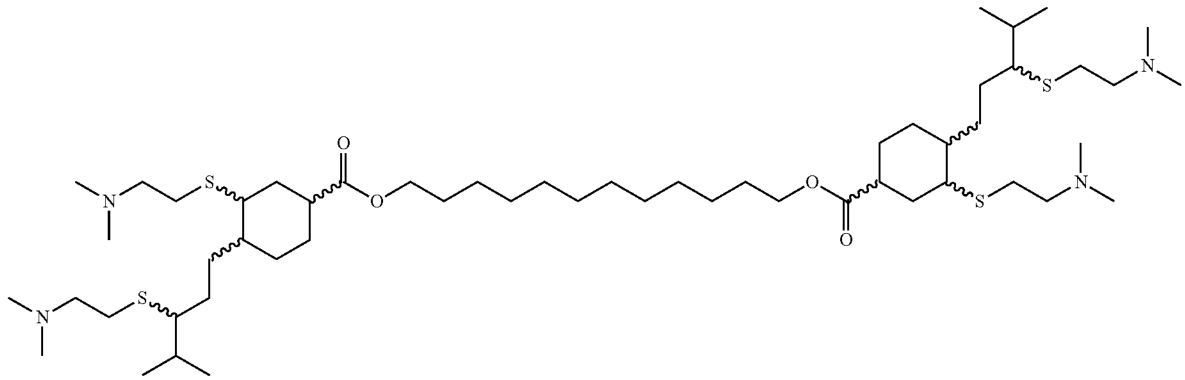
,
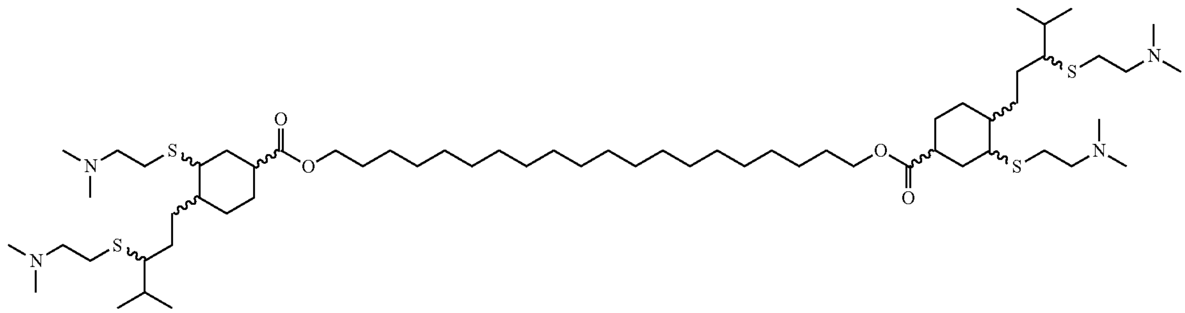
,
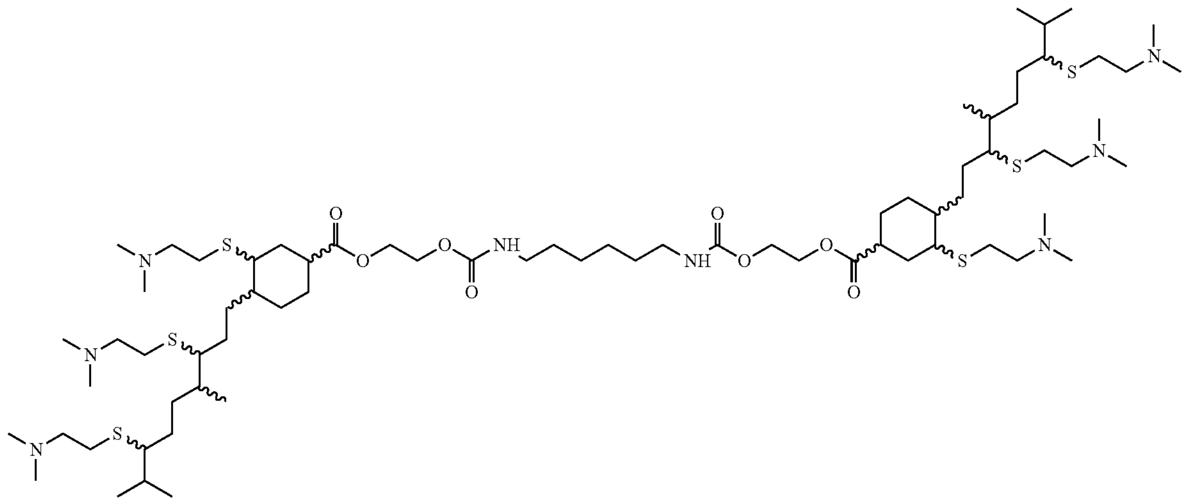
,

-continued
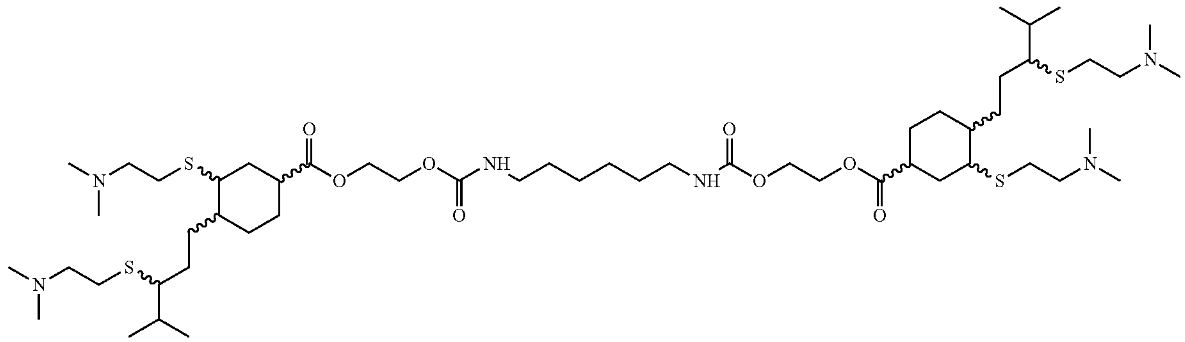
,
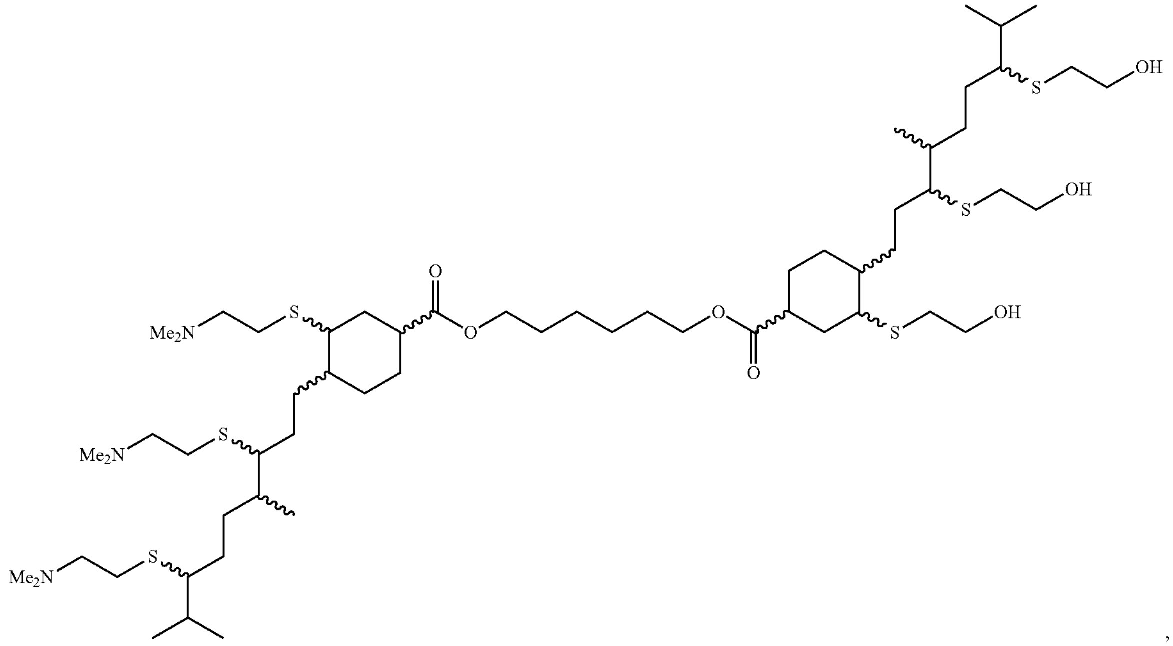
,
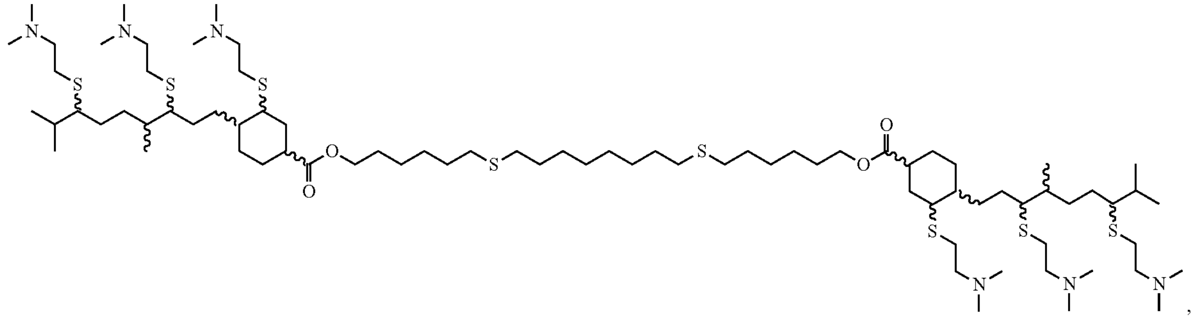
,
and

-continued

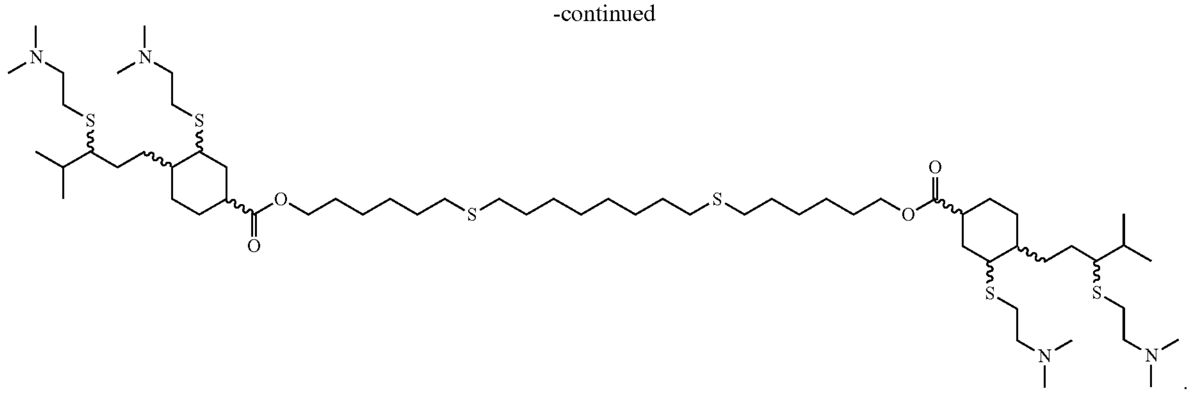

It will be understood that the compounds of any one of the Formulae disclosed herein and any pharmaceutically acceptable salts thereof, comprise stereoisomers, mixtures of stereoisomers, polymorphs of all isomeric forms of said compounds.

It will be understood that while compounds disclosed herein may be presented without specified configuration (e.g., without specified stereochemistry). Such presentation intends to encompass all available isomers, tautomers, regioisomers, and stereoisomers of the compound. In some embodiments, the presentation of a compound herein without specified configuration intends to refer to each of the available isomers, tautomers, regioisomers, and stereoisomers of the compound, or any mixture thereof.

It is to be understood that the compounds of any Formula described herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

It will be understood that in any of the formulae described herein, when a "-" is used to indicate linkage between two variables (e.g., A-B), the linkage could be one or more covalent bonds. For example, in Formula (I) below, the adjacent variables A and B could be linked by one covalent bond, or by more than one (e.g., two) covalent bonds:

(I)

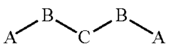

In another example, when variable A is presented as a moiety having two attachment points (e.g.

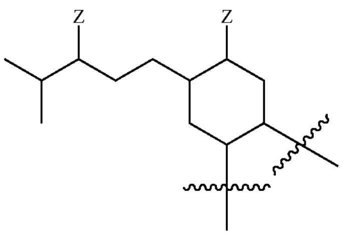

or

-continued

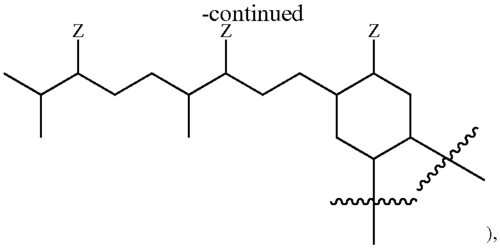

), both of the two attachment points in the variable A could be attached to its adjacent variable B (e.g., when

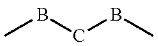

together form

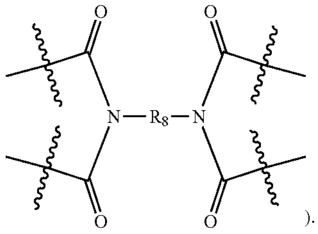

).

General Methods for the Preparation of Compounds of Formula (I) of the Present Disclosure Compounds of Formula (I) can be prepared using the reagents, intermediates, precursors and methods disclosed herein or using other commercially available reagents and methods known to those skilled in the art.

In general, the first step in preparation of multivalent cationic bolaamphiphilic compounds of Formula (I) of the present disclosure is the selection of an appropriate terpene, e.g., trans-beta-farnesene, beta-myrcene or other suitable biorenewable terpene, to prepare the multivalent "A" segment precursor. For example, trans-beta-farnesene can be reacted with a suitable unsaturated carboxylic acid derivative, e.g., ethyl acrylate, which serves as a dieneophile forming a suitable Diels-Alder adduct:

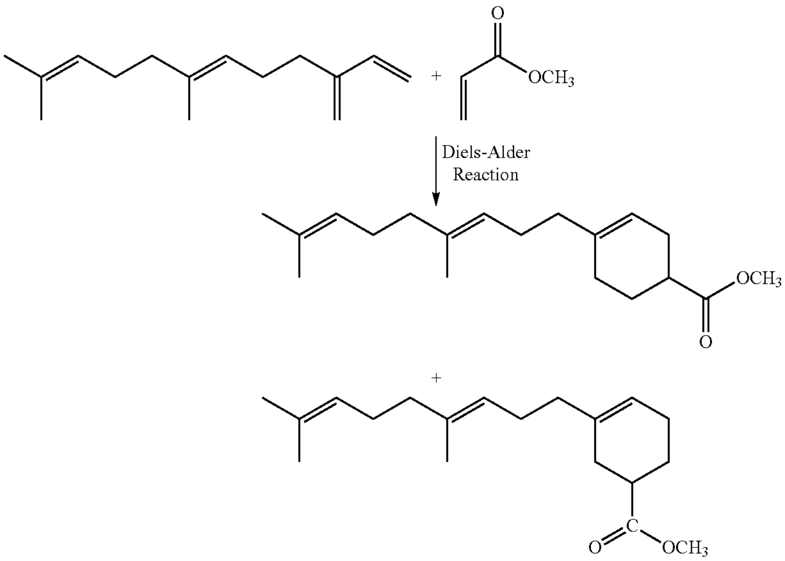

Suitable Diels-Alder products for use in the methods herein include:

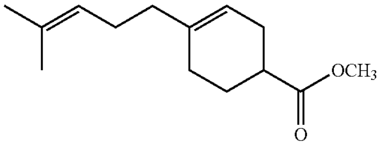

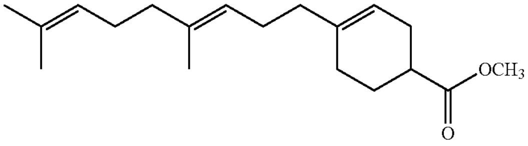

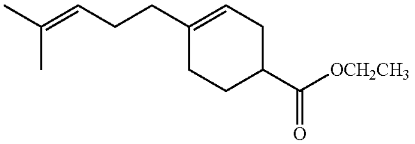

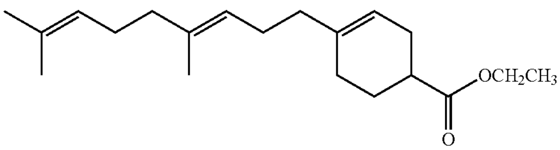

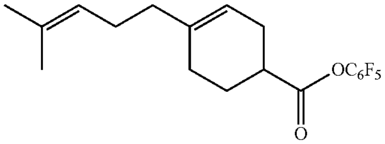

-continued

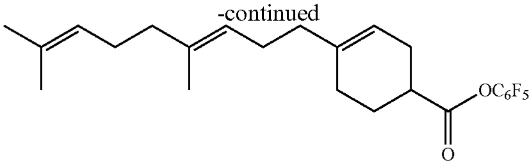

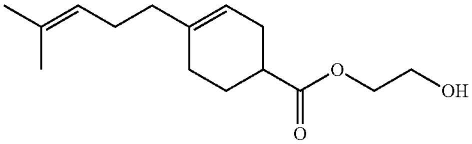

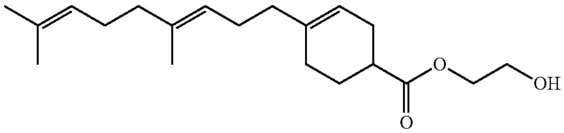

In general, the Diels-Alder product, the "A" segment precursor, can be added to a heavy walled vial along with the selected diamine (1 molar equivalent) and a stir bar. 1,5,6-triazabicyclo[4.4.0]dec-5-ene (TBD) can then be added (20 mol % based on the terpene Diels-Alder adduct) and the reaction heated to 130° C. for 15 h. Upon cooling to room temperature, the reaction product will solidify into a tan semi-solid. The solid can then be first washed with multiple portions of hexanes (to remove excess terpene), water (to remove catalyst and unreacted diamine), and finally isolated by filtration. After drying under vacuum the isolated yields are >90%.

In one instance, the "A" segment precursor, is reacted with a suitable difunctional nucleophile "C" segment precursor, e.g., C2-C100 hydrocarbon chain functionalized with an amine at each end position of the chain, wherein nucleophilic substitution reaction described above at each position links the two "A" segment precursors to the "C" segment precursor while simultaneously forming the two "B" segments:

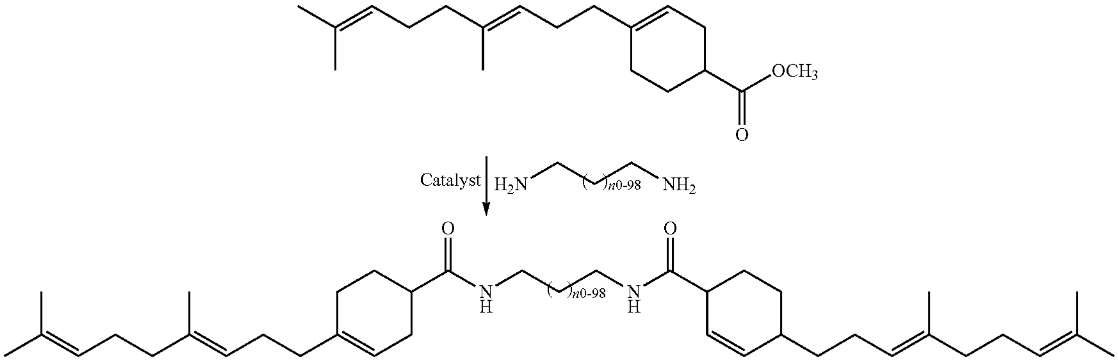

Similarly, in another instance, the "A" segment precursor, is reacted with a suitable difunctional nucleophile "C" segment precursor, e.g., C2-C100 hydrocarbon chain functionalized with a diol at each end position of the chain, wherein nucleophilic substitution reaction described above at each position links the two "A" segment precursors to the "C" segment precursor while simultaneously forming the two "B" segments:

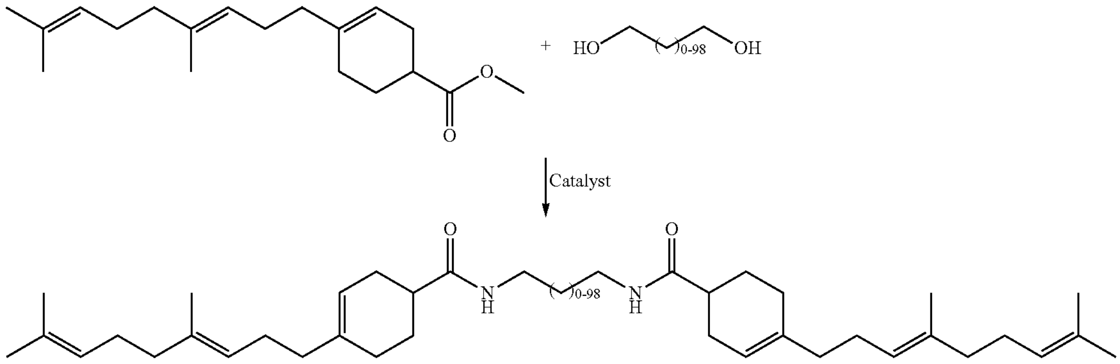

The compounds of Formula (I) are prepared by the addition of "Z" to the assembled A-B-C-B-A precursor using a suitable $R_1$ group thiol precursors, e.g., amine, hydroxyl, or poly(alkeneoxide) functional thiols, individually or as mixtures, by photochemical or thermal means.

For instance, compounds of Formula (I) can be prepared by reacting the A-B-C-B-A precursor above with a suitable photochemical thiol, e.g., 1-(dimethylamino)ethanethiol hydrochloride, in the presence 2,2-dimethoxy-2-phenylacetophenone, and irradiating at room temperature with 370 nm light from OLED lights positioned at both sides at an appropriate distance, e.g., 5 cm or 14 cm, for a defined period, e.g., 12 hr or 4 hrs, respectively. The chloroform-methanol solution is then evaporated and the resulting yellow solid washed with ethyl acetate before being redissolved in a minimal amount of water. The aqueous solution can then be dialyzed (100-500 D molecular weight cut off cellulose ester) against deionized water. The water is changed twice (4 hour intervals) and then left overnight. The final product can be isolated by lyophilization affording compounds of Formula (I).

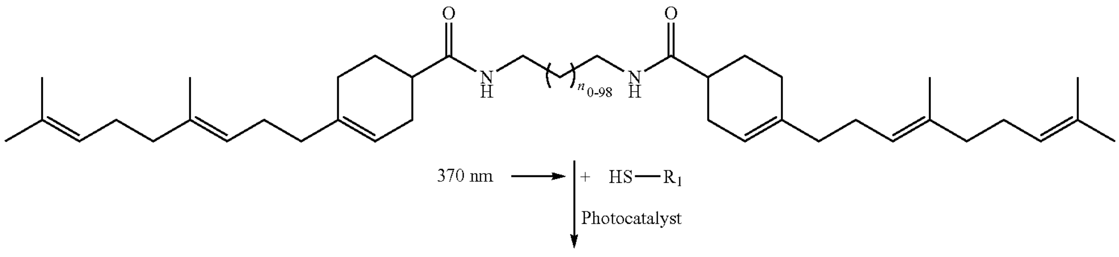

-continued

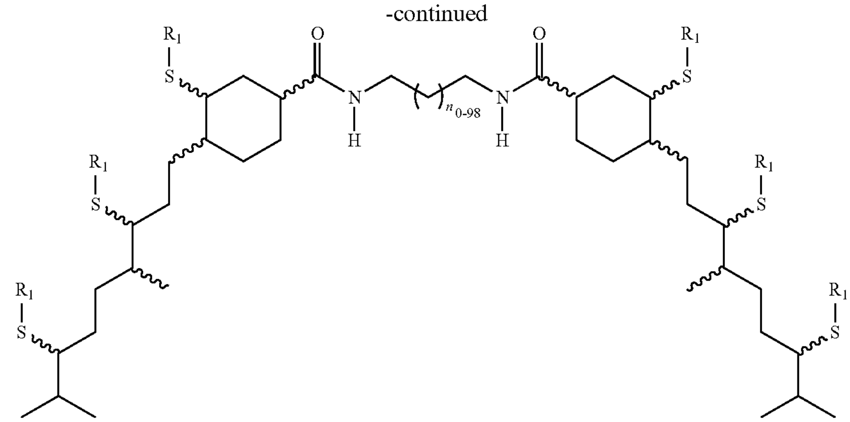

Alternatively, compounds of Formula (I) can be prepared by first coupling Z to the A chain precursor. In one embodiment, the methyl esters of trans-beta-farnesene can be subject to similar conditions above to generate A precursors preloaded with one or more Z (i.e., —SH—$R_1$) groups which is then coupled to the C precursors using methods analogous to those described above.

In another aspect, compounds of Formula (I) can be prepared by linear polymerization using bis-maleimides by Michael addition. The maleimide carbon-carbon double bond is highly electrophilic and can react with nucleophilic reagents, such as amines or thiol derivatives of the A segment, to afford compounds of Formula (I).

In another aspect, compounds of Formula (I) can be prepared as shown in Scheme 1.

Scheme 1

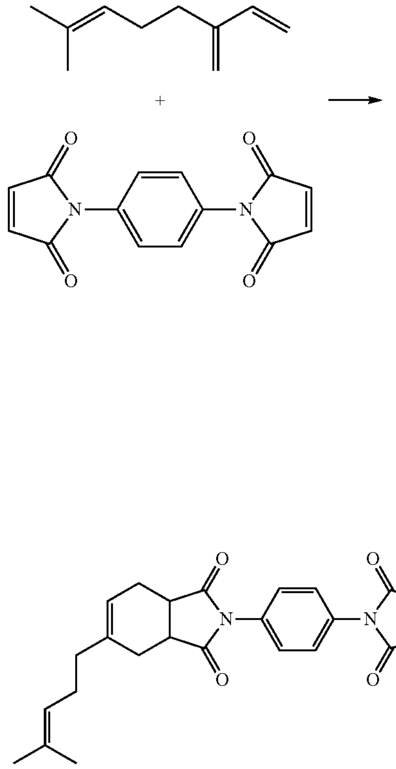

-continued

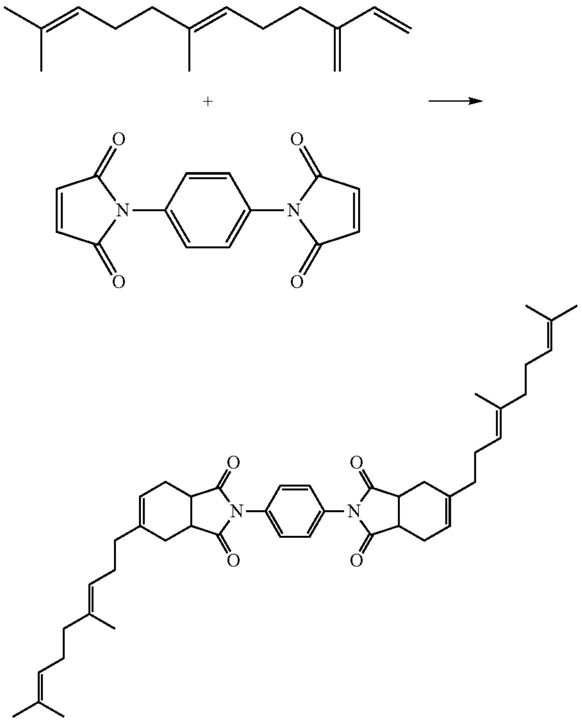

Farnesene or myrcene (3 molar equivalents) is added to a heavy walled vial along with N,N'-(1,4-phenylene)dimaleimide (1 molar equivalent). The vial is sealed and heated to 130° C. Within 30 minutes the reaction will solidify yielding the crude product. The crude solid is removed from the reaction vessel, suspended in hexanes, and stirred. The mixture is subjected to centrifugation and the hexane supernatant decanted away from the product. The product is dried in a vacuum oven at 40° C.

The compounds of Formula (I) can be prepared by the addition of "Z" to the assembled A-B-C-B-A precursor using a suitable $R_1$ group thiol precursor, e.g., amine, hydroxyl, or poly(alkeneoxide) functional thiol, individually or as mixtures, by photochemical or thermal means.

In one embodiment, the suitable $R_1$ group thiol precursor is 2-(dimethylamino)ethanethiol hydrochloride.

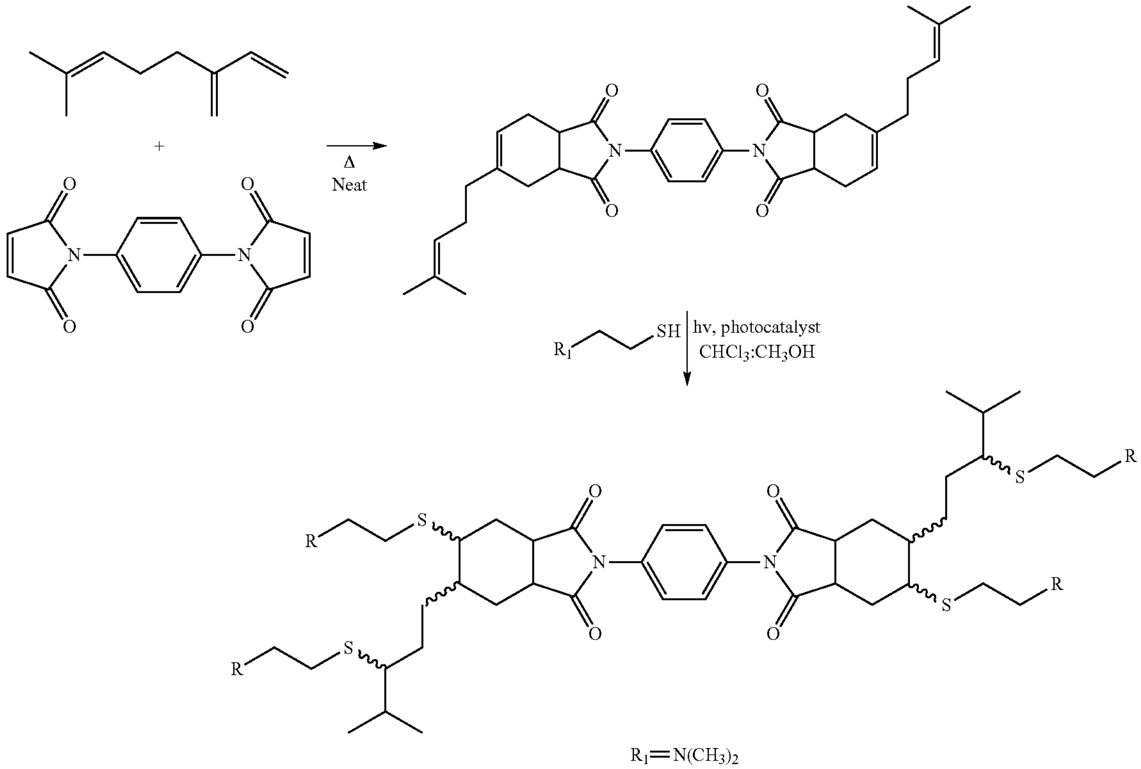

In yet another embodiment, compounds of the invention may be prepared as follows.

First, a bola base was prepared by the following general protocol:

A. General Protocol For Bolabase Preparation

In a 4 mL sealable glass tube, methyl ester (farnesene methyl ester (FME) or myrcene methyl ester (MME)) (4.0 eq) was added with the diamine or diol (1.0 eq) and a catalyst TBD (0.8 eq). The tube was sealed and stirred at 130° C. for 20 h (diamide series) or 48 h (diester series) without any solvent, except for $C_{20}$-diol and $C_{26}$-diol in which case 0.5 mL of DMSO was added for diol solubility. The reaction was cooled and purified by flash silica gel chromatography. In the case of $C_{20}$-diol and $C_{26}$-diol, the reaction mixture was added water and extracted with EtOAc (3×). All the EtOAc extracts were combined, washed with brine (3×), dried over $Na_2SO_4$, and evaporated. The crude was then purified by flash silica gel chromatography.

Purification Conditions

Amide series:

Compound 1: Silica gel column chromatography with 20-50% EtOAc:hexanes

Compound 2: Recrystallization with ethanol

Ester series:

Compounds 5, 6, 13, & 14: Silica gel column chromatography with 5% EtOAc:hexanes Compounds 7, 8, & 15: Silica gel column chromatography with 50% toluene: hexanes B. General Protocol for Bolaamphiphiles Preparation Once the bola base was prepared, the bola base was used to make the final compounds as follows.

In a 4 mL quartz tube, bola base (1.0 eq), thiol (1.5 eq per alkene), and photocatalyst, 2,2-Dimethoxy-2-phenylacetophenone (DMPA) (0.2 eq per alkene) were taken. A mixed solvent system of THF:MeOH (5:1) was added until all the reagents were dissolved and degassed with nitrogen for 10 mins before irradiating with 350 nm of UV light for 6 h at room temperature. The solvent was evaporated and the residue was passed through a silica gel column. Eluant 5% MeOH:DCM was used to remove nonpolar impurities and the compound was isolated with 10-50% MeOH:DCM. The off-white solid obtained was dissolved in a few mL of DI water and dialyzed against water in 100-500 daltons bag for 20 h. The dialyzed solution was lyophilized to get the bolaamphiphiles as off-white hygroscopic solids.

The compounds of Formula (I) can be incorporated into pharmaceutical compositions.

Pharmaceutical Compositions

The present disclosure provides pharmaceutical compositions and methods for administration of the compounds of Formula (I) described herein.

The disclosed compositions and pharmaceutical compositions can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of such auxiliaries and methods of preparing sterile solutions of the present compositions are well known in the art, such as from (but not limited to) Gennaro, Ed., Remington's Pharmaceutical Sciences, 18th Edition, Mack Publishing Co. (Easton, Pa.) 1990 and the "Physician's Desk Reference", 52nd ed., Medical Economics (Montvale, N.J.) 1998. Pharmaceutically acceptable carriers can be routinely selected that are suitable for the mode of administration, solubility and/or stability of the protein scaffold, fragment or variant composition as well known in the art or as described herein.

The compositions can also include a buffer or a pH-adjusting agent.

Many known and developed modes can be used for administering therapeutically effective amounts of the compositions or pharmaceutical compositions disclosed herein. Non-limiting examples of modes of administration include bolus, buccal, infusion, intrarticular, intrabronchial, intraabdominal, intracapsular, intracartilaginous, intracavitary, intracelial, intracerebellar, intracerebroventricular, intracolic, intracervical, intragastric, intrahepatic, intralesional, intramuscular, intramyocardial, intranasal, intraocular, intraosseous, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intratumoral, intravenous, intra-arterial, intravesical, oral, parenteral, rectal, sublingual, subcutaneous, transdermal or vaginal means.

It can be desirable to deliver the disclosed compounds to a subject over prolonged periods of time, for example, for periods of one week to one year from a single administration. Various slow release, depot or implant dosage forms can be utilized.

Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000); Nursing 2001 Handbook of Drugs, 21st edition, Springhouse Corp., Springhouse, Pa., 2001; Health Professional's Drug Guide 2001, ed., Shannon, Wilson, Stang, Prentice-Hall, Inc, Upper Saddle River, N.J.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably, 0.1 to 10 milligrams per kilogram per administration or in sustained release form is effective to obtain desired results.

As a non-limiting example, treatment of humans or animals can be provided as a one-time or periodic dosage of the compositions or pharmaceutical compositions disclosed herein from about 0.1 to 100 mg/kg or any range, value or fraction thereof per day, on at least one of day 1-40 of a treatment, or, alternatively or additionally, at least one of week 1-52 of treatment, using single, infusion or repeated doses. Alternatively or additionally, treatments can be provided for between 1-20 years, or any combination thereof.

A more detailed description of pharmaceutically acceptable excipients, formulations, dosages and methods of administration of the disclosed compositions and pharmaceutical compositions is disclosed in PCT Publication No. WO 2019/04981.

In an aspect, administration of the present compositions is systemic. Systemic administration can be any means known in the art and/or as described in detail herein. Preferably, systemic administration is by an intravenous injection or an intravenous infusion. In one aspect, the administration is local. Local administration can be any means known in the art and/or as described in detail herein. Preferably, local administration is by intra-tumoral injection or infusion, intraspinal injection or infusion, intracerebroventricular injection or infusion, intraocular injection or infusion, or intraosseous injection or infusion.

In some aspects, the therapeutically effective dose is a single dose. In some aspects, the single dose is one of at least 2, 5, 10, 15, 20, 25, 30, 35, 40, 45, 50, 55, 60, 65, 70, 75, 80, 85, 90, 95, 100 or any number of doses in between that are manufactured simultaneously.

Methods of Use

The multivalent cationic bolaamphiphilic compositions of the present disclosure can be used for gene delivery. The present compositions are bolaamphiphiles, and like other bolaamphiphilic compositions can be used in applications for which surfactants are needed or desired.

The disclosure provides a method for delivering a nucleic acid to a cell, tissue, organ, animal or subject. For example, provided are methods of using a compound of Formula (I) complexed with DNA or RNA, or pharmaceutical compositions thereof, for delivery of RNA or DNA to a cell, tissue, organ, animal, or subject, as known in the art or as described herein, using the disclosed compositions and pharmaceutical compositions, e.g., administering or contacting the cell, tissue, organ, animal, or subject with an amount, e.g., a therapeutically effective amount, of the composition or pharmaceutical composition. In an aspect, the subject is a mammal. Preferably, the subject is human. The terms "subject" and "patient" are used interchangeably herein.

Any method can comprise administering an effective amount of any composition or pharmaceutical composition disclosed herein to a cell, tissue, organ, animal or subject in need of such modulation, treatment or therapy. Such a method can optionally further comprise co-administration or combination therapy for treating such diseases or disorders, wherein the administering of any composition or pharmaceutical composition disclosed herein, further comprises administering, before concurrently, and/or after, at least one other agent.

Lipoplex nanoparticles comprising a compound of Formula (I) and a nucleic acid, e.g., DNA or RNA, can be used for gene delivery following general methods disclosed for monopolar bolaamphiphilic lipids (e.g., see Martin et al., (2005) Current Pharmaceutical Design 11:375-394).

EXAMPLES

Example 1—Preparation of Multivalent Cationic Bolaamphiphilic Compositions by Photochemical Thiol-Ene Reaction

COMPOUND 1

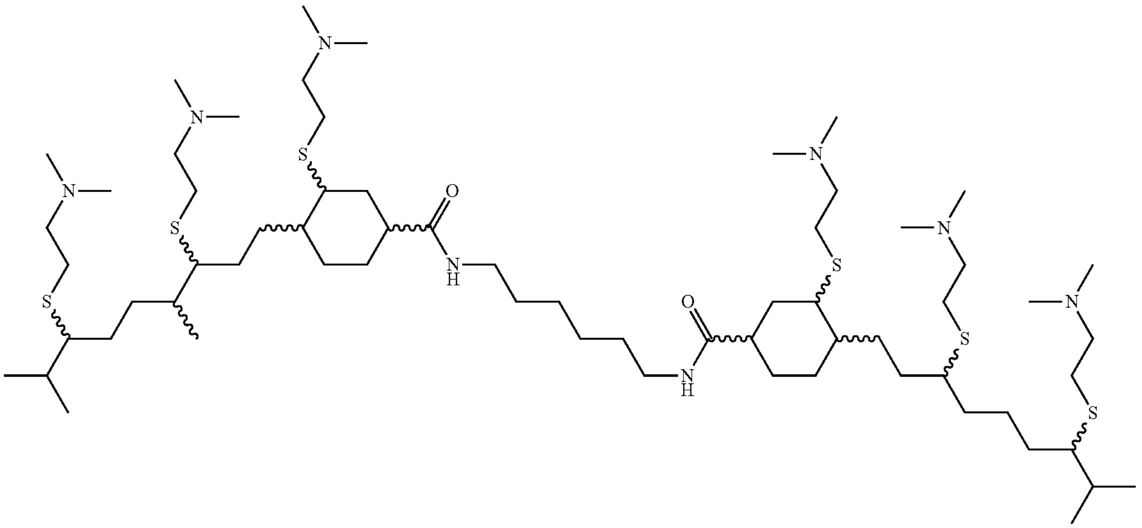

N,N'-(hexane-1,6-diyl)bis(3-(2,6-bis((2-(dimethylamino)ethyl)thio)-3,7-dimethyloctyl)-5-((2-(dimethylamino)ethyl)thio)cyclohexane-1-carboxamide)

This compound was prepared two separate ways.

Synthesis 1 a. Preparation of Methyl Ester Diels-Alder Adduct from Trans-β-Farnesene and Methyl Acrylate To a 20 mL sealable vessel was added trans-β-farnesene (1.00 g, 4.89 mmol), 0.5 wt % (relative to farnesene) p-methoxyphenol (0.005 g, 0.02 mmol), methyl acrylate (0.42 g, 4.98 mmol), and a stir bar. The mixture was heated at 130° C. for 4 h and then cooled to room temperature. The resulting oil was chromatographed on silica gel (95:5 hexanes/ethyl acetate) to give a colorless oil. The isolated product was a mixture of both meta- and para-Diels-Alder regioisomers (0.78 g, 55% yield). $C_{19}H_{30}O_2$ $^1$H NMR (500 MHz, CDCl3) δ: 5.40 (s, CHCR2, 1H), 5.10 (s, CHCR2, 2H), 3.69 (s, C(O)OCH3, 3H), 2.51 (m, CHR2, 1H), 2.24 (m, aliphatic, 1H), 2.02 (m, aliphatic, 12H), 1.68 (s, CH3, 3H), 1.60 (s, (CH3)2, 6H). 13C NMR (500 MHz, CDCl3) δ: 176.4 (C(O)OCH3), 137.4, 136.0, 135.1, 131.2, 124.4, 124.0, 120.3, 118.9, 51.5 (C(O)OCH3), 47.5, 39.8, 39.7, 39.4, 37.7, 37.5, 30.7, 27.7, 26.7, 26.3, 25.7, 25.6, 25.1, 24.6.

b. Preparation of Multivalent Cationic Bolaamphiphile Precursor

The Diels-Alder adduct of methyl acrylate and trans-β-farnesene (10 g, 34 mmol) was added to an 8 mL vessel along with hexamethylenediamine (1.34 g, 11.5 mmol) and a stir bar. The reaction was heated to 130° C. and TBD (0.96 g, 6.9 mmol) was added. Heating was continued overnight. Upon cooling, the reaction solidified into a tan solid. The solid was washed rigorously with hexanes and water and before isolating by filtration (7.28 g, 99% isolated yield). $C_{42}H_{68}N_2O_2$ $^1$H NMR (500 MHz, $CDCl_3$) δ: 5.80 (s, —$NHR_2$, 2H) 5.39 (s, —CH═$CR_2$, 2H), 5.09 (s, —CH═$CR_2$, 4H), 3.23 (s, —$CH_2$—NHR, 4H), 2.64 (s, —CO—$CHR_2$, 2H), 2.19 (m, aliphatic, 24H), 1.67 (s, —$CH_3$, 6H), 1.59 (s, —$(CH_3)_2$, 12H), 1.49 (s, —NCH—$CH_2$R, 4H), 1.32 (s, —$CH_2CH_2$R, 4H).

c. Preparation of Multivalent Cationic Bolaamphiphilic Compound of Formula (I) Using a Photochemical Thiol-Ene Reaction In a 4 mL sealable vessel, 2-(dimethylamino)ethanthiol hydrochloride (453 mg, 3.2 mmol) was dissolved in 0.12 mL methanol and 1.88 mL chloroform. Compound from step b above (200 mg, 0.32 mmol) was added along with 20 mol % 2,4-diethyl-9H-thioxanthen-9-one relative to the thiol (172 mg, 0.64 mmol) along with a stir bar. The solution was stirred at room temperature and irradiated using two 370 nm light emitting diodes from 5 cm away for 4 hours. The chloroform-methanol solution was removed by rotary evaporation and the resulting yellow solid was washed using three portions of ethyl acetate. The washed solid was redissolved in 6 mL water, placed in 100-500 D molecular weight cut off cellulose ester tubing and dialyzed against deionized water. The water was changed twice in the first 8 hours before being left overnight. The final product was isolated by lyophilization as a light yellow solid (220 mg). $C_{66}H_{134}N_8O_2S_6$ $^1$H NMR (500 MHz, $d_6$-DMSO) δ: 3.16 (s (br)), 2.99 (br), 2.73 (s), 2.22-1.18 (m (br)), 0.95 (s), 0.89 (s).

Synthesis 2

First, bola base was prepared according to Protocol A. The bola base has the following structure:

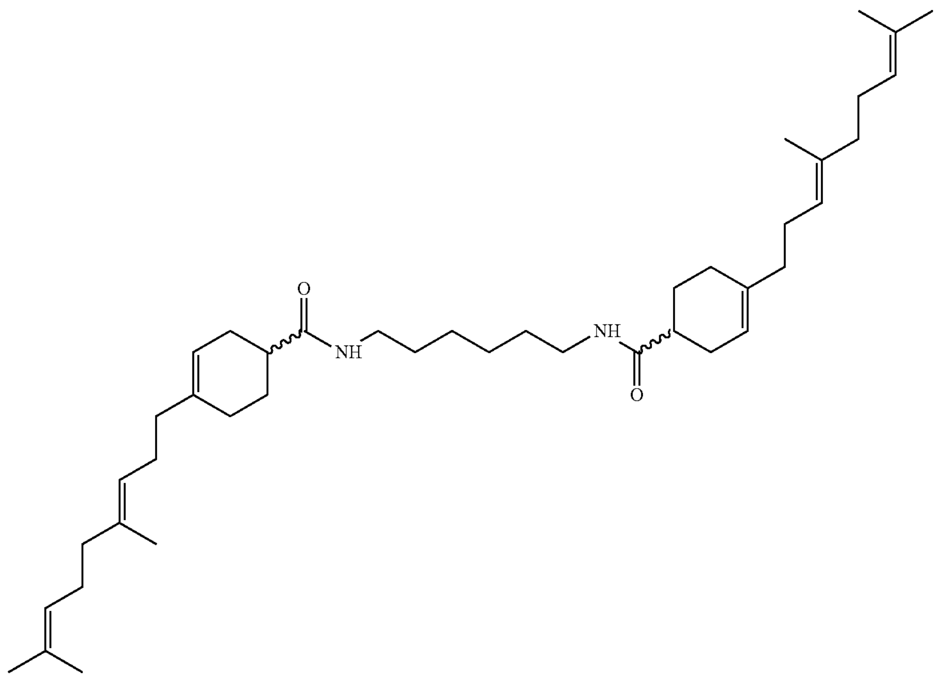 [SMILES: CC(C)=CCC/C(C)=C/CCC1=CCC(C(=O)NCCCCCCNC(=O)C2CC=C(CC/C=C(\C)CCC=C(C)C)CC2)CC1]
The results were:
74% yield, off-white solid. $^{1}$H NMR (400 MHz, CDCl3) δ 5.91 (p, J=6.5, 5.7 Hz, 2H), 5.43-5.32 (m, 2H), 5.16-4.98 (m, 4H), 3.27-3.16 (m, 4H), 2.39-1.78 (m, 28H), 1.74-1.53 (m, 18H), 1.48 (d, J=7.7 Hz, 5H), 1.30 (tt, J=7.7, 3.8 Hz, 5H). 13C NMR (101 MHz, CDCl3) δ 176.25, 176.24, 137.61, 136.30, 135.24, 135.21, 131.38, 124.37, 124.08, 124.05, 120.35, 119.10, 41.96, 41.49, 39.79, 38.87, 38.84, 37.82, 37.62, 31.43, 29.60, 29.59, 28.46, 27.92, 26.79, 26.36, 26.29, 26.00, 25.98, 25.96, 25.80, 24.83, 17.79, 16.12, 16.09.
Then, Protocol B was followed. The results were:
1H NMR (500 MHz, DMSO-d6) δ 3.38-3.30 (m, 8H), 3.24-3.10 (m, 22H), 2.86-2.70 (m, 62H), 1.94-1.84 (m, 2H), 1.78-1.54 (m, 8H), 1.41-1.14 (m, 16H), 1.00-0.57 (m, 18H).
COMPOUND 2
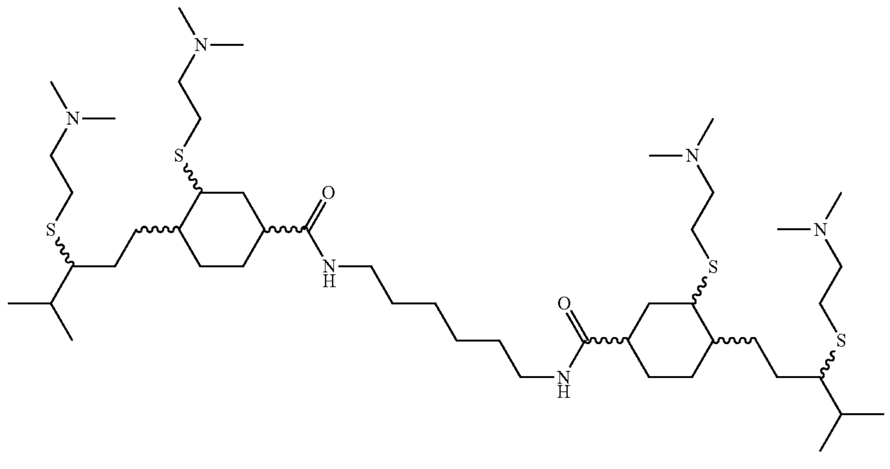

N,N'-(hexane-1,6-diyl)bis(3-((2-(dimethylamino) ethyl)thio)-5-(2-((2-(dimethylamino)ethyl)thio)-3-methylbutyl)cyclohexane-1-carboxamide)

Synthesis Compound 2

Compound 2 was prepared in the exact same manner as Compound 1 except the initial (step a) Diels-Alder reaction was conducted with beta-myrcene instead of trans-beta-farnesene. Molar ratios and reaction conditions for step b (transamidation) and step c (photochemical thiolation) were identical to that of Compound 1. $C_{48}H96N_6O_2S_4$. $^1H$ NMR (500 MHz, $d_6$-DMSO) δ: 3.37 (m), 3.18 (m (br)), 2.99 (br), 2.85 (br), 2.77 (s), 2.74 (m (br)), 2.03-1.16 (m (br)), 0.94 (s), 0.88 (s).

COMPOUND 3

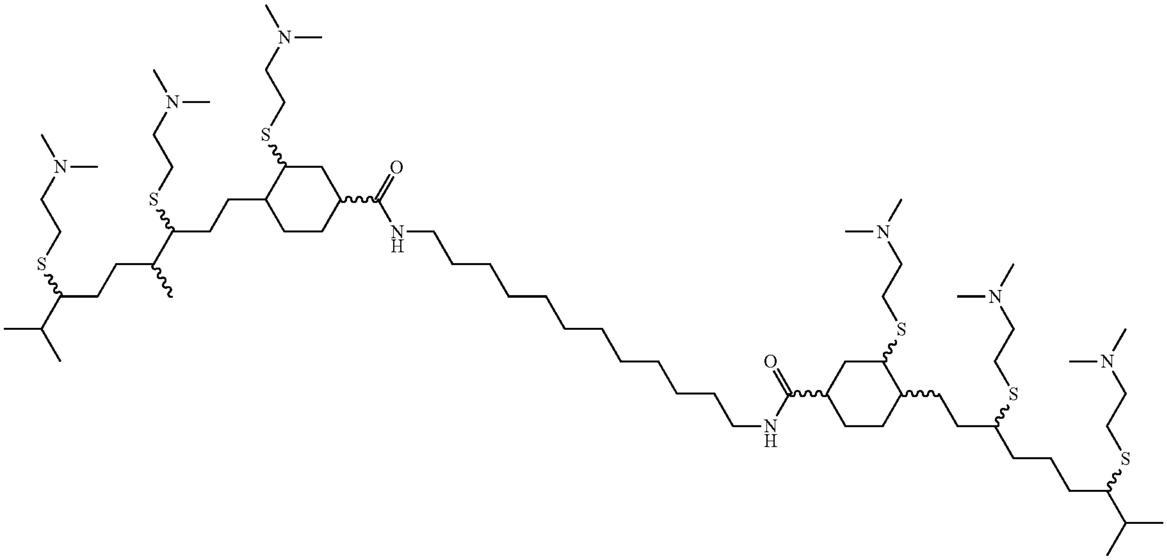

Synthesis of COMPOUND 3

This compound was prepared two separate ways.

Synthesis 1

Compound 3 was prepared in the same manner as Compound 1 except 1,12-daminododecane was substituted for hexamethylenediamine. Molar ratios and reaction conditions for Compound 3's three step synthetic sequence were identical to that of Compound 1. $C_{72}H_{146}N_8O_2S_6$. $^1H$ NMR (500 MHz, $d_6$-DMSO) δ: 3.25 (m), 3.16 (m (br)), 3.00 (br), 2.85 (br), 2.69 (s), 2.21-1.32 (m (br)), 1.22 (m (br)), 0.94 (s), 0.88 (s).

Synthesis 2

First, bola base was prepared according to Protocol A. The bola base had the following structure:

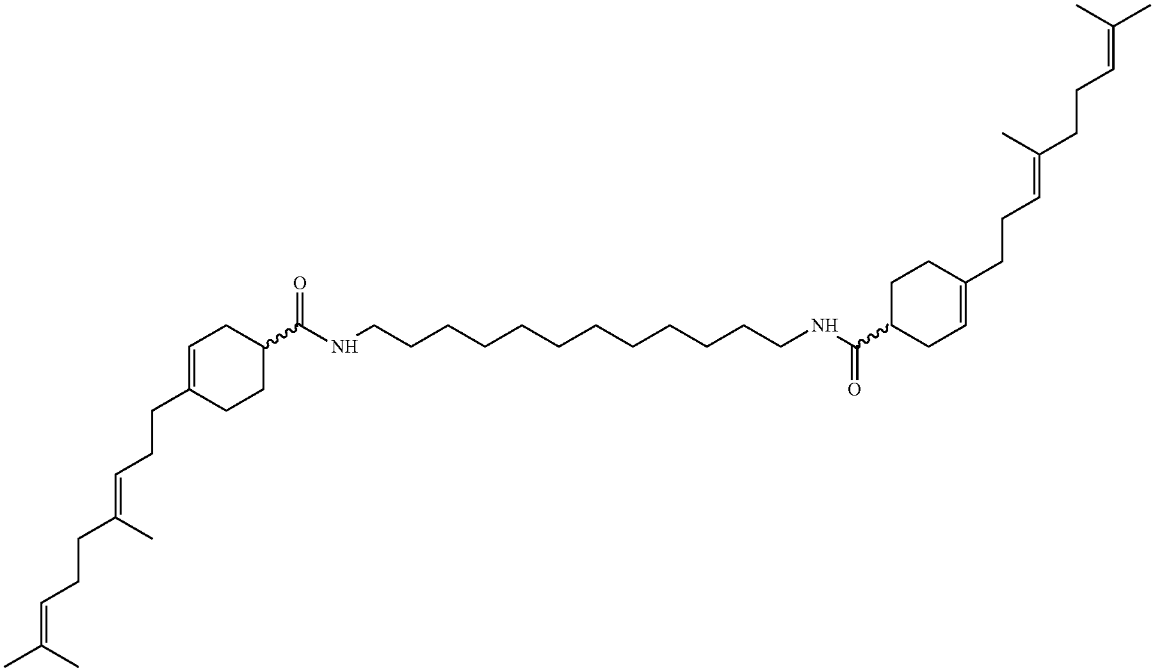 [SMILES: CC(C)=CCC/C(C)=C/CCC1=CCC(C(=O)NCCCCCCCCCCCCNC(=O)C2CC=C(CC/C=C(\C)CCC=C(C)C)CC2)CC1]
The results were:
75% yield, off-white solid. 1H NMR (500 MHz, CDCl3) δ 5.66 (s, 2H), 5.39 (s, 2H), 5.13-5.02 (m, 4H), 3.27-3.18 (m, 4H), 2.38-2.13 (m, 6H), 2.12-1.80 (m, 23H), 1.77-1.65 (m, 8H), 1.63-1.56 (m, 11H), 1.52-1.42 (m, 4H), 1.34-1.20 (m, 16H). 13C NMR (126 MHz, CDCl3) δ 175.99, 137.73, 136.35, 135.29, 135.25, 131.41, 124.40, 124.10, 124.07, 120.45, 119.13, 42.03, 41.53, 39.82, 39.53, 39.50, 37.84, 37.64, 31.46, 29.78, 29.59, 29.37, 28.48, 27.91, 26.99, 26.82, 26.37, 26.33, 26.29, 25.96, 25.83, 24.83, 17.81, 16.15, 16.12.
Then, Protocol B was followed. The results were:
1H NMR (500 MHz, DMSO-d6) δ 3.25-3.06 (m, 14H), 3.03-2.79 (m, 15H), 2.78-2.64 (m, 38H), 1.97-1.46 (m, 23H), 1.42-1.06 (m, 38H), 1.02-0.64 (m, 18H).
COMPOUND 4
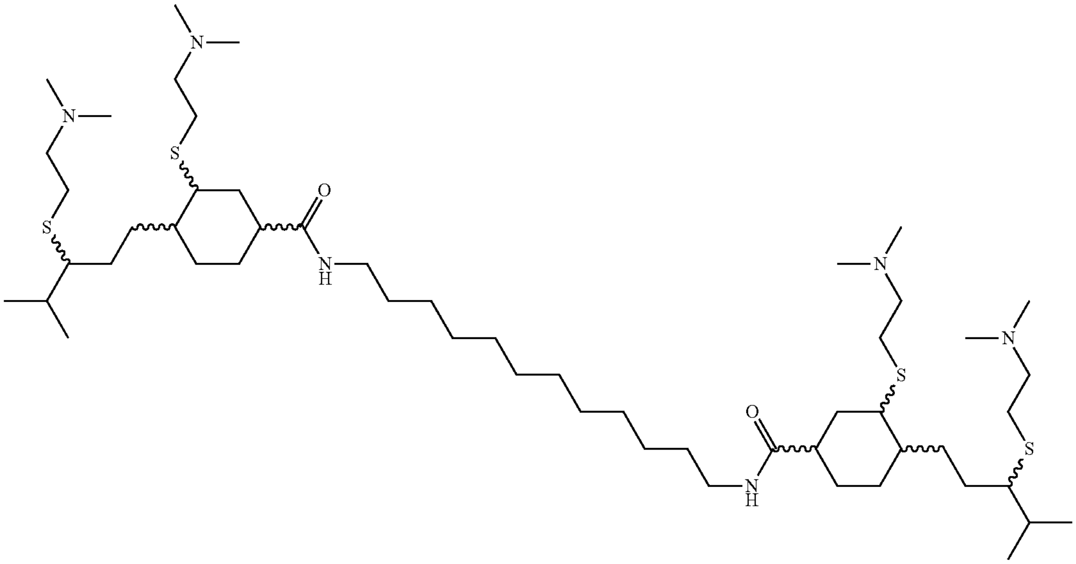

Synthesis of COMPOUND 4. Compound 4 was prepared in the exact same manner as Compound 1 except beta-myrcene was used in the initial Diels-Alder reaction (step a) instead of trans-beta-farnesene and 1,12-daminododecane was substituted for hexamethylenediamine (step b). Molar ratios and reaction conditions for steps a-c were identical to that of Compound 1. $C_{48}H_{96}N_6O_2S_4$. $^1$H NMR (500 MHz, $d_6$-DMSO) δ: 3.18 (m (br)), 2.99 (br), 2.85 (br), 2.77 (s), 2.74 (m (br)), 2.03-1.16 (m (br)), 0.94 (s), 0.88 (s).

COMPOUND 5

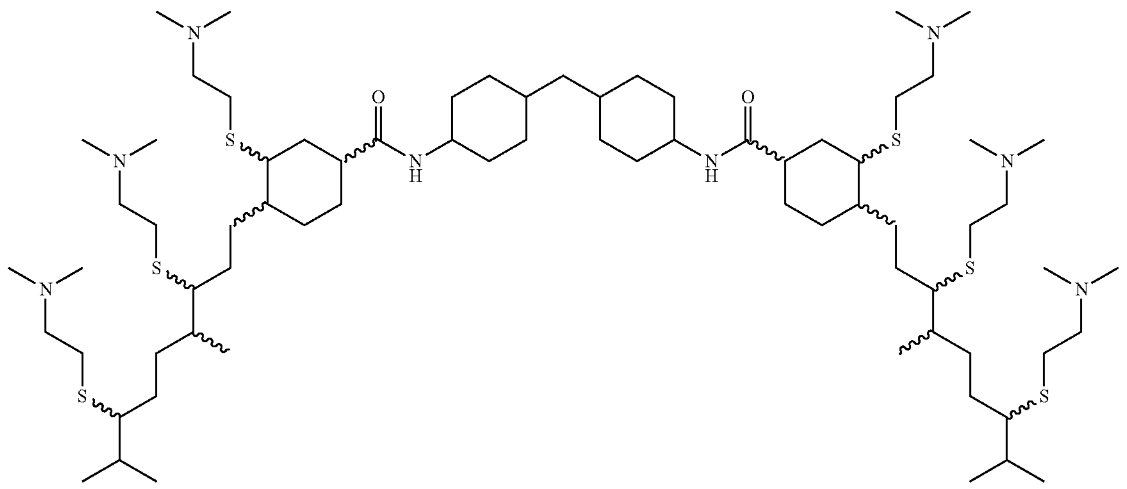

3-(2,6-bis((2-(dimethylamino)ethyl)thio)-3,7-dimethyloctyl)-5-((2-(dimethylamino)ethyl)thio)-N-(3-((3-(3-((2-(dimethylamino)ethyl)thio)-5-(6-((2-(dimethylamino)ethyl)thio)-2-(((2-(dimethylamino)ethyl)thio)methyl)-3,7-dimethyloctyl)cyclohexane-1-carboxamido)cyclohexyl)methyl)cyclohexyl)cyclohexane-1-carboxamide Synthesis of COMPOUND 5. Compound 5 was prepared in the exact same manner as Compound 1 except 4,4'-methylenebis(cyclohexylamine) was substituted for hexamethylenediamine. Molar ratios and reaction conditions for Compound 5's three step synthetic sequence were identical to that of Compound 1. $C_{73}H_{144}N_8O_2S_6$. $^1$H NMR (500 MHz, $d_6$-DMSO) δ: 3.40-3.33 (m(br)), 3.18 (m), 2.77 (s), 1.91 (br), 1.71-1.55 (m (br)), 1.33-0.85 (m(br)).

COMPOUND 6

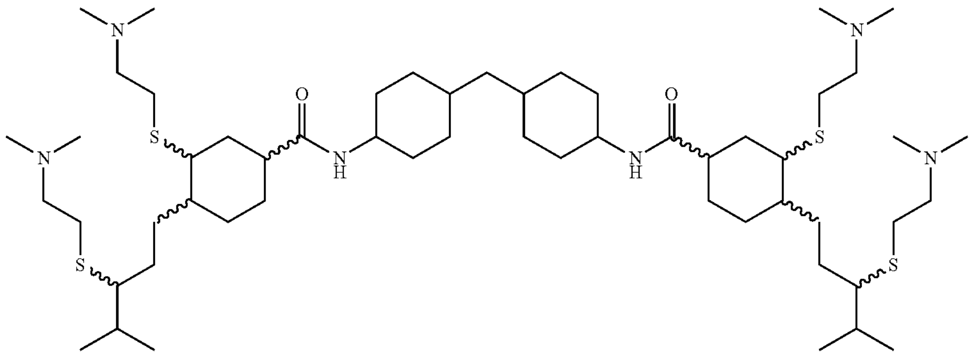

3-((2-(dimethylamino)ethyl)thio)-5-(2-((2-(dimethylamino)ethyl)thio)-3-methylbutyl)-N-(3-((3-(3-((2-(dimethylamino)ethyl)thio)-5-(2-(((2-(dimethylamino)ethyl)thio)methyl)-3-methylbutyl) cyclohexane-1-carboxamido)cyclohexyl)methyl) cyclohexyl)cyclohexane-1-carboxamide Synthesis of COMPOUND 6. Compound 6 was prepared in the exact same manner as Compound 1 except beta-myrcene was used in the initial Diels-Alder reaction (step a) instead of trans-beta-farnesene and 4,4'-methylenebis(cyclohexylamine) was substituted for hexamethylenediamine (step b). Molar ratios and reaction conditions for steps a-c were identical to that of Compound 1. $C_{55}H_{106}N_6O_2S_4$. $^1H$ NMR (500 MHz, $d_6$-DMSO) δ: 3.58-3.26 (m (br)), 3.25 (m), 3.01 (m), 2.86 (m), 2.68 (s), 2.19-0.84 (m (br)).

COMPOUND 7

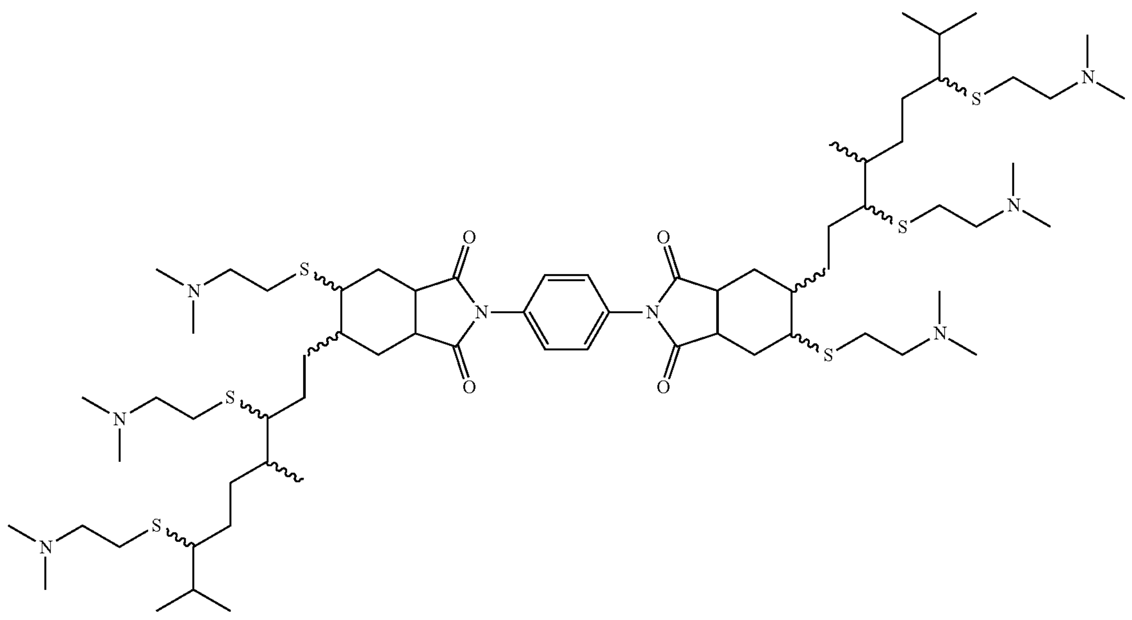

5-(3,7-bis((2-(dimethylamino)ethyl)thio)-4,8-dimethylnonyl)-2-(4-(5-(3,7-bis((2-(dimethylamino)ethyl)thio)-4,8-dimethylnonyl)-6-((2-(dimethylamino)ethyl)thio)-3-methylene-1-oxooctahydro-2H-isoindol-2-yl)phenyl)-6-((2-(dimethylamino)ethyl)thio)hexahydro-1H-isoindole-1,3(2H)-dione Synthesis of COMPOUND 7

Step a. Preparation of Bolaamphiphilic Precursor via Diels-Alder Reaction of Trans-Beta-Farnesene and N,N'-(1,4-Phenylene)Dimaleimide.

Trans-beta-farnesene (3 molar equivalents) was added to a heavy walled vial along with N,N'-(1,4-phenylene)dimaleimide (1 molar equivalent). The vial was sealed and heated to 130° C. After 30 minutes the reaction solidified yielding the crude product. The crude solid was removed from the reaction vessel, suspended in hexanes, and stirred. The mixture was centrifuged and the hexane supernatant decanted away from the product. The product was dried in a vacuum oven at 40° C.

Step b. Preparation of Multivalent Cationic Bolaamphiphilic Compound of Formula (I) Using a Photochemical Thiol-Ene Reaction.

In a 4 mL sealable vessel, 2-(dimethylamino)ethanthiol hydrochloride (198 mg, 1.4 mmol) was dissolved in 0.06 mL methanol and 0.94 mL chloroform. Compound from step a above (100 mg, 0.14 mmol) was added along with 20 mol % 2,4-diethyl-9H-thioxanthen-9-one relative to the thiol along with a stir bar. The solution was stirred at room temperature and irradiated using two 370 nm light emitting diodes from 5 cm away overnight. The chloroform-methanol solution was removed by rotary evaporation and the resulting yellow solid was washed using three portions of ethyl acetate. The washed solid was redissolved in water, placed in 100-500 D molecular weight cut off cellulose ester tubing and dialyzed against deionized water. The water was changed twice in the first 8 hours before being left overnight. The final product was isolated by lyophilization (37 mg). $C_{68}H_{122}N_8O_4S_6$. $^1H$ NMR (500 MHz, $d_6$-DMSO) 7.30 (br), 3.24 (m), 3.16 (m), 2.82 (br), 2.69 (s), 2.00-1.55 (m (br)), 1.19 (br), 0.94 (s), 0.88 (s).

COMPOUND 8

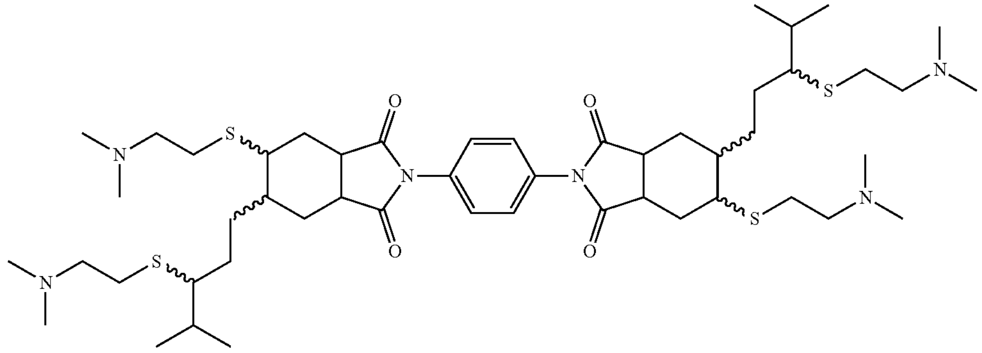

5-((2-(dimethylamino)ethyl)thio)-6-(3-((2-(dimethylamino)ethyl)thio)-4-methylpentyl)-2-(4-(5-((2-(dimethylamino)ethyl)thio)-6-(3-((2-(dimethylamino)ethyl)thio)-4-methylpentyl)-1-methylene-3-oxooctahydro-2H-isoindol-2-yl)phenyl)hexahydro-1H-isoindole-1,3(2H)-dione Synthesis of COMPOUND 8. Compound 8 was prepared in the exact same manner as Compound 7 except beta-myrcene was used in the initial Diels-Alder reaction (step a) instead of trans-beta-farnesene. Molar ratios and reaction conditions for steps a-b were identical to that of Compound 7. $C_{50}H_{84}N_6O_4S_6$. $^1$H NMR (500 MHz, $d_6$-DMSO) 7.28 (br), 3.31 (m), 3.14-3.07 (m), 2.77 (br), 2.62 (s), 2.24-1.84 (m (br)), 1.18 (br), 0.86 (m).

COMPOUND 9

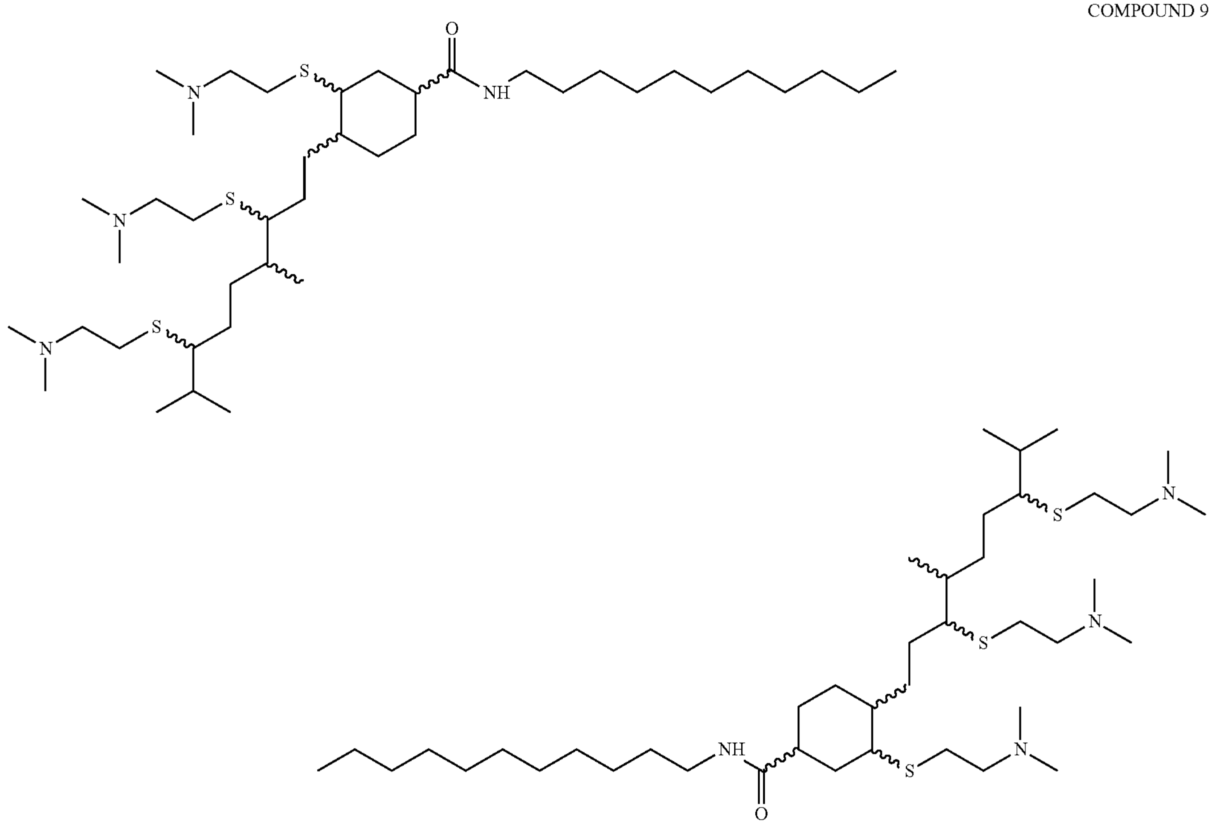

N,N'-(icosane-1,20-diyl)bis(4-(3,7-bis((2-(dimethylamino)ethyl)thio)-4,8-dimethylnonyl)-3-((2-(dimethylamino)ethyl)thio)cyclohexanecarboxamide)
This compound can be prepared by following Protocol A for bola base preparation, to yield bola base of the following structure:
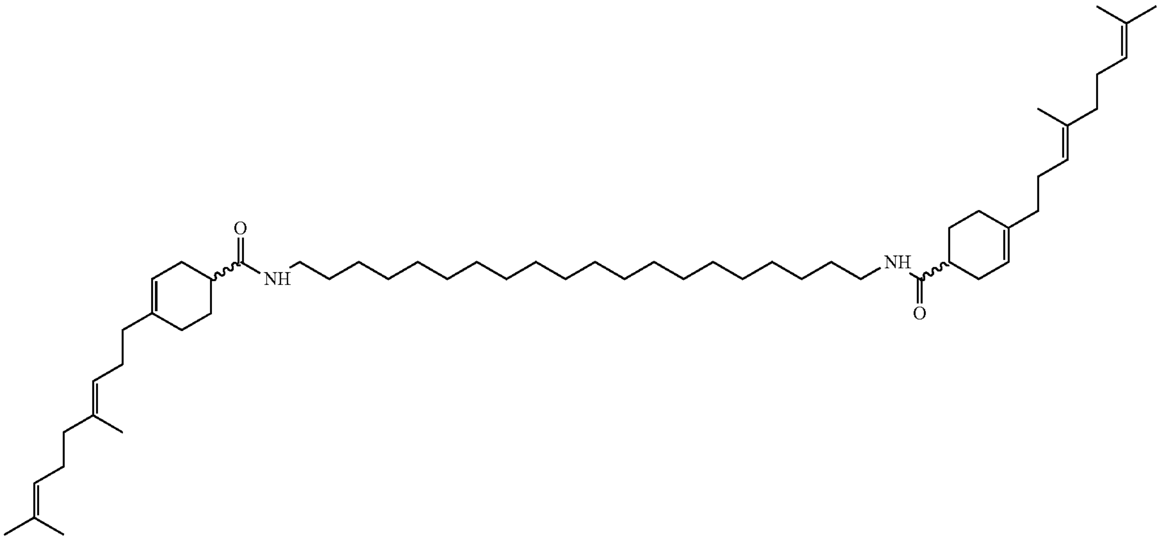 [SMILES: CC(C)=CCC/C(C)=C/CCC1=CCC(C(=O)NCCCCCCCCCCCCCCCCCCCCNC(=O)C2CC=C(CC/C=C(\C)CCC=C(C)C)CC2)CC1]
and then following Protocol B for bolaamphiphile preparation.
COMPOUND 10
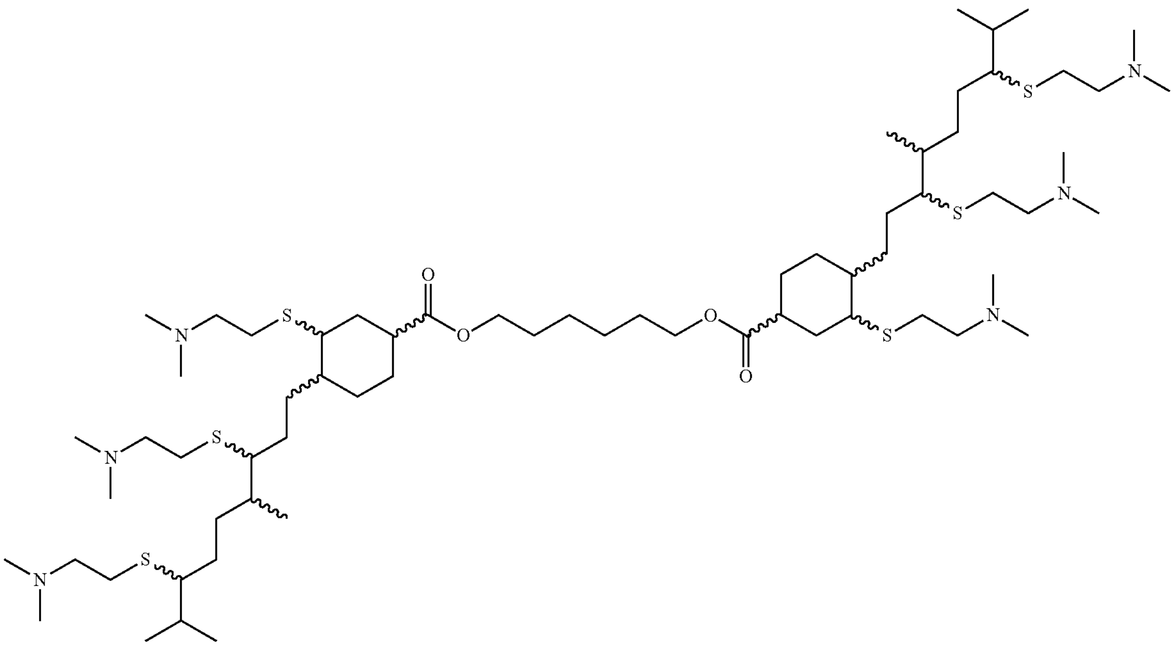

hexane-1,6-diyl bis(4-(3,7-bis((2-(dimethylamino)ethyl)thio)-4,8-dimethylnonyl)-3-((2-(dimethylamino)ethyl)thio)cyclohexanecarboxylate)

Synthesis of Compound 10

First, bola base was prepared according to Protocol A. The bola base had the following structure:

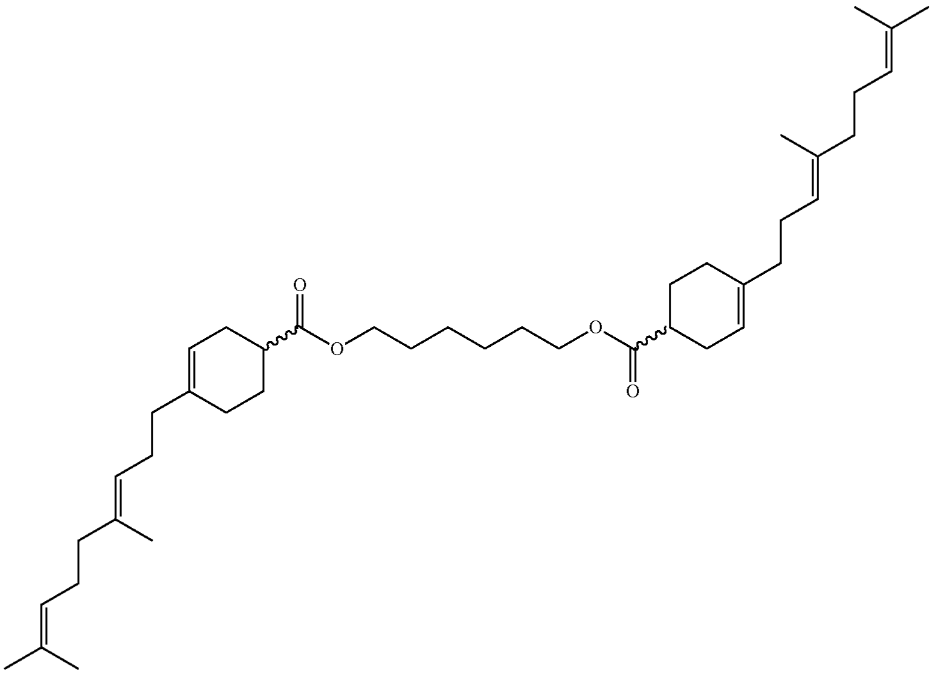 [SMILES: CC(C)=CCC/C(C)=C/CCC1=CCC(C(=O)OCCCCCCOC(=O)C2CC=C(CC/C=C(\C)CCC=C(C)C)CC2)CC1]

The results were:

44% yield, pale yellow oil. 1H NMR (500 MHz, CDCl3) δ 5.43-5.35 (m, 2H), 5.14-505 (m, 4H), 4.12-4.03 (m, 4H), 2.59-2.43 (m, 2H), 2.30-1.91 (m, 26H), 1.75-1.54 (m, 24H), 1.46-1.31 (m, 4H). 13C NMR (126 MHz, CDCl3) δ 176.23, 176.19, 137.48, 136.11, 135.24, 135.22, 131.41, 124.45, 124.17, 124.14, 120.38, 119.03, 64.35, 64.30, 40.06, 39.83, 39.64, 37.81, 37.64, 30.76, 28.69, 27.88, 27.83, 26.94, 26.84, 26.38, 26.35, 25.84, 25.75, 25.70, 25.32, 24.69, 17.83, 16.15.

Then, Protocol B procedure was followed. The results were:

1H NMR (500 MHz, DMSO-d6) δ 4.04-3.94 (m, 4H), 3.33-3.11 (m, 14H), 2.90-2.79 (m, 10H), 2.75 (d, J=3.4 Hz, 38H), 2.70-2.54 (m, 6H), 2.12-2.05 (m, 4H), 1.94-1.06 (m, 42H), 1.00-0.79 (m, 18H).

COMPOUND 11
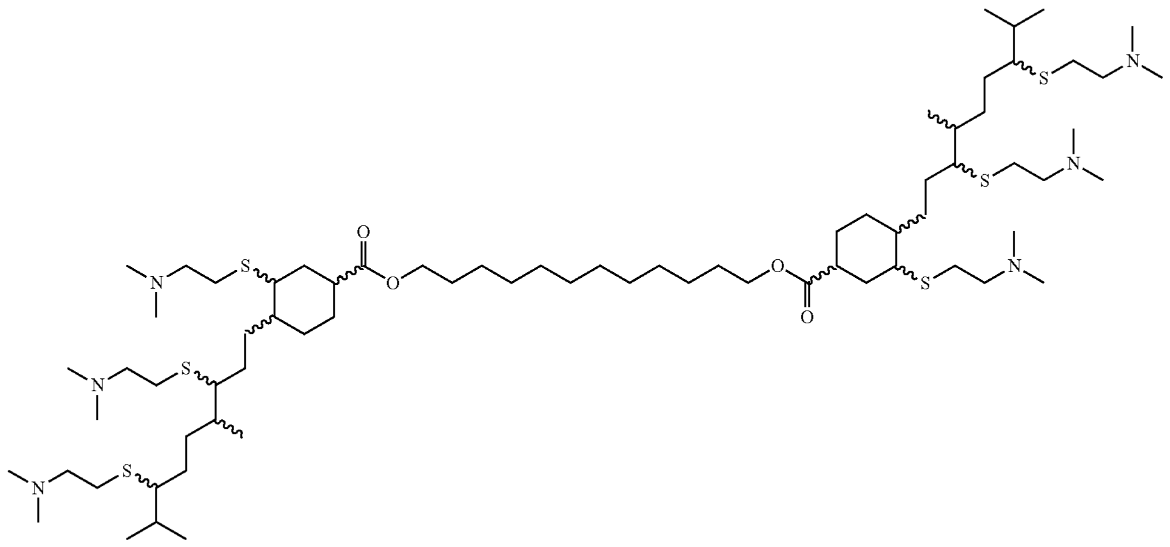
dodecane-1,12-diyl bis(4-(3,7-bis((2-(dimethylamino)ethyl)thio)-4,8-dimethylnonyl)-3-((2-(dimethylamino)ethyl)thio)cyclohexanecarboxylate)
Synthesis of Compound 11
First, bola base was prepared according to Protocol A. The bola base had the following structure:
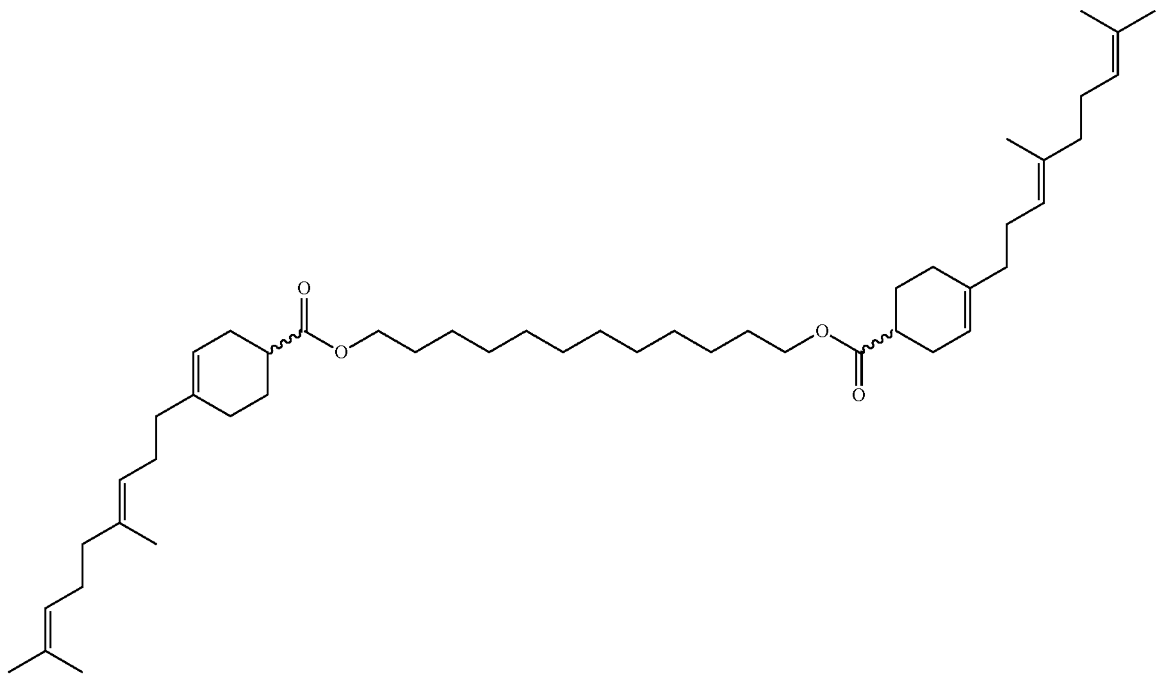 [SMILES: CC(C)=CCC/C(C)=C/CCC1=CCC(C(=O)OCCCCCCCCCCCCOC(=O)C2CC=C(CC/C=C(\C)CCC=C(C)C)CC2)CC1]
The results were:
45% yield, pale yellow oil. 1H NMR (500 MHz, CDCl3) δ 5.39 (bs, 2H), 5.09 (bs, 4H), 4.11-4.03 (m, 4H), 2.59-2.42 (m, 2H), 2.30-1.91 (m, 26H), 1.73-1.56 (m, 24H), 1.40-1.23 (m, 16H). 13C NMR (126 MHz, CDCl3) δ 176.24, 176.20, 137.44, 136.13, 135.21, 135.19, 131.38, 124.44, 124.17, 124.15, 120.37, 119.07, 64.56, 64.51, 40.06, 39.82, 39.64, 37.81, 37.64, 30.76, 29.67, 29.64, 29.38, 28.77, 27.83, 26.83, 26.37, 26.34, 26.04, 25.83, 25.68, 25.30, 24.69, 17.81, 16.13, 16.12.

Then, Protocol B procedure was followed. The results were:

1H NMR (400 MHz, DMSO-d6) δ 4.02-3.94 (m, 4H), 3.21-3.04 (m, 14H), 2.88-2.78 (m, 10H), 2.73 (s, 36H), 2.60-2.52 (m, 2H), 2.11-1.39 (m, 36H), 1.31-1.14 (m, 24H), 1.00-0.73 (m, 18H).

COMPOUND 12

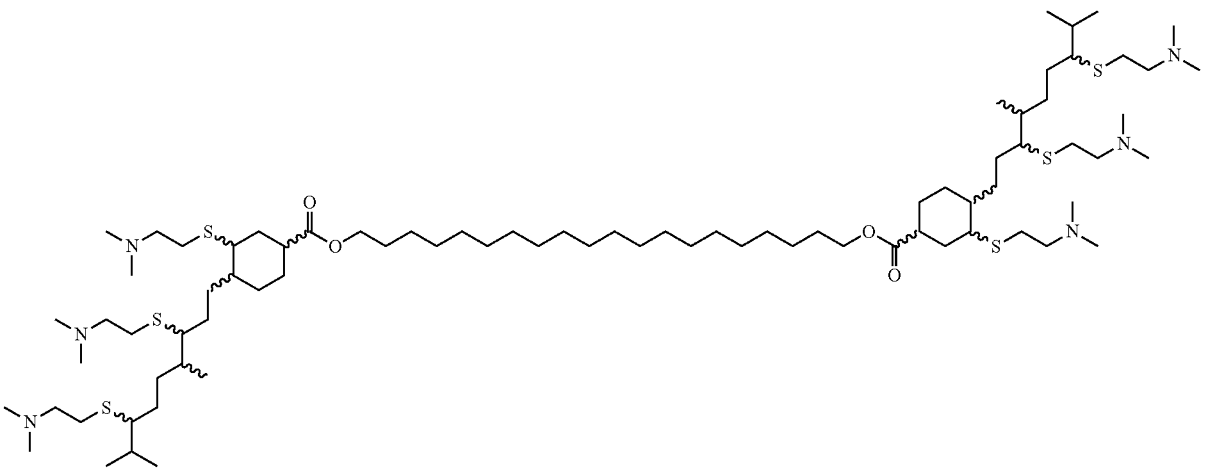

icosane-1,20-diyl bis(4-(3,7-bis((2-(dimethylamino) ethyl)thio)-4,8-dimethylnonyl)-3-((2-(dimethyl-amino)ethyl)thio)cyclohexanecarboxylate)

Synthesis of Compound 12

First, bola base was prepared according to Protocol A. The bola base had the following structure:

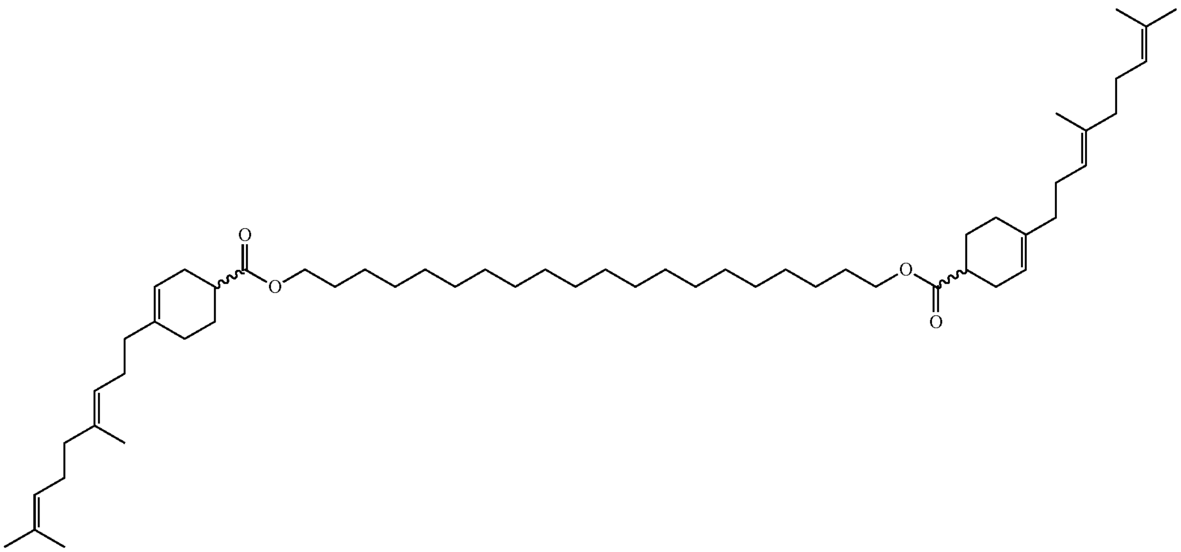 [SMILES: CC(C)=CCC/C(C)=C/CCC1=CCC(C(=O)OCCCCCCCCCCCCCCCCCCCCOC(=O)C2CC=C(CC/C=C(\C)CCC=C(C)C)CC2)CC1]

The results were:

49% yield; pale yellow oil; 1H NMR (400 MHz, CDCl3) δ 5.44-5.33 (m, 2H), 5.18-5.01 (m, 4H), 4.12-4.01 (m, 4H), 2.61-2.40 (m, 2H), 2.30-1.88 (m, 26H), 1.78-1.48 (m, 24H), 1.25 (d, J=4.8 Hz, 32H).

Then, Protocol B procedure was followed. The results were:

1H NMR (400 MHz, DMSO-d6) δ 4.05-3.94 (m, 4H), 3.30-3.27 (m, 12H), 3.17-3.13 (m, 12H), 2.91-2.80 (m, 2H), 2.73 (s, 36H), 1.99-1.82 (m, 9H), 1.78-1.50 (m, 21H), 1.24 (d, J=12.2 Hz, 46H), 1.03-0.64 (m, 18H).

COMPOUND 13
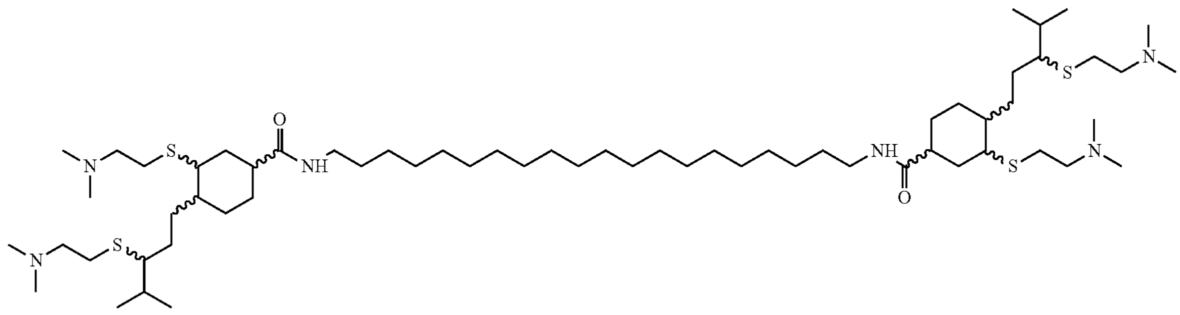
N,N'-(icosane-1,20-diyl)bis(3-((2-(dimethylamino)ethyl)thio)-4-(3-((2-(dimethylamino)ethyl)thio)-4-methylpentyl)cyclohexanecarboxamide)
This compound can be prepared by following Protocol A for bola base preparation, resulting in preparation of the bola base of the following structure:
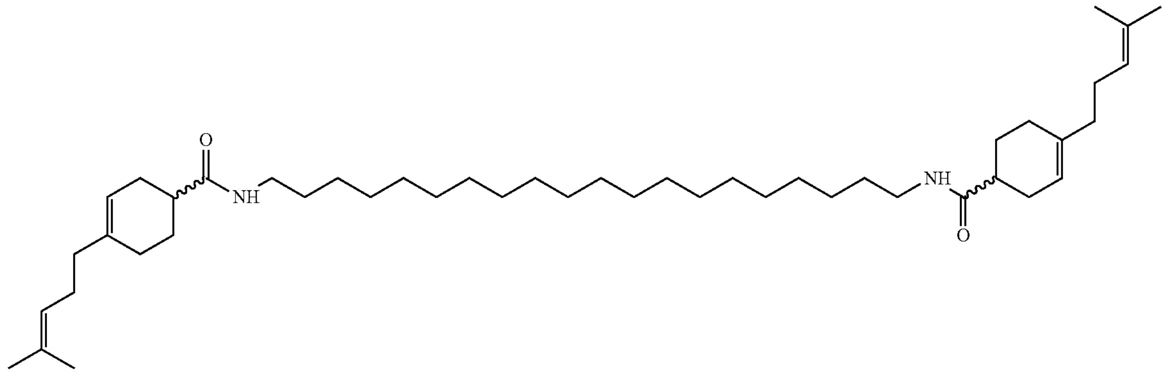
and then following Protocol B for bolaamphiphile preparation.
COMPOUND 14
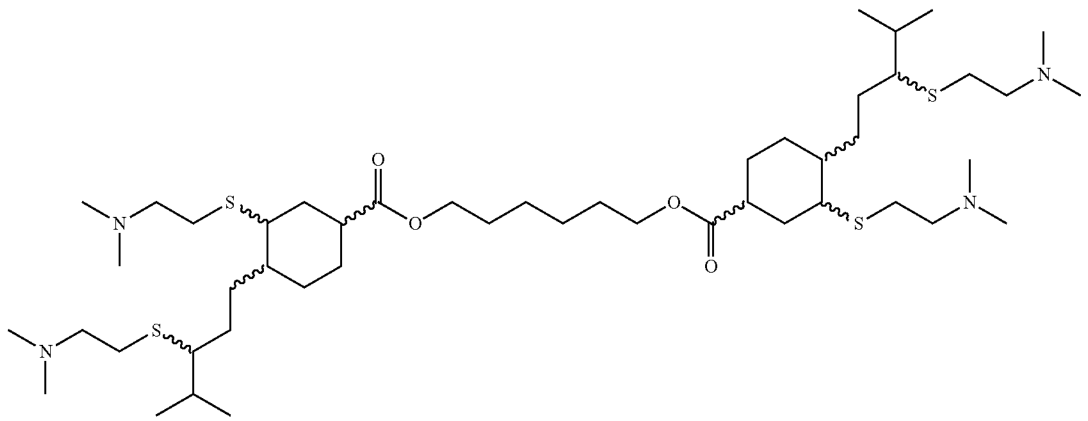

hexane-1,6-diyl bis(3-((2-(dimethylamino)ethyl)thio)-4-(3-((2-(dimethylamino)ethyl)thio)-4-methylpentyl)cyclohexanecarboxylate)

Synthesis of Compound 14

First, bola base was prepared according to Protocol A. The bola base had the following structure:

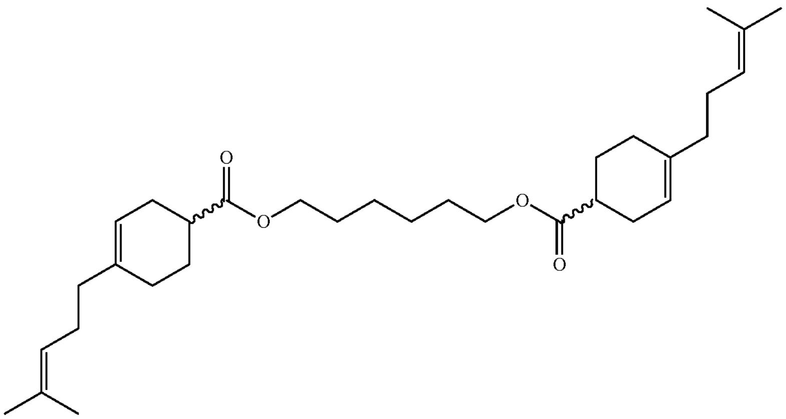 [SMILES: CC(C)=CCCC1=CCC(C(=O)OCCCCCCOC(=O)C2CC=C(CCC=C(C)C)CC2)CC1]

The results were:

21% yield; 1H NMR (500 MHz, CDCl3) δ 5.42-5.29 (m, 2H), 5.12-5.00 (m, 2H), 4.13-3.98 (m, 4H), 2.59-2.40 (m, 2H), 2.33-1.85 (m, 19H), 1.73-1.52 (m, 17H), 1.48-1.21 (m, 4H). 13C NMR (126 MHz, CDCl3) δ 176.12, 176.08, 137.41, 136.08, 131.52, 131.49, 124.24, 120.28, 118.95, 64.27, 64.22, 39.99, 39.57, 37.77, 37.61, 30.73, 28.64, 27.78, 27.76, 26.43, 25.77, 25.69, 25.62, 25.25, 24.62, 17.77, 17.76.

Then, Protocol B procedure was followed. The results were:

1H NMR (500 MHz, DMSO-d6) δ 4.03-3.93 (m, 4H), 3.25-3.17 (m, 8H), 3.16-3.03 (m, 8H), 2.85-2.76 (m, 4H), 2.73-2.64 (m, 24H), 2.54 (d, J=10.5 Hz, 2H), 2.17-1.18 (m, 32H), 1.00-0.73 (m, 12H).

COMPOUND 15

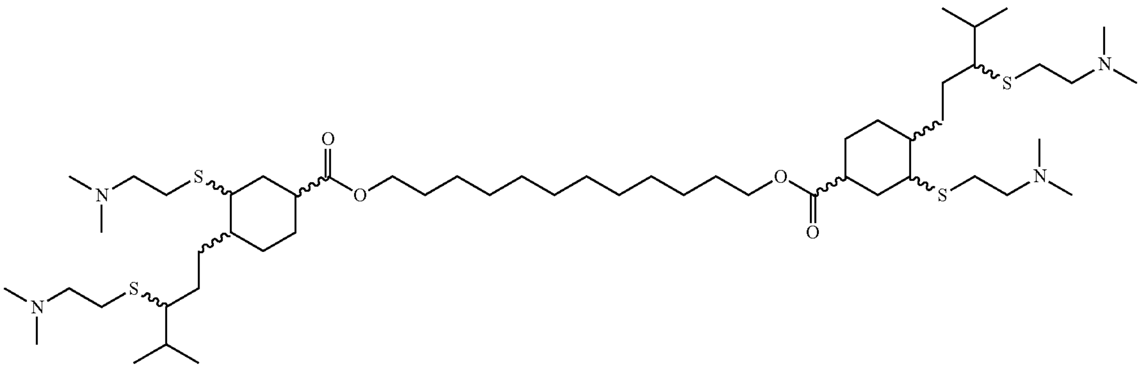

dodecane-1,12-diyl bis(3-((2-(dimethylamino)ethyl)thio)-4-(3-((2-(dimethylamino)ethyl)thio)-4-methylpentyl)cyclohexanecarboxylate)

Synthesis of Compound 15

First, bola base was prepared according to Protocol A. The bola base had the following structure:

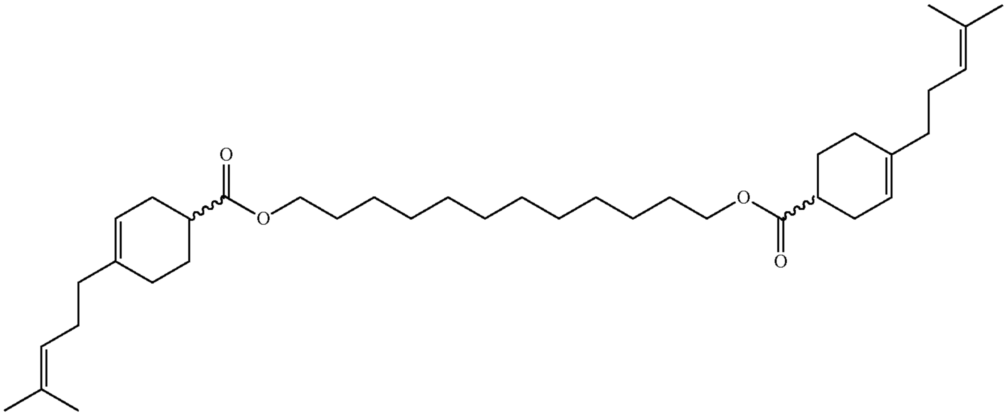 [SMILES: CC(C)=CCCC1=CCC(C(=O)OCCCCCCCCCCCCOC(=O)C2CC=C(CCC=C(C)C)CC2)CC1]

The results were:

28% yield, pale yellow oil. 1H NMR (500 MHz, CDCl3) δ 5.44-5.34 (m, 2H), 5.14-5.04 (m, 2H), 4.12-4.02 (m, 4H), 2.59-2.43 (m, 2H), 2.30-1.90 (m, 18H), 1.76-1.53 (m, 18H), 1.27 (s, 16H). 13C NMR (126 MHz, CDCl3) δ 176.28, 176.25, 137.50, 137.49, 136.19, 131.64, 131.62, 124.30, 120.35, 119.05, 64.59, 64.55, 40.09, 39.67, 37.85, 37.68, 30.80, 29.68, 29.66, 29.39, 28.79, 27.84, 26.51, 26.50, 26.06, 25.85, 25.69, 25.31, 24.70, 17.85, 17.84.

Then, Protocol B procedure was followed. The results were:

1H NMR (500 MHz, DMSO-d6) δ 4.06-3.89 (m, 4H), 3.40-3.29 (m, 8H), 3.26-3.08 (m, 8H), 2.95-2.53 (m, 32H), 2.20-1.13 (m, 42H), 1.00-0.78 (m, 12H).

COMPOUND 16

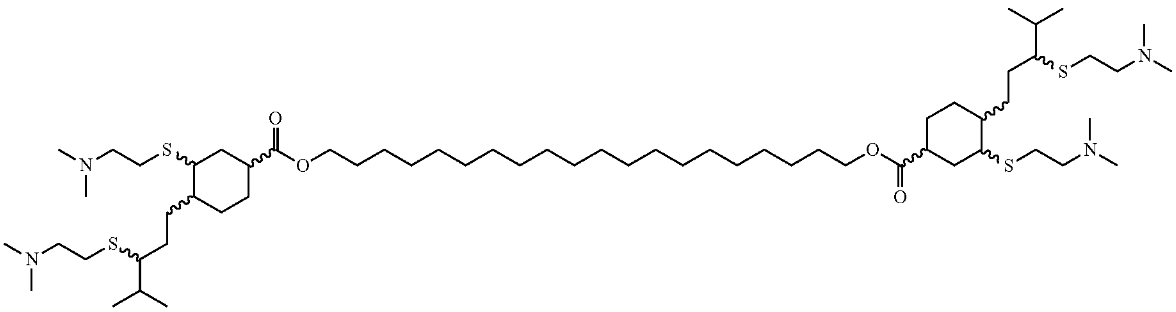

icosane-1,20-diyl bis(3-((2-(dimethylamino)ethyl)thio)-4-(3-((2-(dimethylamino)ethyl)thio)-4-methylpentyl)cyclohexanecarboxylate)

Synthesis of Compound 16

First, bola base was prepared according to Protocol A. The bola base had the following structure:

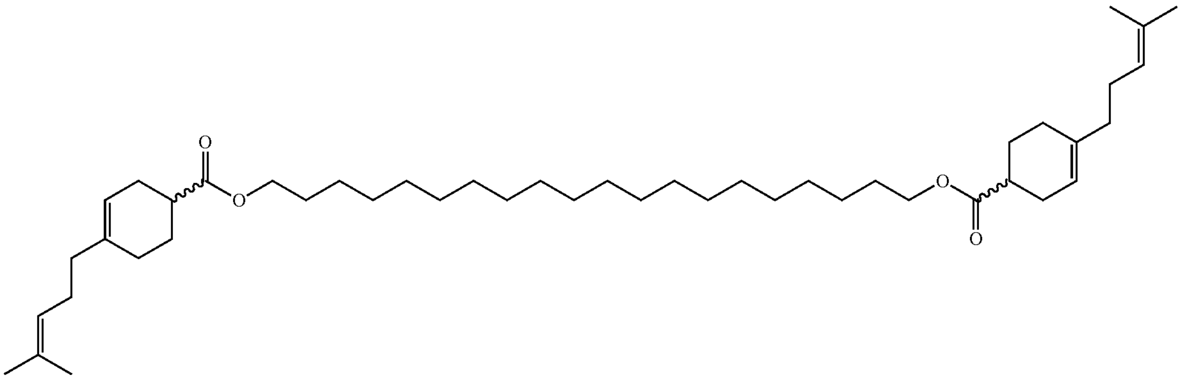 [SMILES: CC(C)=CCCC1=CCC(C(=O)OCCCCCCCCCCCCCCCCCCCCOC(=O)C2CC=C(CCC=C(C)C)CC2)CC1]

The results were:

59% yield; 1H NMR (500 MHz, CDCl3) δ 5.45-5.33 (m, 2H), 5.16-5.02 (m, 2H), 4.16-3.95 (m, 4H), 2.60-2.35 (m, 2H), 2.30-1.88 (m, 18H), 1.82-1.50 (m, 18H), 1.42-1.09 (m, 32H). 13C NMR (126 MHz, CDCl3) δ 176.29, 176.26, 137.50, 136.21, 131.64, 131.62, 124.31, 120.35, 119.05, 64.61, 64.57, 40.10, 39.67, 37.85, 37.69, 30.81, 29.86, 29.84, 29.80, 29.73, 29.68, 29.40, 28.80, 27.85, 26.51, 26.07, 25.85, 25.70, 25.32, 24.71, 17.86, 17.84.

Then, Protocol B procedure was followed. The results were:

1H NMR (500 MHz, DMSO-d6) δ 4.05-3.95 (m, 4H), 3.37-3.05 (m, 11H), 2.99-2.53 (m, 36H), 2.42-1.01 (m, 59H), 0.98-0.83 (m, 12H).

COMPOUND 17

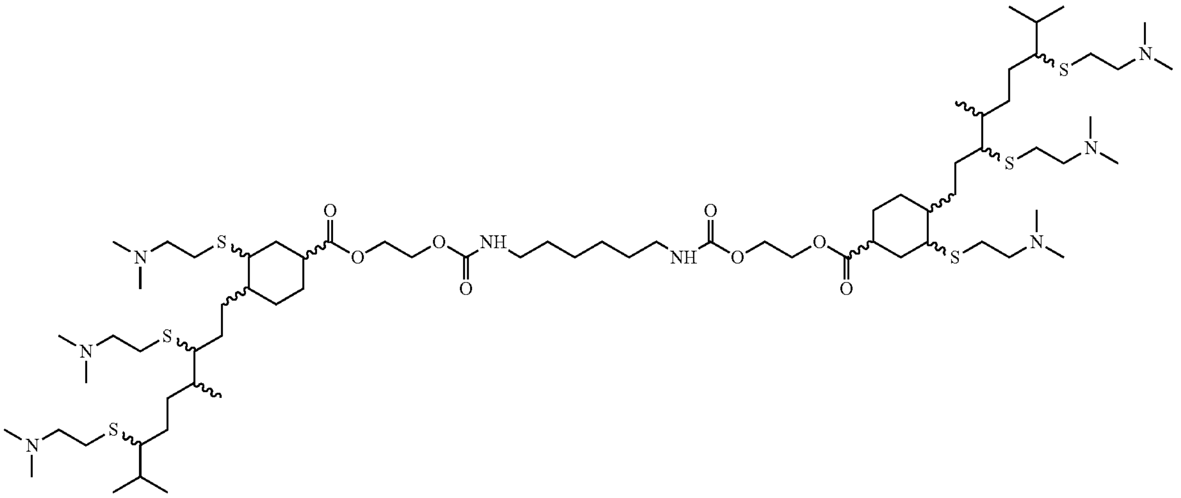

4,13-dioxo-3,14-dioxa-5,12-diazahexadecane-1,16-diyl bis(4-(3,7-bis((2-(dimethylamino)ethyl)thio)-4,8-dimethylnonyl)-3-((2-(dimethylamino)ethyl)thio) cyclohexanecarboxylate)

Synthesis of Compound 17

First, bola base was prepared as follows.

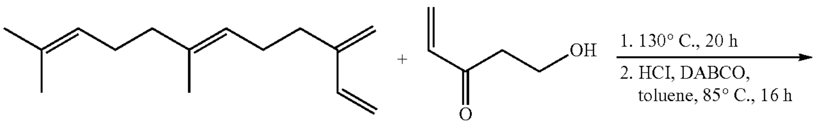

-continued

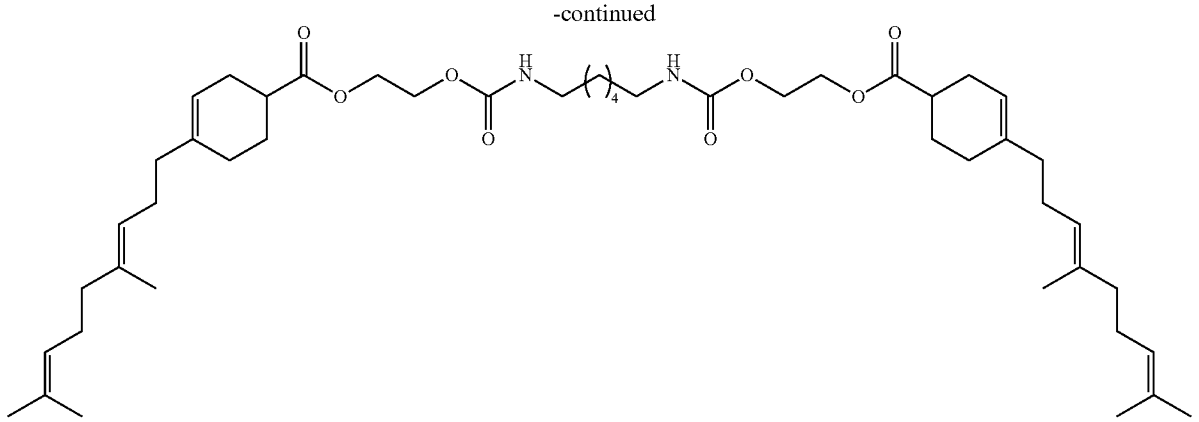

In a 4 mL sealable glass tube, trans-β-farnesene (1.02 g, 4.99 mmol, 1.0 eq) and hydroxyethyl acrylate (0.56 g, 4.99 mmol, 1.0 eq) were taken. The tube was sealed and stirred at 130° C. for 20 h. The reaction mixture was cooled and purified by silica gel chromatography with 20% EtOAc/hexane eluent to give the hydroxyl farnesene methyl ester. 86% yield, colorless oil; 1H NMR (500 MHz, CDCl3) δ 5.44-5.29 (m, 1H), 5.15-4.98 (m, 2H), 4.20 (q, J=4.7 Hz, 2H), 3.83-3.76 (m, 2H), 2.62-2.32 (m, 2H), 2.28-1.90 (m, 13H), 1.80-1.42 (m, 10H). 13C NMR (126 MHz, CDCl3) δ 176.57, 176.52, 137.46, 135.93, 135.22, 135.18, 131.32, 124.39, 124.07, 124.03, 120.34, 118.82, 66.02, 65.99, 61.26, 61.23, 39.91, 39.76, 39.47, 39.46, 37.71, 37.55, 30.68, 27.72, 27.69, 26.78, 26.30, 26.27, 25.76, 25.63, 25.24, 24.55, 17.75, 16.08, 16.06.

The hydroxyl compound (453 mg, 1.49 mmol, 2.5 eq) was mixed with hexamethylene diisocyanate, HDI (100 mg, 0.59 mmol, 1.0 eq), and DABCO (3 mg, 0.03 mmol, 5 mol %) in anhydrous toluene (2.0 mL). The resulting reaction mixture was stirred 85° C. for 16 h. Cooled, toluene was evaporated, the reaction mixture was partitioned between water (20 mL) and EtOAc (20 mL). Both layers were separated, aqueous layer was extracted with EtOAc (3×20 mL). Combined EtOAc extracts were washed with brine (20 mL), dried over $Na2SO_4$, filtered and evaporated. The crude was purified by silica gel chromatography with 30% EtOAc:hexanes as eluents to give final bola base (330 mg, 68%) as a semi-solid.

56% yield; off-white solid; 1H NMR (500 MHz, CDCl3) δ 5.44-5.33 (m, 2H), 5.16-5.02 (m, 4H), 4.83-4.69 (m, 2H), 4.36-4.18 (m, 8H), 3.24-3.03 (m, 4H), 2.66-2.44 (m, 2H), 2.31-1.78 (m, 26H), 1.74-1.62 (m, 8H), 1.62-1.54 (m, 12H), 1.54-1.44 (m, 4H), 1.39-1.28 (m, 4H). 13C NMR (126 MHz, CDCl3) δ 175.94, 175.89, 156.24, 137.51, 136.02, 135.30, 135.26, 131.42, 124.45, 124.13, 124.11, 120.39, 118.92, 62.75, 62.67, 62.63, 40.98, 39.90, 39.83, 39.48, 37.80, 37.63, 30.67, 29.96, 27.78, 27.75, 26.85, 26.38, 26.36, 26.35, 25.83, 25.63, 25.24, 24.63, 17.83, 16.16, 16.14.

Then, Protocol B procedure was followed. The results were:

1H NMR (400 MHz, DMSO-d6) δ 4.26-4.05 (m, 8H), 3.37-3.10 (m, 22H), 3.07-2.79 (m, 16H), 2.75 (s, 36H), 2.62-2.53 (m, 4H), 2.21-1.12 (m, 42H), 1.00-0.74 (m, 18H).

COMPOUND 18

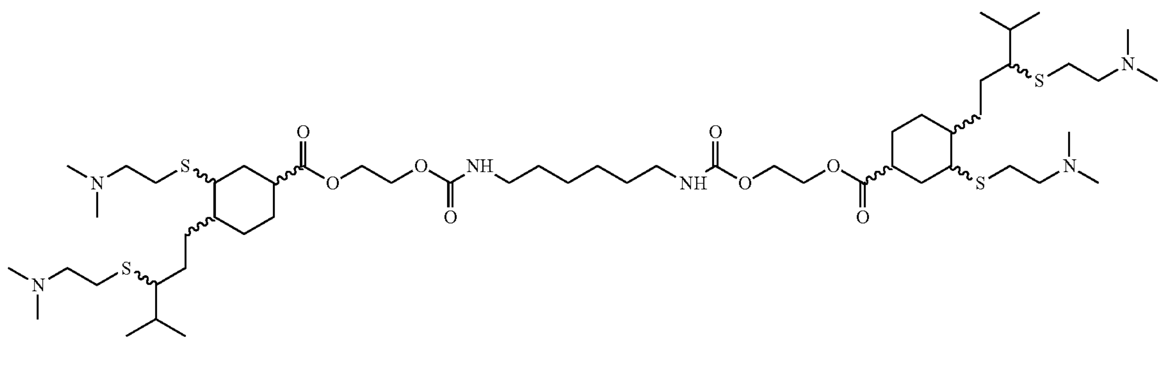

4,13-dioxo-3,14-dioxa-5,12-diazahexadecane-1,16-diyl bis(3-((2-(dimethylamino)ethyl)thio)-4-(3-((2-(dimethylamino)ethyl)thio)-4-methylpentyl)cyclohexanecarboxylate)

Compound 18 can be prepared by following the procedure described in the methods of preparation of Compound 17 for bola base preparation, and then following Protocol B for bolaamphiphile preparation.

COMPOUND 19

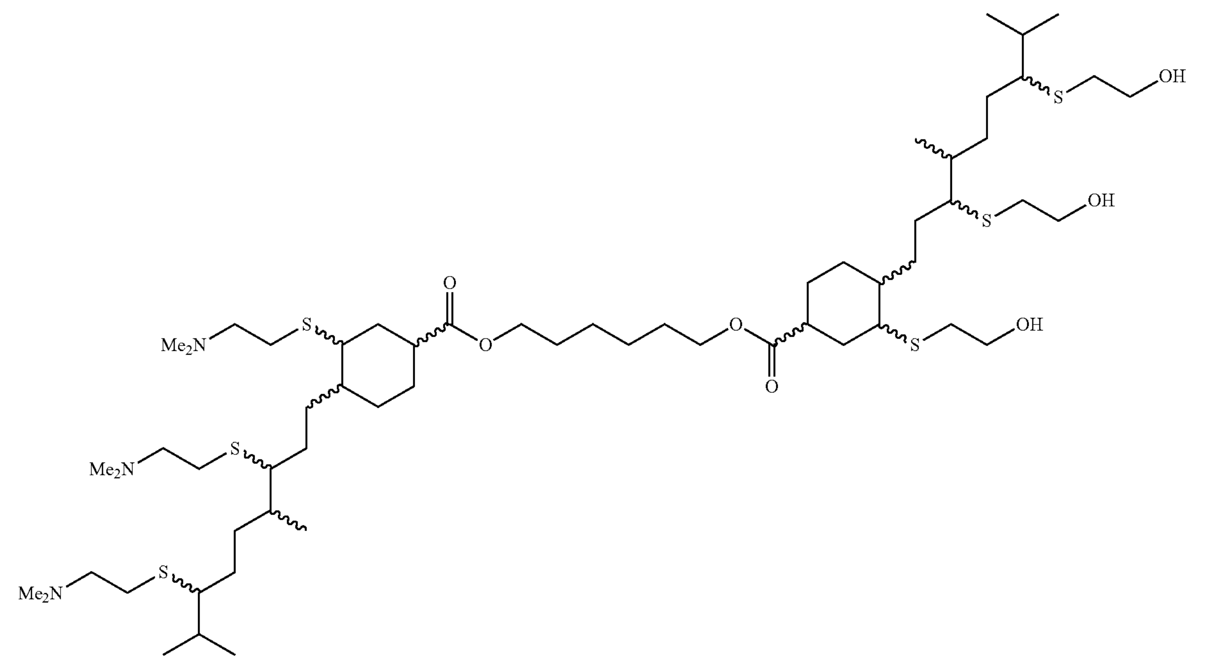

6-((4-(3,7-bis((2-(dimethylamino)ethyl)thio)-4,8-dimethylnonyl)-3-((2-(dimethylamino)ethyl)thio)cyclohexanecarbonyl)oxy)hexyl 4-(3,7-bis((2-hydroxyethyl)thio)-4,8-dimethylnonyl)-3-((2-hydroxyethyl)thio)cyclohexanecarboxylate Synthesis of Compound 19

First, bola base was prepared according to Protocol A as follows.

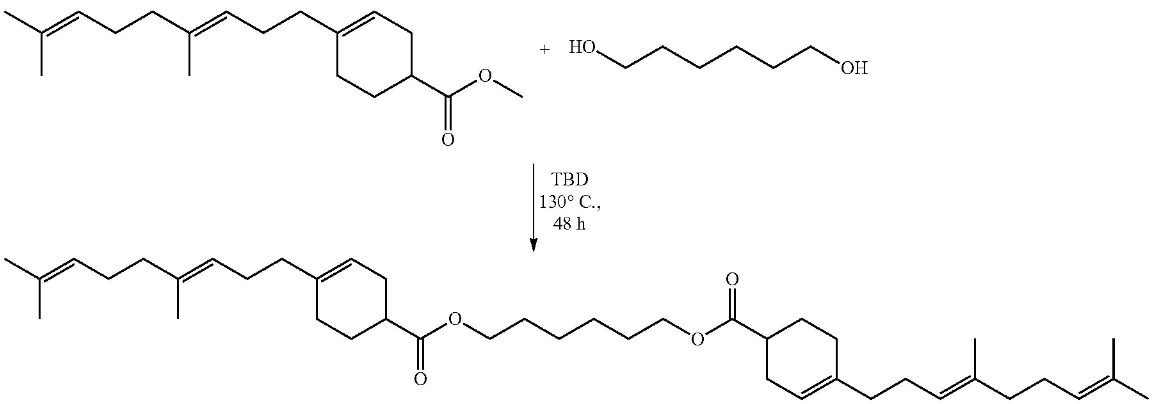

In a 4 mL sealable glass tube, farnesene methyl ester (FME) (4.9 g, 4.0 mmol, 4.0 eq) was added with the 1,6-hexanediol (0.5 g, 1.0 mmol, 1.0 eq) and a catalyst TBD (471 mg, 0.8 mmol, 0.8 eq). The tube was sealed and stirred at 130° C. for 20 h without any solvent. The reaction was cooled and purified by flash silica gel chromatography with 5-10% of EtOAc:hexanes as eluents.

The results were:

1.19 g (44%), pale yellow oil. 1H NMR (500 MHz, CDCl3) δ 5.43-5.35 (m, 2H), 5.14-5.05 (m, 4H), 4.12-4.03 (m, 4H), 2.59-2.43 (m, 2H), 2.30-1.91 (m, 26H), 1.75-1.54 (m, 24H), 1.46-1.31 (m, 4H). 13C NMR (126 MHz, CDCl3) δ 176.23, 176.19, 137.48, 136.11, 135.24, 135.22, 131.41, 124.45, 124.17, 124.14, 120.38, 119.03, 64.35, 64.30, 40.06, 39.83, 39.64, 37.81, 37.64, 30.76, 28.69, 27.88, 27.83, 26.94, 26.84, 26.38, 26.35, 25.84, 25.75, 25.70, 25.32, 24.69, 17.83, 16.15.

Then, Protocol B procedure was followed as follows:

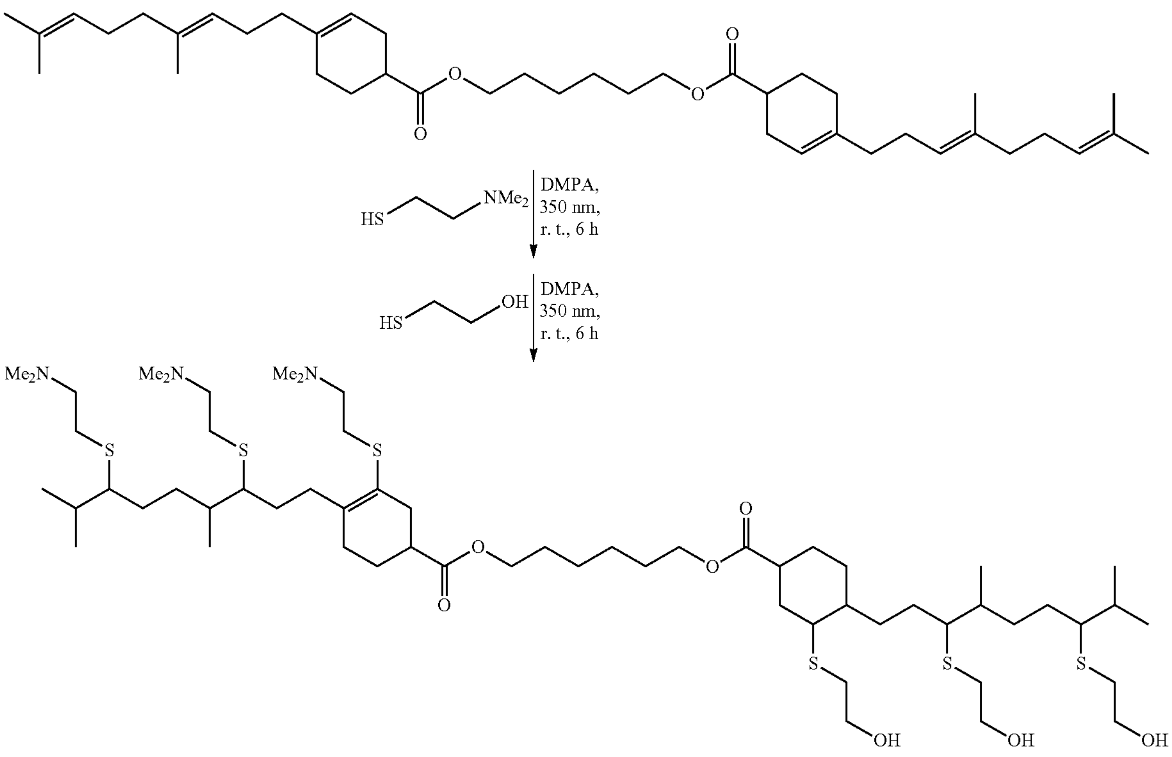

Compound 19

In a 4 mL quartz tube, corresponding bola base (400 mg, 0.63 mmol), 2-mercaptoethanol (149 mg, 1.89 mmol), and photocatalyst, 2,2-dimethoxy-2-phenyl acetophenone (DMPA) (96 mg, 0.38 mmol) were taken. A mixed solvent system of THF:MeOH (4.0 mL, 5:1) was added until all the reagents were dissolved and degassed with nitrogen for 10 mins before irradiating with 350 nm of UV light for 6 h at room temperature. The solvent was evaporated and the residue was passed through a silica gel column. Eluant 5% MeOH:DCM was used to remove nonpolar impurities and the compound was isolated with 10-50% MeOH:DCM. The pale-yellow oil obtained (330 mg, 0.38 mmol) was added 2-(dimethylamino)ethanethiol hydrochloride (271 mg, 1.9 mmol) and DMPA (98 mg, 0.38 mmol) in a quartz tube. The contents were dissolved in THF:MeOH (4.0 mL, 5:1) and degassed with nitrogen for 10 mins. The resulting reaction mixture was irradiated with 350 nm for 6 h at room temperature. The solvent was evaporated and the residue was passed through a silica gel column. Eluant 5% MeOH: DCM was used to remove nonpolar impurities and the compound was isolated with 10-50% MeOH:DCM. The off-white solid obtained was dissolved in 2.0 mL of DI water and dialyzed against water in 100-500 daltons bag for 20 h. The dialyzed solution was lyophilized to get compound 19 as a hygroscopic off-white solid (121 mg, 16%).

The results were:

1H NMR (400 MHz, DMSO-d6) δ 4.02-3.96 (m, 4H), 3.53-3.44 (m, 8H), 3.28-3.09 (m, 8H), 2.87-2.73 (m, 26H), 2.58-2.53 (m, 4H), 1.96-1.80 (m, 8H), 1.70-1.22 (m, 41H), 1.03-0.68 (m, 18H).

COMPOUND 20

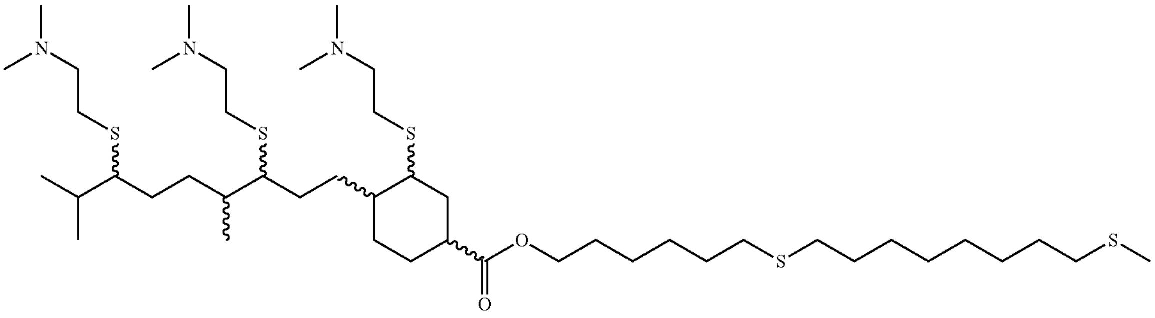

-continued

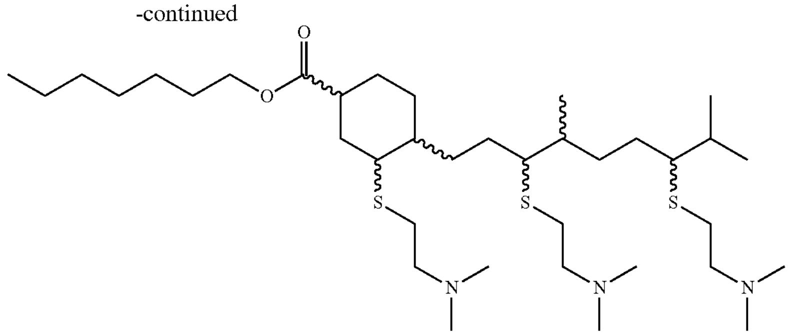

(octane-1,8-diylbis(sulfanediyl))bis(hexane-6,1-diyl) bis(4-(3,7-bis((2-(dimethylamino)ethyl)thio)-4,8-dimethylnonyl)-3-((2-(dimethylamino)ethyl)thio) cyclohexanecarboxylate)

Synthesis of Compound 20

First, C20S2 diol-linker was prepared as follows.

In a 4 mL quartz tube, 1,7-octadiene (0.2 g, 1.8 mmol, 1.0 eq), 6-mercapto-1-hexanol (0.73 g, 5.4 mmol, 1.5 eq per alkene), and photocatalyst, 2,2-Dimethoxy-2-phenylacetophenone (DMPA) (0.19 g, 0.7 mmol, 0.2 eq per alkene) were taken. A mixed solvent system of CHCl3:MeOH (2.0 mL, 5:1) was added and degassed with nitrogen for 10 mins before irradiating with 350 nm of UV light for 6 h at room temperature. The solvent was evaporated completely and the resulting residue was recrystallized with ethanol (10 mL) to give C20S2 diol.

0.41 g, (60%); off-white solid; 1H NMR (400 MHz, CDCl3) δ 3.62 (td, J=6.6, 1.0 Hz, 4H), 2.54-2.42 (m, 8H), 1.69-1.64 (m, 2H), 1.63-1.47 (m, 12H), 1.45-1.23 (m, 16H). 13C NMR (101 MHz, CDCl3) δ 77.16, 62.92, 32.70, 32.22, 32.14, 29.73, 29.69, 29.20, 28.94, 28.76, 25.48.

Then, Protocol A was followed to make a bola base of the following structure:

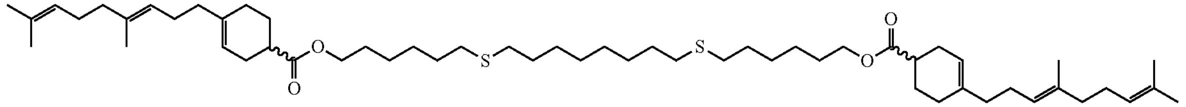 [SMILES: CC(C)=CCC/C(C)=C/CCC1=CCC(C(=O)OCCCCCCSCCCCCCCCSCCCCCCOC(=O)C2CC=C(CC/C=C(\C)CCC=C(C)C)CC2)CC1]

The results were as follows.

54% yield; $^{1}H$ NMR (400 MHz, CDCl3) δ 5.42-5.27 (m, 2H), 5.13-4.95 (m, 4H), 4.11-3.92 (m, 4H), 2.56-2.35 (m, 10H), 2.25-1.83 (m, 27H), 1.72-1.47 (m, 31H), 1.44-1.18 (m, 16H). $^{13}C$ NMR (101 MHz, CDCl3) δ 175.97, 175.94, 137.26, 135.94, 135.01, 134.98, 131.15, 124.32, 124.03, 124.01, 120.23, 118.93, 64.21, 64.16, 39.89, 39.69, 39.47, 37.68, 37.51, 32.13, 32.00, 30.62, 29.63, 29.52, 29.14, 28.86, 28.55, 28.50, 27.69, 26.70, 26.23, 26.20, 25.71, 25.59, 25.54, 25.16, 24.54, 17.69, 16.01, 15.99.

Then, Protocol B procedure was followed. The results were:

1H NMR (400 MHz, DMSO-d6) δ 4.04-3.94 (m, 4H), 3.40-3.28 (m, 12H), 3.26-3.08 (m, 18H), 2.91-2.55 (m, 46H), 2.48-2.37 (m, 6H), 2.21-1.19 (m, 56H), 1.01-0.74 (m, 18H).

COMPOUND 21

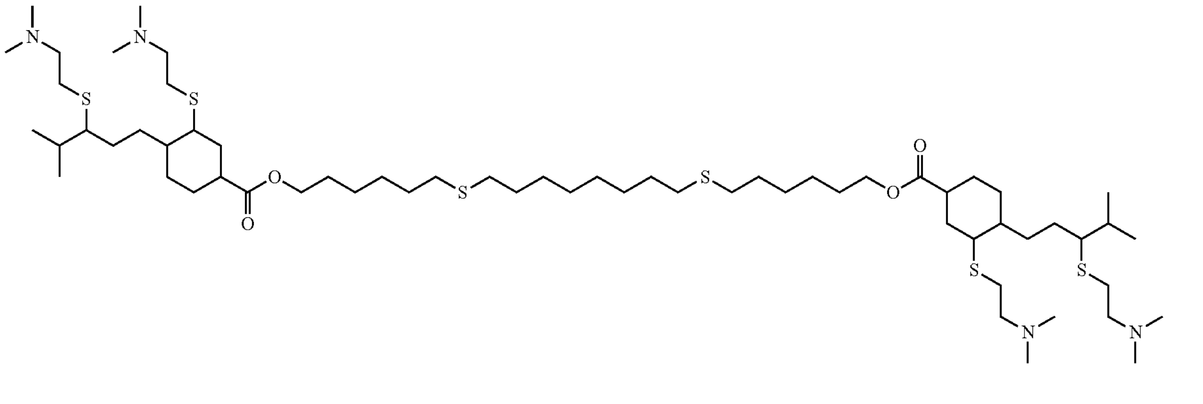

(octane-1,8-diylbis(sulfanediyl))bis(hexane-6,1-diyl) bis(3-((2-(dimethylamino)ethyl)thio)-4-(3-((2-(dimethylamino)ethyl)thio)-4-methylpentyl)cyclohexanecarboxylate)

Synthesis of Compound 21

First, C20S2 diol-linker was prepared as described in the example of preparation of Compound 20.

Then, Protocol A was followed to make a bola base of the following structure:

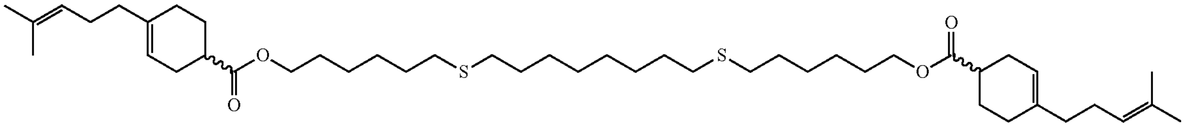 [SMILES: CC(C)=CCCC1=CCC(C(=O)OCCCCCCSCCCCCCCCSCCCCCCOC(=O)C2CC=C(CCC=C(C)C)CC2)CC1]

The results were as follows.

51% yield; 1H NMR (400 MHz, CDCl3) δ 5.38-5.28 (m, 2H), 5.09-4.97 (m, 2H), 4.06-3.97 (m, 4H), 2.53-2.36 (m, 10H), 2.21-1.83 (m, 19H), 1.64-1.48 (m, 25H), 1.40-1.22 (m, 16H). 13C NMR (101 MHz, CDCl3) δ 175.96, 175.93, 137.27, 135.97, 131.37, 131.34, 124.15, 120.18, 118.87, 64.21, 64.16, 39.87, 39.45, 37.69, 37.52, 32.13, 32.00, 32.00, 30.63, 29.63, 29.52, 29.13, 28.85, 28.54, 28.49, 27.68, 27.67, 26.35, 26.33, 25.70, 25.58, 25.52, 25.15, 24.53, 17.70, 17.68.

Then, Protocol B procedure was followed. The results were:

1H NMR (400 MHz, DMSO-d6) δ 4.06-3.91 (m, 4H), 3.29-3.03 (m, 14H), 2.92-2.75 (m, 6H), 2.75-2.60 (m, 24H), 2.47-2.30 (m, 10H), 2.21-1.16 (m, 52H), 1.00-0.75 (m, 12H).

Example 2—Preparation of Bolaplexes

Chemicals Used: Compounds 3 and 11;

pDNA (Mwt: 25382.8 KD, KiloDaltons);

DOPE: 1,2-Dioleoyl-sn-glycero-3-phosphoethanolamine;

PBS (phosphate buffered saline) buffer of pH 7.4.

Instrument: Zetasizer Nano (Malvern Instruments) for size measurements.

The bolaplexes were prepared in PBS buffet at pH 7.4 by mixing both solutions of DNA and the corresponding bolas. The bola solutions were prepared by adding aliquots of their stock (in PBS at pH 7.4) solutions to the buffer. DOPE was added 1:1 ratio to bola concentration. The final DNA concentration was 20 μM while the bola concentrations was adjusted according to a desired N/P (5, 10, 20) ratio. The N/P ratio between bolas and pDNA was expressed as the molar ratio between all the protonable amino groups of the bolas and the phosphate groups of the DNA. The DLS experiments were performed after 10 min of incubation at room temperature. The average size of the complexes was determined with a Zetasizer Nano (Malvern Instruments) at a scattering angle of 173° (temperature: 25° C.).

The results are shown in FIG. 1. FIG. 1 is a bar graph showing the size (Z-ave: average diameter) of the nanoparticle formed with various concentrations (uM: micromolar, nM: nanomolar concentrations; N/P: molar ratio of amine content in bola to the phosphate content in pDNA) of individual components and bolaplexes with and without DOPE. Comp: compound number; Compounds 3 & 11 were tested.

Table 1 provides the size, diameter in nm (population %), of bolaplexes formulated with and without DOPE.

TABLE 1

| Composition | N/P 5 | N/P 10 | N/P 20 |
|---|---|---|---|
| Comp 3/DNA | 664 (87%) | 778 (69%) | 888 (85%) |
| Comp 3/DOPE/DNA | 810 (60%) | 245 (85%) | 240 (97%) |

TABLE 1-continued

| Composition | N/P 5 | N/P 10 | N/P 20 |
|---|---|---|---|
| Comp 11/DNA | 645 (83%) | 566 (94%) | 707 (76%) |
| Comp 11/DOPE/DNA | 575 (88%) | 232 (86%) | 300 (95%) |

What is claimed is:

1. A compound of Formula (I):

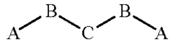

Formula (I)

wherein:

each A is independently selected from:

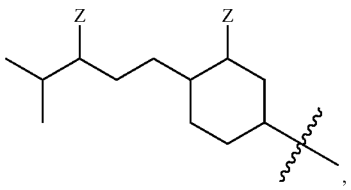

,

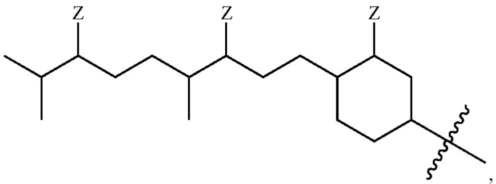

,

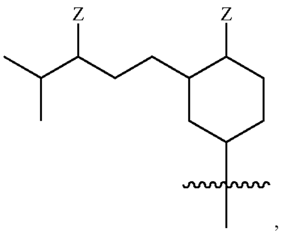

,

-continued

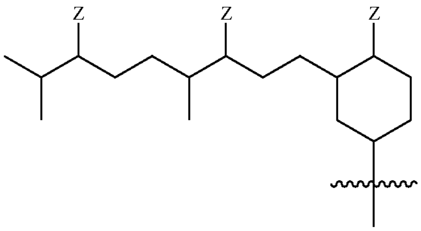

,

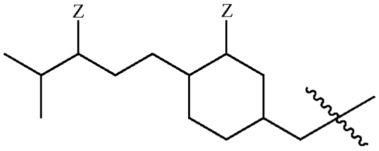

,

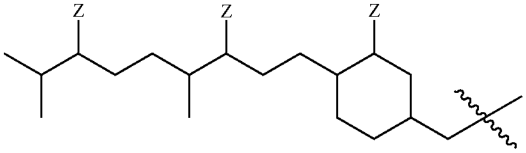

,

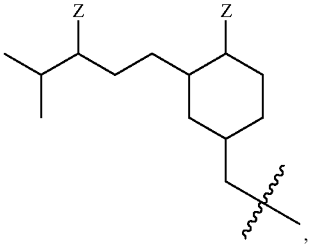

,

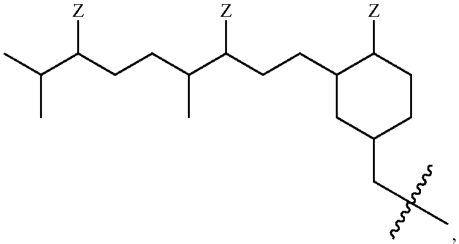

,

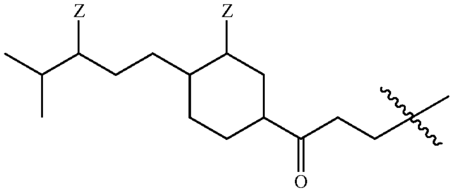

,

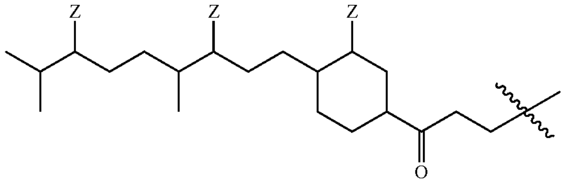

,

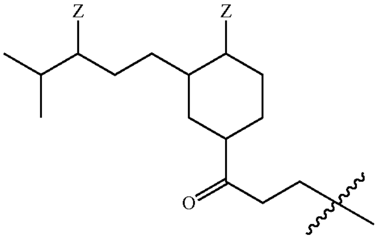

,

-continued

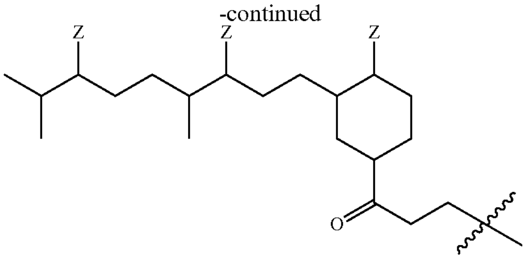

,

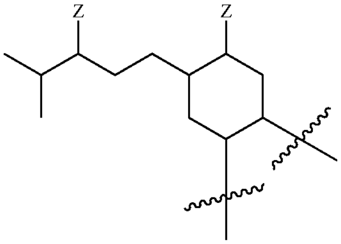

, or

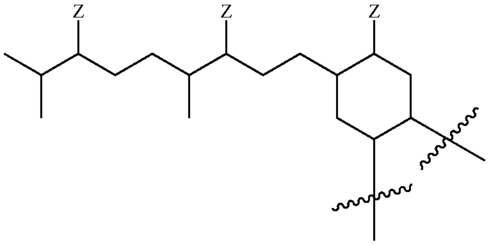

;

each Z is independently —S—$R_1$;

each $R_1$ is independently selected from:

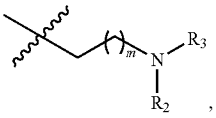

,

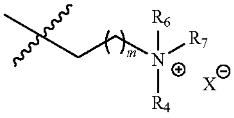

,

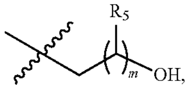

or

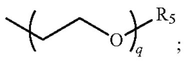

;

each $R_2$ or $R_3$ is independently selected from hydrogen, $C_1$-$C_6$ alkyl, $C_1$-$C_6$ alkenyl, aralkyl, or hydroxyalkyl;

each $R_4$, $R_6$ or $R_7$ is independently selected from $C_1$-$C_6$ alkyl, $C_1$-$C_6$ alkenyl, or hydroxyalkyl;

each $R_5$ is hydrogen or $C_1$-$C_3$ alkyl;

each X is halogen;

each m is an integer independently selected from 1-10;

each q is an integer independently selected from 1-200;

each B is independently selected from:

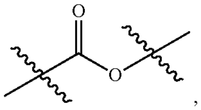

,

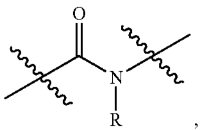

,

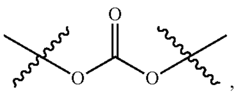

,

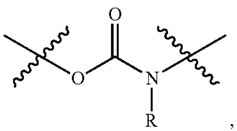

, or

-continued

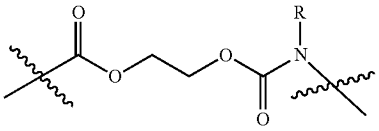

, wherein each R is independently selected from hydrogen or $C_1$-$C_6$ alkyl; and C is:

a. a C2-C100 hydrocarbon chain which can optionally contain one or more S atoms;

b. $Cyc^A$-L-$Cyc^B$, wherein $Cyc^A$ and $Cyc^B$ are each independently a 5-8 membered cycloalkyl chain and L is $C_1$-$C_3$ alkylene;

c. a polyalkylene oxide or polyalkylene oxide block copolymers of 200-5,000 molecular weight;

d. an aliphatic or aromatic polyester of 200-5,000 molecular weight; or e. an aliphatic or aromatic polyurethane of 200-5,000 molecular weight; or

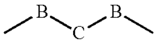

together form:

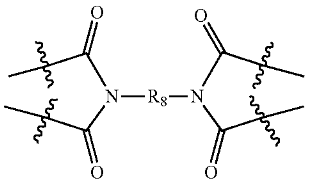

wherein each $R_8$ is independently selected from C2-C6 alkyl, aryl,

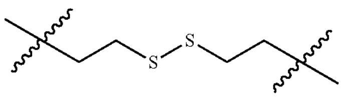

,

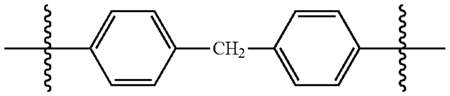

,

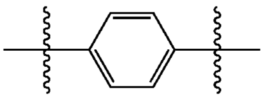

,

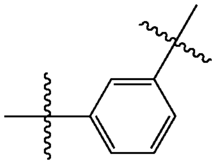

, or

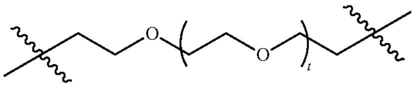

and wherein each t is an integer independently selected from 1-10.

2. The compound of claim 1, wherein each A is:

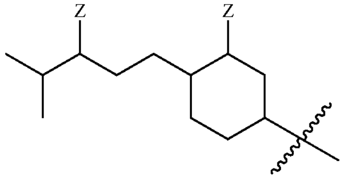

.

3. The compound of claim 1, wherein each A is:

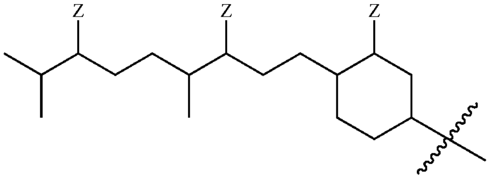

.

4. The compound according to claim 2, wherein Z is —S—$R_1$, and wherein at least one $R_1$ is:

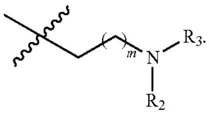

5. The compound of claim 4, wherein m is one, $R_2$ and $R_3$ are each $C_1$-$C_6$ alkyl.

6. The compound of claim 5, wherein each $C_1$-$C_6$ alkyl is methyl.

7. The compound according to claim 2, wherein each B is:

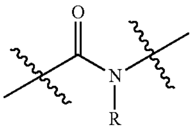

, wherein the carbonyl group of each B is linked to A in Formula (I).

8. The compound of claim 7, wherein R is hydrogen.

9. The compound according to claim 2, wherein each B is:

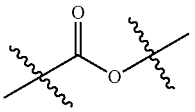

, wherein the carbonyl group of each B is linked to A in Formula (I).

10. The compound according to claim 2 wherein each B is

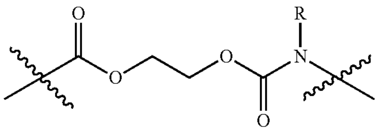

, wherein the carbonyl group of each B is linked to A in Formula (I).

11. The compound according to claim 10, wherein R is hydrogen.

12. The compound according to claim 2, wherein C is a C2-C100 hydrocarbon chain.

13. The compound of claim 12, wherein the C2-C100 hydrocarbon chain is C6 hydrocarbon chain.

14. The compound of claim 13, wherein the C6 hydrocarbon chain is hexanylene.

15. The compound of claim 12, wherein the C2-C100 hydrocarbon chain is C12 hydrocarbon chain.

16. The compound of claim 15, wherein the C12 hydrocarbon chain is dodecanylene.

17. The compound of claim 12, wherein C2-C100 hydrocarbon chain is C20 hydrocarbon chain.

18. The compound of claim 17, wherein the C20 hydrocarbon chain is icosanylene.

19. The compound according to claim 2, wherein C is $Cyc^A$-L-$Cyc^B$, wherein $Cyc^A$ and $Cyc^h$ are each independently a 5-8 membered cycloalkyl chain and L is $C_1$-$C_3$ alkylene.

20. The compound of claim 19, wherein $Cyc^A$ and $Cyc^B$ are each cyclohexyl and L is methylene.

21. The compound according to claim 2, wherein C is:

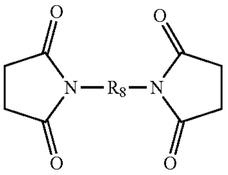

wherein each Ra is independently selected from C2-C6 alkyl, aryl,

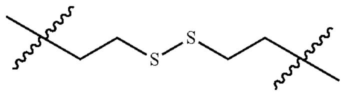

,

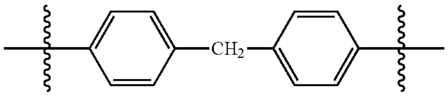

,

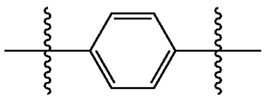

,

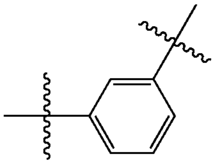

, or

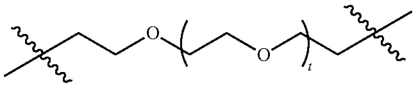

and wherein each t is an integer independently selected from 1-10.

22. The compound of claim 1, wherein the compound is:

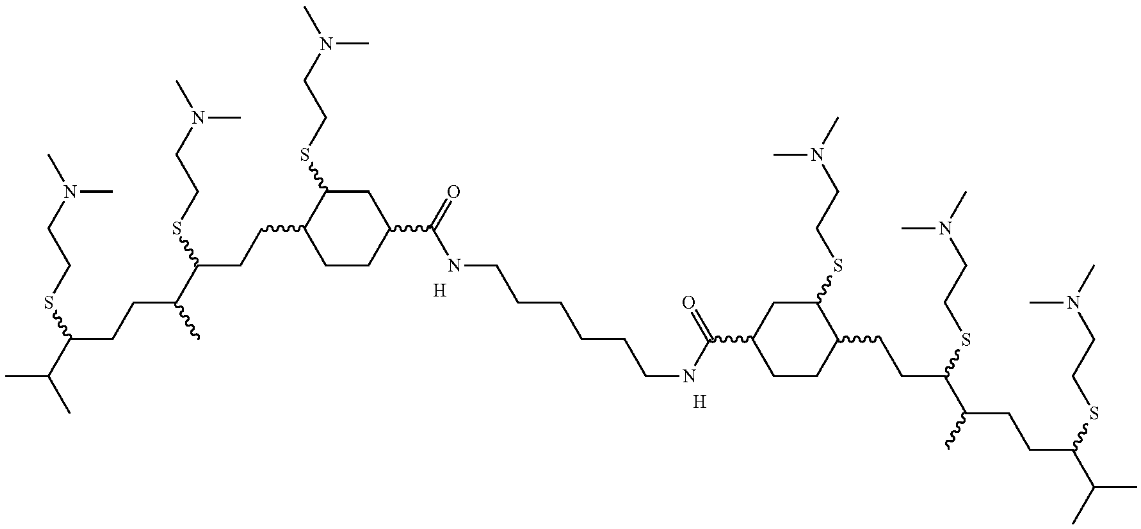

,

-continued
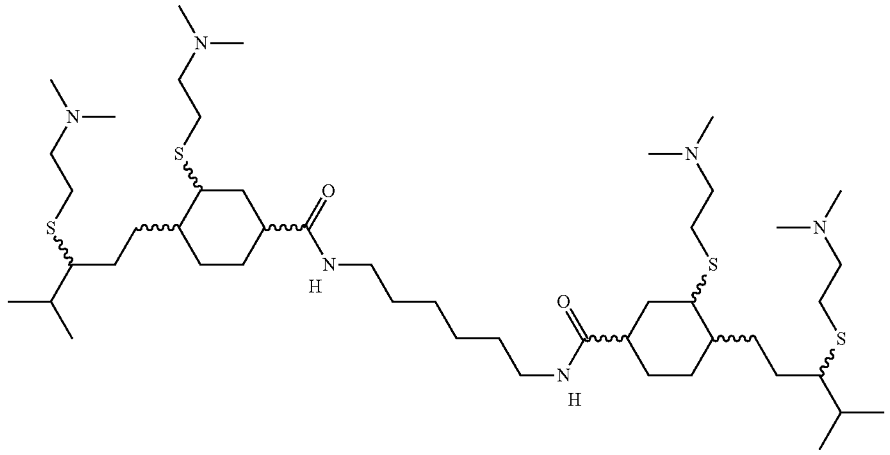
,
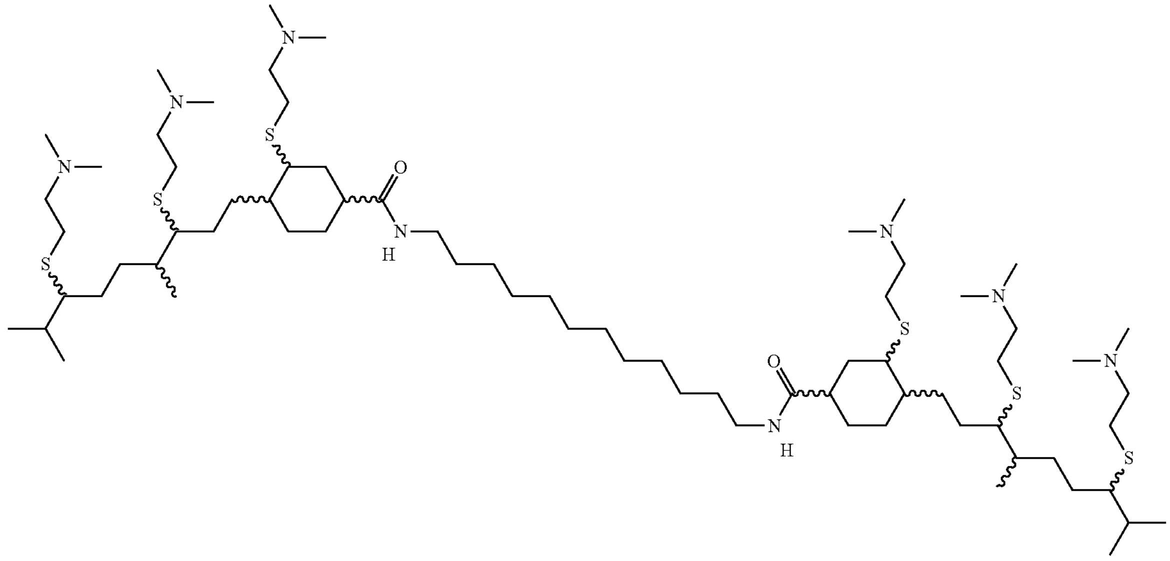
,
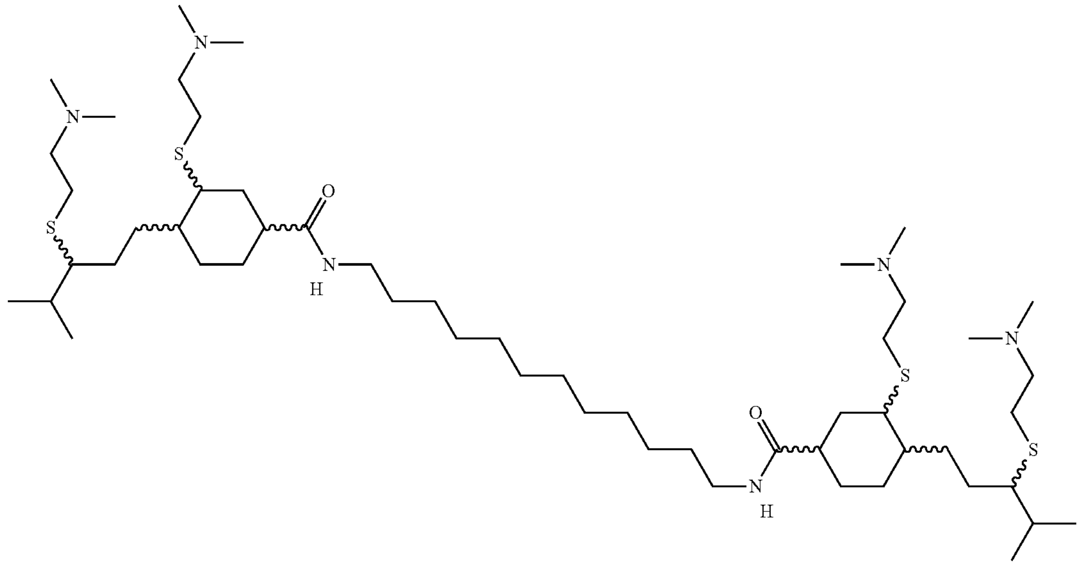
,

-continued
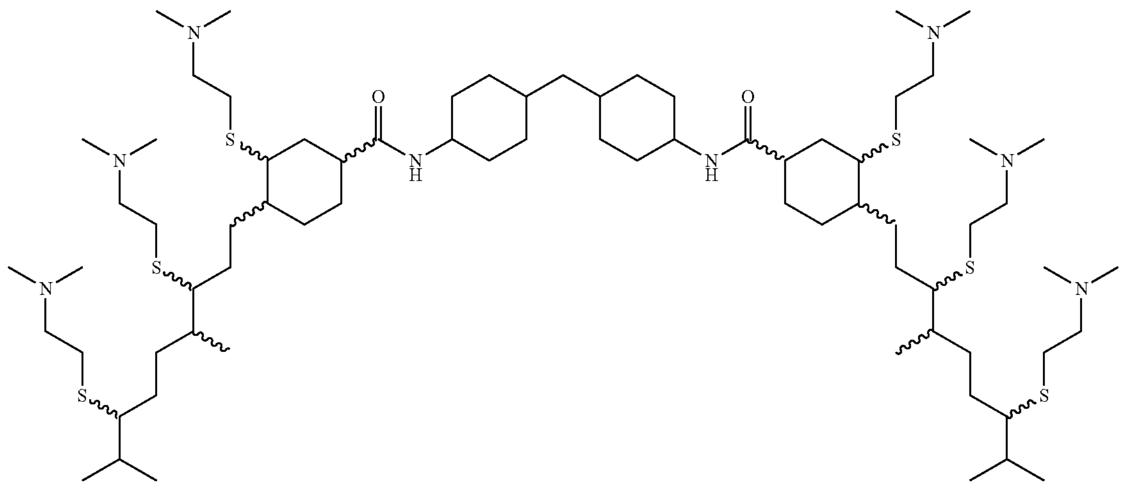
,
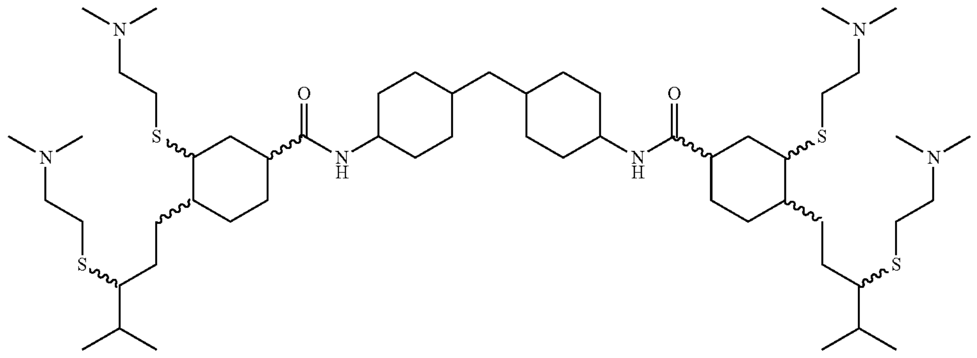
,
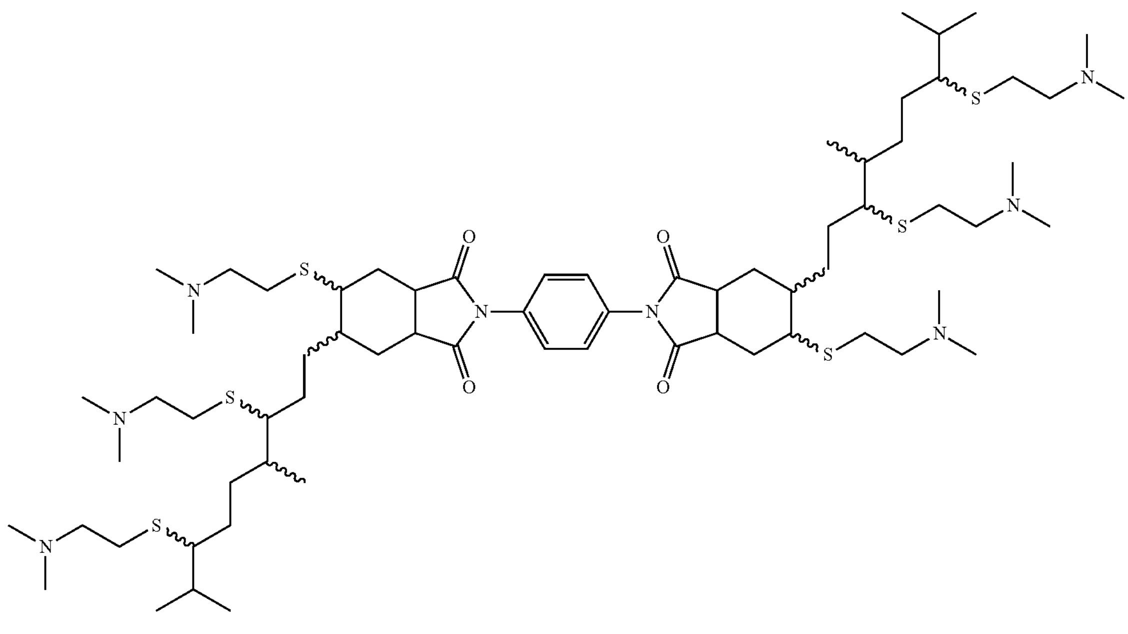
,

-continued
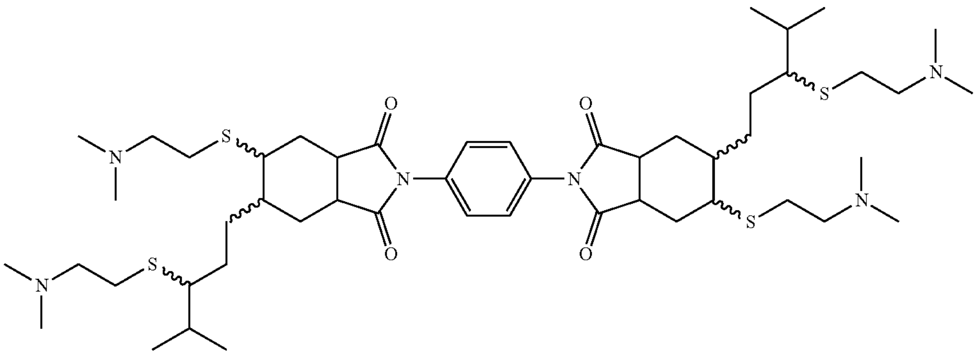
,
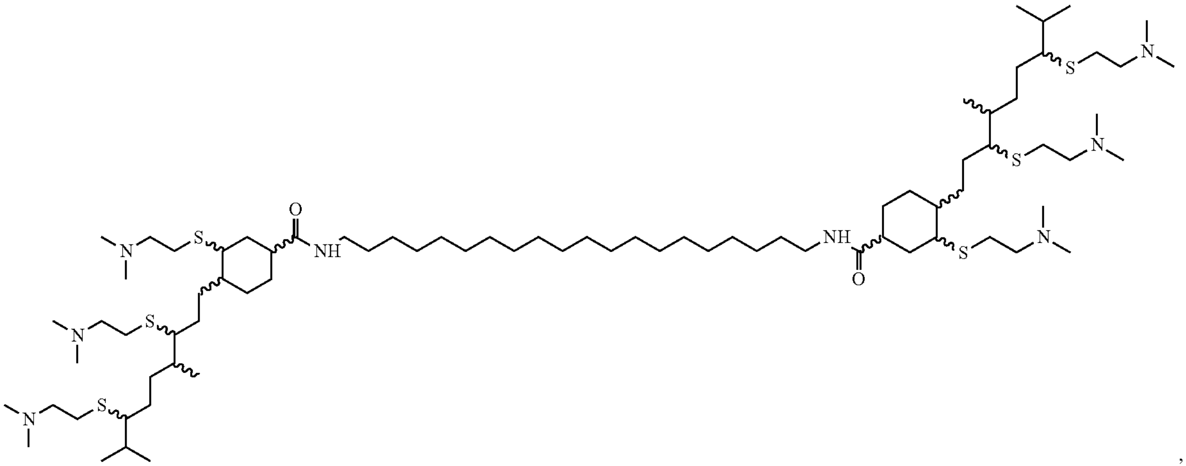
,
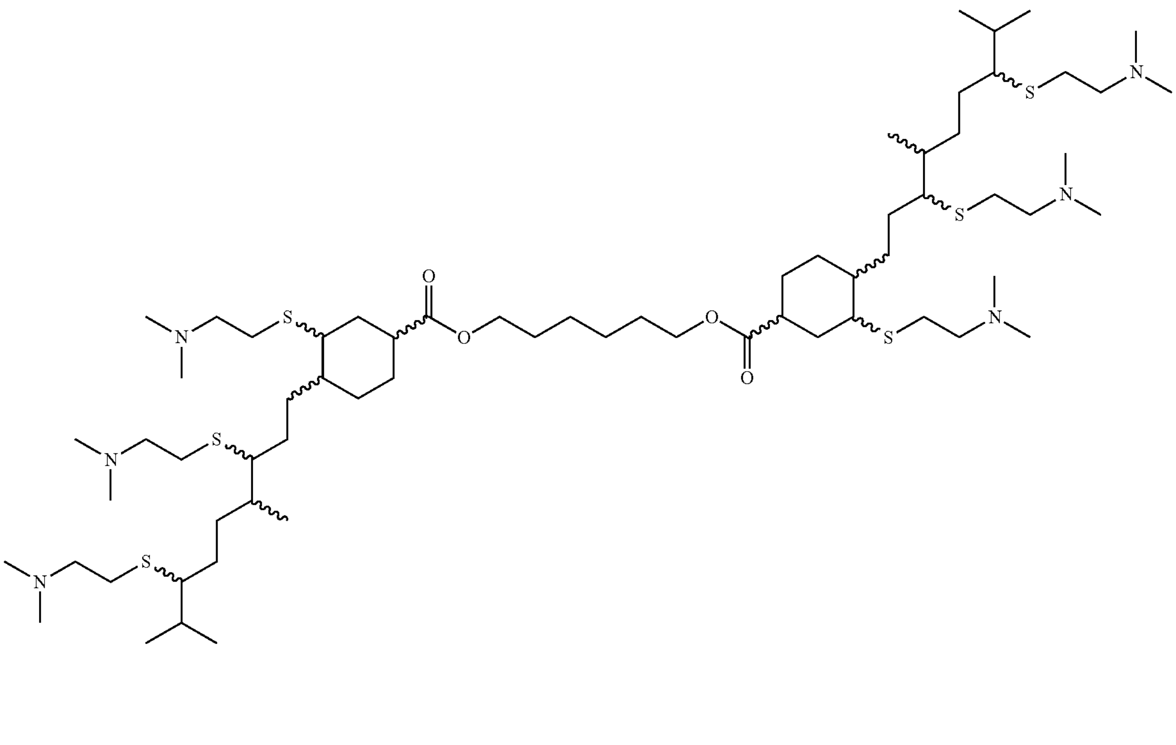
,

-continued
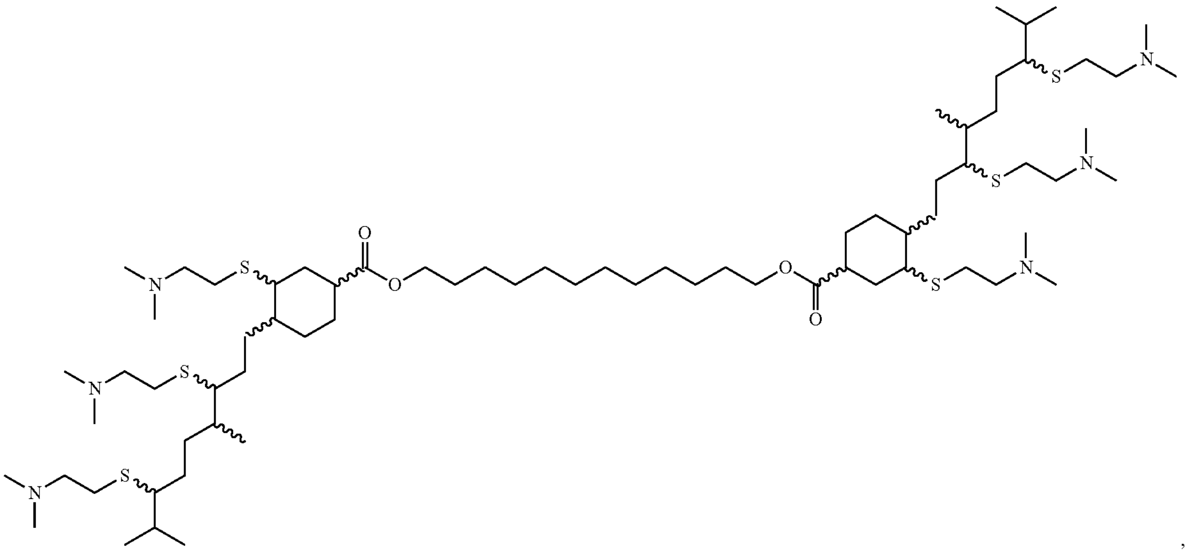
,
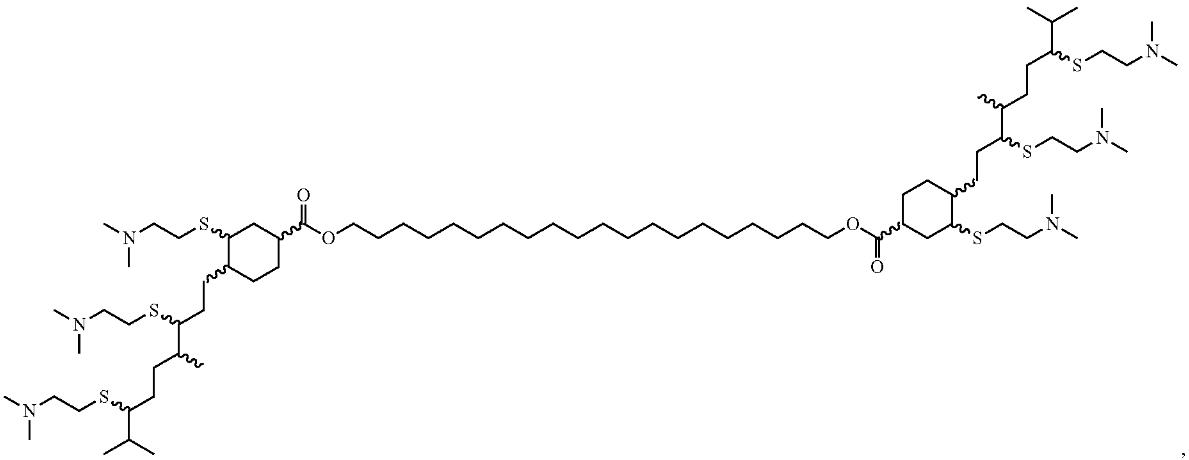
,
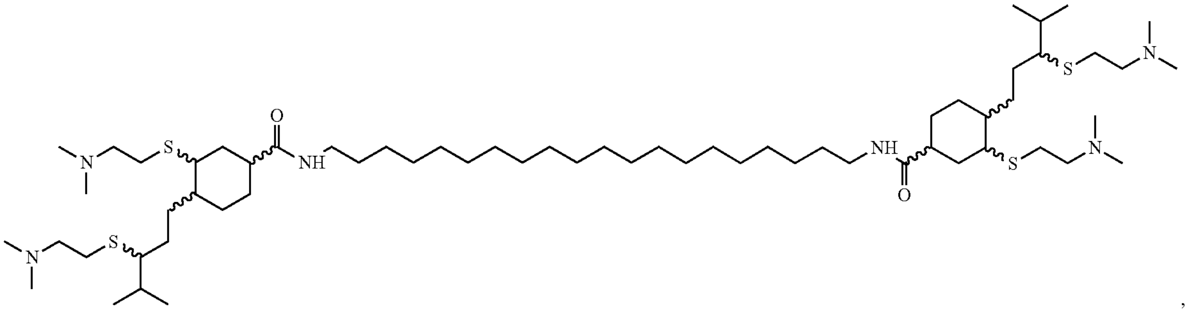
,

-continued
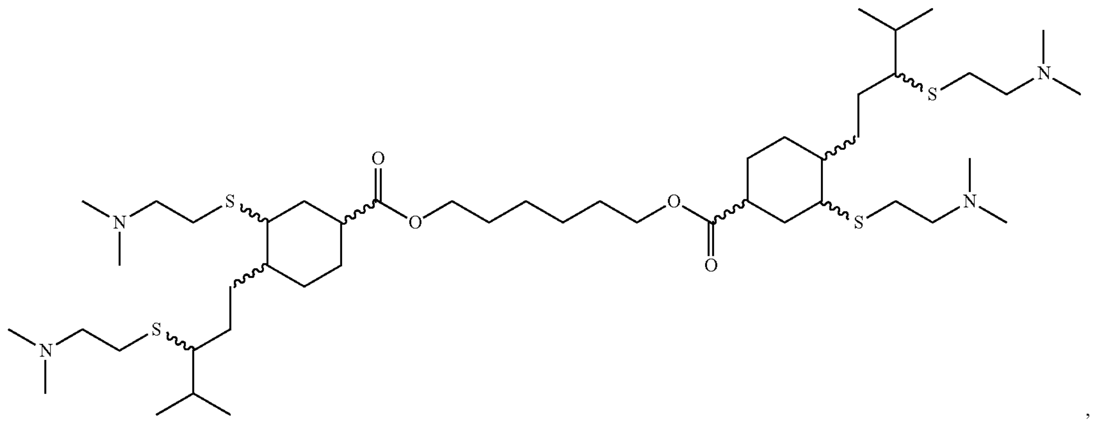
,
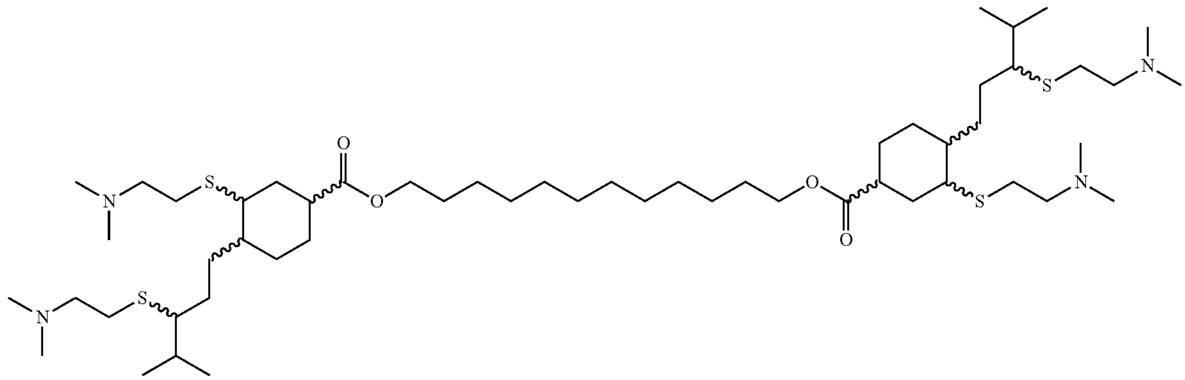
,
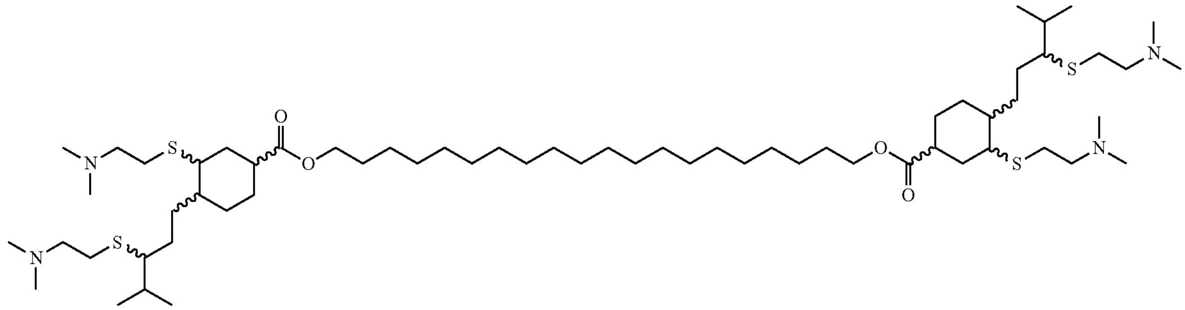
,
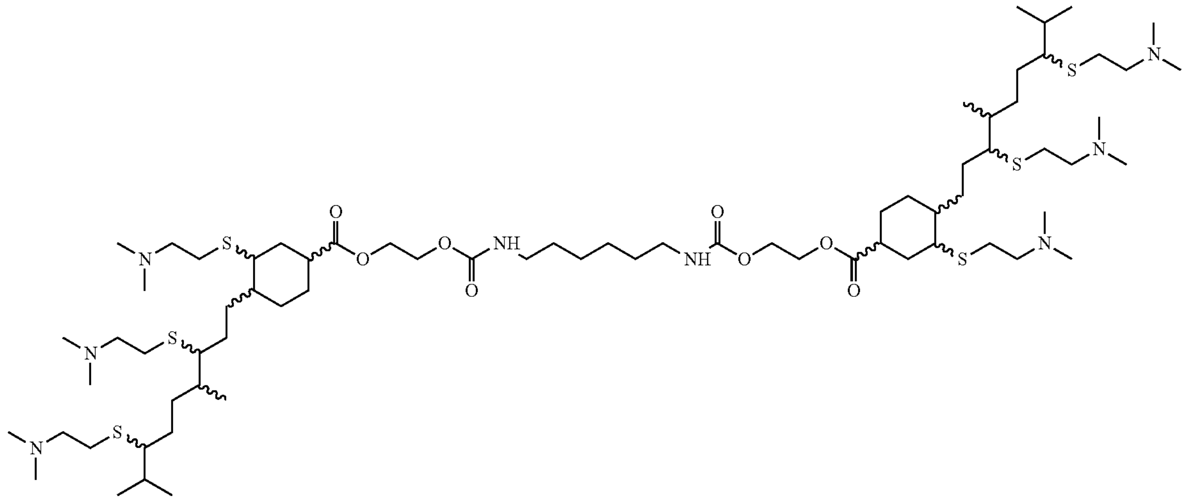
,

-continued
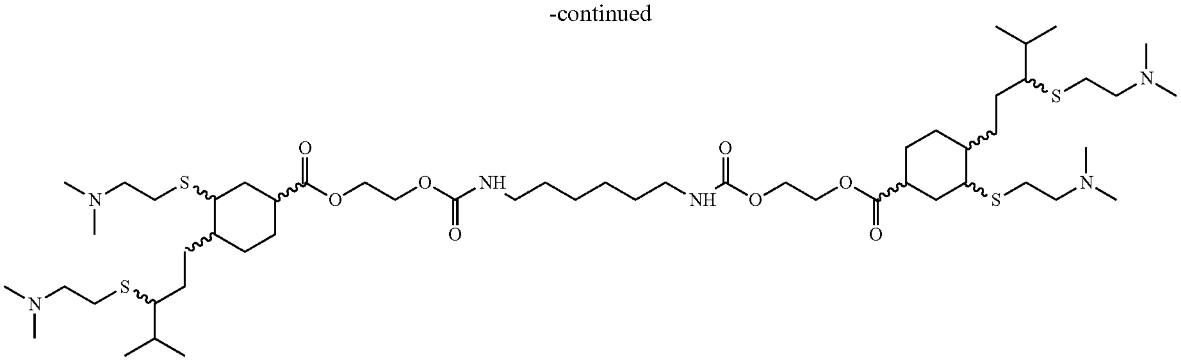
,
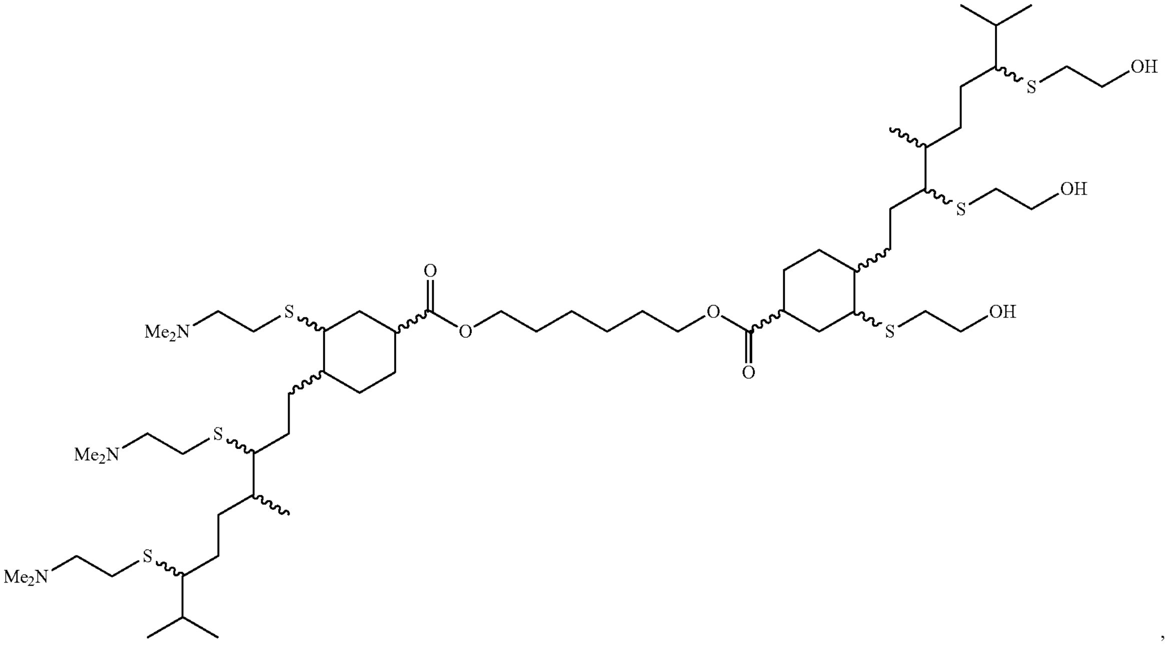
,
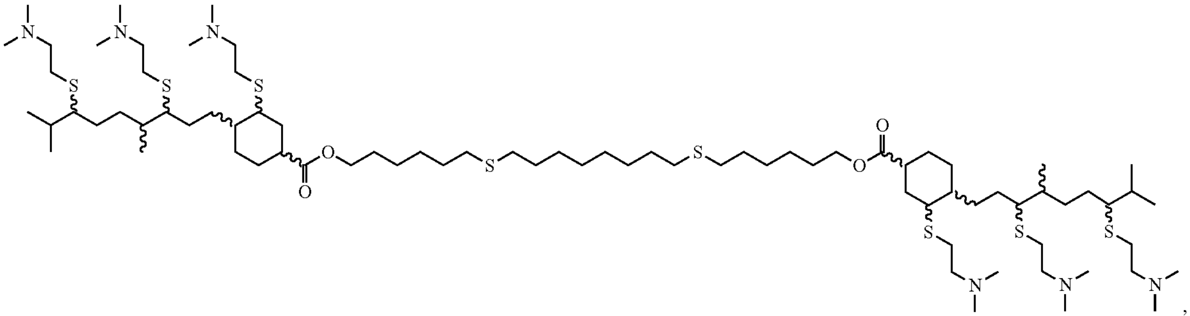
,
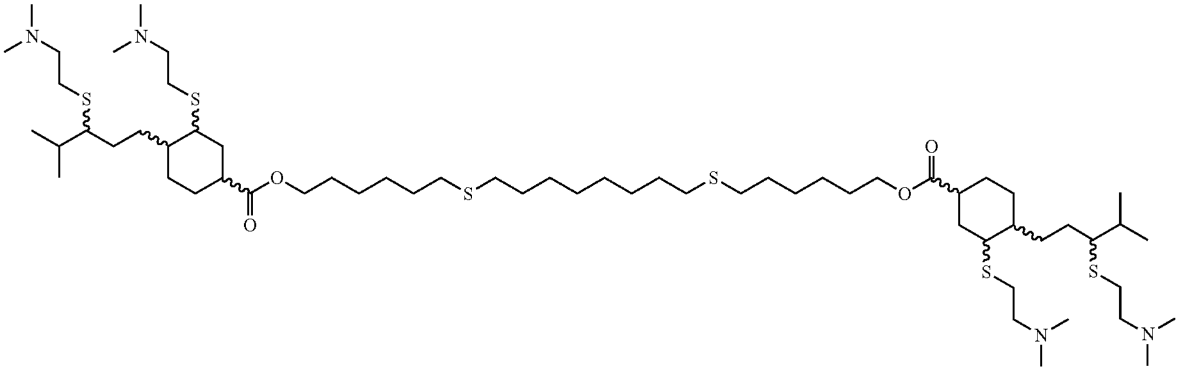
.

23. A pharmaceutical composition, comprising at least one nucleic acid, a compound of claim 1, and at least pharmaceutically acceptable excipient or diluent.

24. A lipoplex nanoparticle, comprising at least one nucleic acid and a compound of claim 1.

25. A method for delivering a nucleic acid to a cell, tissue, organ, animal or subject, comprising contacting the cell, the tissue, the organ, the animal or the subject with an effective amount of the pharmaceutical composition of claim 23.

* * * * *